(12) United States Patent (10) Patent No.: US 7,985,570 B2
Wieland et al. (45) Date of Patent: Jul. 26, 2011

(54) ALKALINE PROTEASES AND DETERGENTS AND CLEANERS COMPRISING THESE ALKALINE PROTEASES

(75) Inventors: Susanne Wieland, Dormagen-Zons (DE); Karl-Heinz Maurer, Erkrath (DE); Beatrix Kottwitz, Erkrath (DE); Frank Niehaus, Heppenheim (DE); Patrick Lorenz, Nibelungenstrasse (DE)

(73) Assignee: B.R.A.I.N. Biotechnology Research and Information Network A.G., Zwingenberg (DE)

( * ) Notice: Subject to any disclaimer, the term of this patent is extended or adjusted under 35 U.S.C. 154(b) by 0 days.

(21) Appl. No.: 12/718,086

(22) Filed: Mar. 5, 2010

(65) Prior Publication Data

US 2010/0298198 A1 Nov. 25, 2010

Related U.S. Application Data

(60) Division of application No. 11/552,061, filed on Oct. 23, 2006, now Pat. No. 7,691,618, which is a continuation of application No. PCT/EP2005/003983, filed on Apr. 15, 2005.

(30) Foreign Application Priority Data

Apr. 23, 2004 (DE) .......................... 10 2004 019 751

(51) Int. Cl.
*C12N 9/48* (2006.01)
*C11D 3/386* (2006.01)
(52) U.S. Cl. ........................................ 435/212; 510/300
(58) Field of Classification Search .................. None
See application file for complete search history.

(56) References Cited

U.S. PATENT DOCUMENTS

| | | | |
|---|---|---|---|
| 3,893,929 A | 7/1975 | Basadur | |
| 3,985,923 A | 10/1976 | Basadur | |
| 4,116,885 A | 9/1978 | Derstadt et al. | |
| 4,280,439 A | 7/1981 | Jackson | |
| 4,664,839 A | 5/1987 | Rieck | |
| 5,230,891 A | 7/1993 | Nakayama et al. | |
| 5,344,770 A | 9/1994 | Hitomi | |
| 5,352,604 A | 10/1994 | Wilson et al. | |
| 5,453,372 A | 9/1995 | Vetter et al. | |
| 5,614,161 A | 3/1997 | Wilkens et al. | |
| 5,705,169 A | 1/1998 | Stein et al. | |
| 5,730,960 A | 3/1998 | Stein et al. | |
| 5,783,545 A | 7/1998 | Paatz et al. | |
| 6,075,001 A | 6/2000 | Wilde | |
| 6,087,315 A | 7/2000 | Rasmussen et al. | |
| 6,110,884 A | 8/2000 | Rasmussen et al. | |
| 6,187,055 B1 | 2/2001 | Kottwitz et al. | |
| 6,193,960 B1 | 2/2001 | Metzger et al. | |
| 6,228,827 B1 | 5/2001 | Penninger et al. | |
| 6,379,394 B1 | 4/2002 | Chilou et al. | |
| 6,407,247 B1 | 6/2002 | Habeck et al. | |
| 6,509,021 B1 | 1/2003 | Weiss et al. | |
| 6,541,233 B1 | 4/2003 | Hillen et al. | |
| 6,905,868 B2 | 6/2005 | Estell | |
| 6,991,922 B2 | 1/2006 | Dupret et al. | |
| 7,153,818 B2 | 12/2006 | Breves et al. | |
| 7,262,042 B2 | 8/2007 | Weber et al. | |
| 7,300,782 B2 | 11/2007 | Breves et al. | |
| 7,320,887 B2 | 1/2008 | Kottwitz et al. | |
| 7,449,187 B2 | 11/2008 | Weber et al. | |
| 7,569,226 B2 | 8/2009 | Weber et al. | |
| 7,811,076 B2 | 10/2010 | Weiland et al. | |
| 2004/0005695 A1 | 1/2004 | Miksch et al. | |
| 2004/0235125 A1 | 11/2004 | Kottwitz et al. | |
| 2004/0259222 A1 | 12/2004 | Breves et al. | |
| 2005/0009167 A1 | 1/2005 | Weber et al. | |
| 2005/0026269 A1 | 2/2005 | Kottwitz et al. | |
| 2005/0049165 A1 | 3/2005 | Kottwitz et al. | |

FOREIGN PATENT DOCUMENTS

| | | |
|---|---|---|
| CA | 2306376 | 10/2000 |
| CA | 2326758 | 5/2001 |
| DE | 1617141 | 4/1972 |
| DE | 2253063 | 5/1973 |
| DE | 2200911 | 10/1973 |
| DE | 2857292 | 2/1980 |
| DE | 3324258 | 1/1984 |
| DE | 4013142 | 10/1991 |
| DE | 4443177 | 6/1996 |
| DE | 19601063 | 9/1996 |
| DE | 19616693 | 11/1997 |
| DE | 19616767 | 11/1997 |
| DE | 19616769 | 11/1997 |

(Continued)

OTHER PUBLICATIONS

E.L. Smith et al., "Subtilisin Carlsberg The complete sequence: comparison with subtilisin BPN'; evolutionary relationships," Journal of Biological Chemistry, vol. 243, No. 9, pp. 2184-2191, May 1968.
Van Raay et al., "Zur Bestimmung der proteolytischen Aktivität in Enzymkonzentraten und enzymhaltigen Wasch-, Spül- und Reinigungsmitteln," Tenside, vol. 7, pp. 125-132 (1970).
K. Horikoshi et al., "Alkalophilic Microorganisms—A New Microbial World," Japan Scientific Societies Press, Sprinter-Verlag, Heidelberg, Berlin, New York, pp. 11-26 (1982).
J.A. Wells et al., "Cloning, sequencing, and secretion of *Bacillus amyloliquefaciens* subtilisin in *Bacillus subtilis*," Nucleic Acids Research, vol. 11, No. 22, pp. 7911-7925 (1983).

(Continued)

*Primary Examiner* — Sheridan Swope
(74) *Attorney, Agent, or Firm* — DT Ward, P.C.

(57) ABSTRACT

The present application relates to two novel proteases (SEQ ID NO: 4 and 7) which are similar to one another. The DNA of the two proteases, was obtained from soil samples, and C-terminally deleted, producing proteolytically active fragments thereof (SEQ ID NO: 5 and 8). The invention also provides all alkaline proteases similar at least to 90% to SEQ ID NO: 4 or to 87.5% to SEQ ID NO: 7, and those which can be summarized under a consensus sequence (SEQ ID NO: 9) derived from SEQ ID NO: 4 and 7. Furthermore, it relates to all nucleic acids which have a homology of at least 85% identity to the associated nucleic acids (SEQ ID NO: 3 and 6) or the fragments concerned. Furthermore, it defines technical possibilities of use for these proteases and especially describes their use in detergents and cleaners.

13 Claims, 11 Drawing Sheets

FOREIGN PATENT DOCUMENTS

| | | |
|---|---|---|
| DE | 19616770 | 11/1997 |
| DE | 19709284 | 9/1998 |
| DE | 19712033 | 9/1998 |
| DE | 19857543 | 6/2000 |
| DE | 19918267 | 10/2000 |
| DE | 10138753 | 3/2003 |
| DE | 10360805 | 7/2005 |
| EP | 0066944 | 12/1982 |
| EP | 0164514 | 12/1985 |
| EP | 0185427 | 6/1986 |
| EP | 0199404 | 10/1986 |
| EP | 0241984 | 10/1987 |
| EP | 0241985 | 10/1987 |
| EP | 0251446 | 1/1988 |
| EP | 0253567 | 1/1988 |
| EP | 0272033 | 6/1988 |
| EP | 0274907 | 7/1988 |
| EP | 0283075 | 9/1988 |
| EP | 0357280 | 3/1990 |
| EP | 0472042 | 2/1992 |
| EP | 0493398 | 7/1992 |
| EP | 0525239 | 2/1993 |
| EP | 0693471 | 1/1996 |
| EP | 0694521 | 1/1996 |
| EP | 0728749 | 8/1996 |
| EP | 0736084 | 10/1996 |
| EP | 0747471 | 12/1996 |
| EP | 0755944 | 1/1997 |
| EP | 0818450 | 1/1998 |
| EP | 1288282 | 3/2003 |
| GB | 1154730 | 6/1969 |
| GB | 1243874 | 8/1971 |
| GB | 1377092 | 12/1974 |
| GB | 2123848 | 2/1984 |
| GB | 2165856 | 4/1986 |
| WO | WO-8807581 | 10/1988 |
| WO | WO-8808028 | 10/1988 |
| WO | WO-8808033 | 10/1988 |
| WO | WO-8909819 | 10/1989 |
| WO | WO-9102792 | 3/1991 |
| WO | WO-9106637 | 5/1991 |
| WO | WO-9221760 | 12/1992 |
| WO | WO-9307276 | 4/1993 |
| WO | WO-9318140 | 9/1993 |
| WO | WO-9427970 | 12/1994 |
| WO | WO-9428102 | 12/1994 |
| WO | WO-9428103 | 12/1994 |
| WO | WO-9429426 | 12/1994 |
| WO | WO-9500626 | 1/1995 |
| WO | WO-9507770 | 3/1995 |
| WO | WO-9510591 | 4/1995 |
| WO | WO-9514075 | 5/1995 |
| WO | WO-9514759 | 6/1995 |
| WO | WO-9517498 | 6/1995 |
| WO | WO-9523221 | 8/1995 |
| WO | WO-9526398 | 10/1995 |
| WO | WO-9532232 | 11/1995 |
| WO | WO-9602653 | 2/1996 |
| WO | WO-9625489 | 8/1996 |
| WO | WO-9629397 | 9/1996 |
| WO | WO-9634092 | 10/1996 |
| WO | WO-9707770 | 3/1997 |
| WO | WO-9709446 | 3/1997 |
| WO | WO-9714804 | 4/1997 |
| WO | WO-9718287 | 5/1997 |
| WO | WO-9724177 | 7/1997 |
| WO | WO-9725399 | 7/1997 |
| WO | WO-9731085 | 8/1997 |
| WO | WO-9812307 | 3/1998 |
| WO | WO-9906573 | 2/1999 |
| WO | WO-9949057 | 9/1999 |
| WO | WO-9957154 | 11/1999 |
| WO | WO-9957254 | 11/1999 |
| WO | WO-0001826 | 1/2000 |
| WO | WO-0001831 | 1/2000 |
| WO | WO-0009679 | 2/2000 |
| WO | WO-0024882 | 5/2000 |
| WO | WO-0060042 | 10/2000 |
| WO | WO-0107575 | 1/2001 |
| WO | WO-0138471 | 5/2001 |
| WO | WO-0168821 | 9/2001 |
| WO | WO-0181597 | 11/2001 |
| WO | WO-0210356 | 2/2002 |
| WO | WO-0236727 | 5/2002 |
| WO | WO-0244350 | 6/2002 |
| WO | WO-02088340 | 11/2002 |
| WO | WO-03002711 | 1/2003 |
| WO | WO-03038082 | 5/2003 |
| WO | WO-03054177 | 7/2003 |
| WO | WO-03054184 | 7/2003 |
| WO | WO-03054185 | 7/2003 |
| WO | WO-03055974 | 7/2003 |
| WO | WO-03056017 | 7/2003 |
| WO | WO-2004033668 | 4/2004 |

OTHER PUBLICATIONS

N. Vasantha et al., "Genes for Alkaline Protease and Neutral Protease from *Bacillus amyloliquefaciens* Contain a Large Open Reading Frame Between the Regions Coding for Signal Sequence and Mature Protein," Journal of Bacteriology, vol. 159, No. 3, pp. 811-819, Sep. 1984.

B. Meloun et al., "Complete primary structure of thermitase from *Thermoactinomyces vulgaris* and its structural features related to the subtilisin-type proteinases," FEBS Letters, vol. 183, No. 2, pp. 195-200 (1985).

M. Jacobs et al., "Cloning, sequencing and expression of subtilisin Carlsberg from *Bacillus licheniformis*," Nucleic Acids Research, vol. 13, No. 24, pp. 8913-8926 (1985).

D. J. Lipman et al., "Rapid and Sensitive Protein Similarity Searches," Science, vol. 227, pp. 1435-1441, Mar. 1985.

P. Nedkov et al., "Determination of the Complete Amino-Acid Sequence of Subtilisin DY and its Comparison with the Primary Structures of the Subtilisins BPN' Carlsberg and Amylosacchariticus," Biol. Chem. Hoppe-Seyler, vol. 366, pp. 421-430, Apr. 1985.

K.D. Jany et al., "Proteinase K from Tritirachium album Limber," Biol. Chem. Hoppe-Seyler, vol. 366, pp. 485-492, May 1985.

R.J. Kaiser et al., "Specific-primer-directed DNA sequencing using automated fluorescence detection," Nucleic Acids Research, vol. 17, No. 15, pp. 6087-6102 (1989).

Liu et al., "A multipurpose broad host range cloning vector and its use to characterise an extracellular protease gene of *Xanthomonas campestris* pathovar *campestris*," Molecular & General Genetics: MGG, vol. 220, No. 3, pp. 433-440, XP001207135, Feb. 1990.

T.A. Lundström et al., "Stratum Corneum Chymotryptic Enzyme: A Proteinase Which May Be Generally Present in the Stratum Corneum and With a Possible Involvement in Desquamation," Acta Derm Venereol (Stockh), vol. 71, pp. 471-474 (1991).

Goddette et al., "The Crystal Structure of the *Bacillus lentus* Alkaline Protease, Subtilisin BL at 1.4 Å Resolution," Journal of Molecular Biology, vol. 228, pp. 580-595 (1992).

Gayle et al., "Identification of Regions of Interleukin-1α Important for Activity," J Biol. Chem., vol. 268, No. 29, pp. 22105-22111, Oct. 15, 1993.

W. Stemmer, "Rapid evolution of a protein in vitro by DNA shuffling," Letters to Nature, vol. 370, pp. 389-391, Aug. 4, 1994.

R. Siezen, "Subtilases: Subtilisin-like Serine Proteases" in Subtilisin Enzymes Practical Protein Engineering. Edited by Bott & Betzel, Plenum Press, New York and London, pp. 75-95, (1996).

P. Finkel, "Formulierung kosmetischer Sonnenschutzmittel," SOFW-Journal, vol. 122, pp. 543-548 (1996).

J. Zhou et al., "DNA Recovery from Soils of Diverse Composition," Applied and Environmental Microbiology, vol. 62, pp. 316-622, Feb. 1996.

S.F. Altschul et al., "Gapped BLAST and PSI-BLAST: a new generation of protein database search programs," Nucleic Acids Research, vol. 25, No. 17 pp. 3389-3402 (1997).

H. Zhao et al., "Molecular evolution by staggered extension process (StEP) in vitro recombination," Nature Biotechnology, vol. 16, pp. 258-261 Mar. 1998.

Z. Shao et al., "Random-priming in vitro recombination: an effective tool for directed evolution," Nucleic Acids Research, vol. 26, No. 2, pp. 681-681 (1998).

H. Uhlig, "Industrial enzymes and their applications," John Wiley & Sons, Inc., New York (1998).

Fallert-Müller et al., "Lexikon der Biochemie in zwei Bänden," Spektrum Akademischer Verlag, Heidelberg Berlin, pp. 227-229 and 267-271 (1999).

R. Breier et al., "Rein enzymatische Antifilzausrüstung von Wolle nach dem Lanazym-Verfahren," Melliand Textilberichte, pp. 298-302 (2000).

Santosa, D.A., "Rapid Extraction and Purification of Environmental DNA for Molecular Cloning Applications and Molecular Diversity Studies," Molecular Biotechnology, vol. 17, pp. 59-64 (2001).

W. Coco et al., "DNA shuffling method for generating highly recombined genes and evolved enzymes," Nature Biotechnology, vol. 19, pp. 354-359, Apr. 2001.

R. Gupta et al., "Bacterial alkaline proteases: molecular approaches and industrial applications," Appl. Microbiol. Biotechnol., vol. 59, pp. 15-32 (2002).

P. Lorenz et al., "Metagenome—a challenging source of enzyme discovery," Journal of Molecular Catalysis, B: Enzymatic, 19-20, 13-19 (2002).

Whisstock et al., "Prediction of protein function from protein sequence and structure," Quarterly Reviews of Biophysics, vol. 36, No. 3, pp. 307-340, Aug. 2003.

Figure 1 / Part 1

```
                        1                                                          50
SEQ ID NO: 7    HP53    MITNSSSVPG DPQRLRQRAL VVLGGSVLST LLLAAPAFAG DVQLSGLASA
SEQ ID NO: 4    HP70    .MSHDS.... QPR.LRQRAL VVLGASVLST LLLAAPAFAG DVQLSGLSSA
SEQ ID NO: 14   SP      .MSTAS.... LR..KRTGSL TILGASALTS LLLAMPAFAG EVYLDGLATA
SEQ ID NO: 15   BLAP    .......... .......... .MMRKKSFWL GMLTAFMLVF TMAFSDSASA 51                                                         100
                HP53    PTHQRFIVKY KDGATDVATP TALASSLKAA AQAVPAAQGR ALGLQKLRQL
                HP70    PTHQRFIVKY KDGANLVATP TALASSLKAA ASAVPAAQGR ALGLQKLRQL
                SP      QTHQKFIVTY KDGSTALASP SALTTSLKTA ARAVPAKAGK ALGLNSVRRL
                BLAP    ARAEEAKEKY LIGFNEQEAV SEFVEQVEAN DEVAILSEEE EVEIELLHEF 101                                                        150
                HP53    AIGPTVVKAD RPLDAAESEL LMRRLAADPN VEYVEVDQLM HATLVPNDSR
                HP70    AIGPTVVKAD RPLDAAESEL LMRRLAADPN VEYVEVDQLM HATLVPNDAR
                SP      ALGPELVRAD RALDRAEAET LMRQLAADPN VQSVEVDQIL HATLTPNDTR
                BLAP    ETIPVLSVEL SPED...... VD.ALELDPA ISYIEEDAEV TTMAQSVPWG 151                                                        200
                HP53    LSEQWGFGTS NASINVRPAW DKATGTGVVV AVIDTGITNH PDLNANILPG
                HP70    LSEQWGFGTS NASINVRPAW DKATGTGVVV AVIDTGITNH PDLNANILPG
                SP      LSEQWAFGTT NAGLNIRPAW DKATGSGTVV AVIDTGITSH ADLNANILAG
                BLAP    ISRVQAPAAH NRGL...... ...TGSGVKV AVLDTGISTH PDLN..IRGG 201                                                        250
                HP53    YDFISDAAMA RDGGGRDNNA NDEGDWYAAN ECGAGYPASN SSWHGTHVAG
                HP70    YDFISDAAMA RDGGGRDNNA NDEGDWYAAN ECGSGIPASN SSWHGTHVAG
                SP      YDFISDATTA RDGNGRDSNA ADEGDWYAAN ECGAGIPAAS SSWHGTHVAG
                BLAP    ASFVPGEPST QDGNG..... .......... .......... ...HGTHVAG 251                                                        300
                HP53    TIAAVTNNTT GVAGTAYNAK VVPVRVLGKC G.GYTSDIAD AIVWASGGTV
                HP70    TIAAVTNNST GVAGTAFNAK VVPVRVLGKC G.GYTSDIAD AIVWASGGTV
                SP      TVAAVTNNTT GVAGTAYGAK VVPVRVLGKC G.GSLSDIAD AIVWASGGTV
                BLAP    TIAALNN.SI GVLGVAPSAE LYAVKVLGAD GRGAISSIAQ GLEWAG....

301                                                        350
                HP53    SGVPANANPA EVINMSLGGG GSCSTTYQNA INGAVSRGTT VVVAAGNSNT
                HP70    SGVPANANPA EVINMSLGGG GTCSTTYQNA INGAVSRGTT VVVAAGNSNT
                SP      SGIPANANPA EVINMSLGGG GSCSTTMQNA INGAVSRGTT VVVAAGNDAS
                BLAP    ..N..NG..M HVANLSLGSP .SPSATLEQA VNSATSRGVL VVAASGNS.G
```

Figure 1 / Part 2

```
                      351                                                       400
SEQ ID NO: 7   HP53   NVSSSVPANC ANVIAVAATT SAGARASFSN YGAGIDVSAP GQAILSTLNS
SEQ ID NO: 4   HP70   NVSSSVPANC ANVIAVAATT SAGARASFSN YGAGIDISAP GQAILSTLNS
SEQ ID NO: 14  SP     NVSGSLPANC ANVIAVAATF SAGAKASYSN FGTGIDVSAP GSSILSTLNS
SEQ ID NO: 15  BLAP   ASSISVPARY ANAMAVGATD QNNNRASFSQ YGAGLDIVAP G......VNV 401                                                       450
               HP53   GTTVPGAASY ASYNGTSMAA PHVAGVVALV QSVAPTALSP AAIETLLKNT
               HP70   GTTVPGTASY ASYNGTSMAA PHVAGVVALV QSVAPTALTP AAIETLLKNT
               SP     GTTTPGSASY ASYNGTSMAS PHVAGVVALV QSVAPTALTP AAVETLLKNT
               BLAP   QSTYPG.STY ASLNGTSMAF PHVAGAAALV KQKNP.SWSN VQIRNHLKNT 451                                                       500
               HP53   ARALPGACSG GCGAGIVDAD AAVTAALGGT NPNPGTG..T LQNNVPVSGL
               HP70   ARALPGACSG GCGAGIVDAD AAVTAALGGT NPNPGTGT.V LQNNVPVSGL
               SP     ARALPGACSG GCGAGIVNAD AAVTAAINGG SGGGGGGGNT LTNGTPVTGL
               BLAP   ATSLG..STN LYGSGLVNAE AATR...... .......... ..........

501                                                       550
               HP53   GASSGASLAY TVAVPSGRSQ LKVTIAGGTG DADLYVRSGS APTDIVYTCR
               HP70   GAASGASLSY TVVVPSGRSQ LKVSIAGGSG DADLYVRSGS APTDTVYNCR
               SP     GAATGAKLNY TITVPAGSGT LTVTPSGGSG DADLYVRAGS APTDSAYTCR
               BLAP   .......... .......... .......... .......... ..........

551                          590
               HP53   PYLSGNNETC TITAPAAGTW HVRVKAYSTF SGVTLTAQY.
               HP70   PYLSGNNETC TITSPAAGTW HVRVKGYSTF SGVTLTAQY.
               SP     PYRSGNAETC TITAPSG.TY YVRLKAYSTF SGVTLRASY.
               BLAP   .......... .......... .......... ..........
```

Figure 2 / Part 1

```
                           1                                                         50
SEQ ID NO: 6    HP53      ATGATTACGA ATTCGAGCTC GGTACCCGGG GATCCGCAGC GC...TTGCG
SEQ ID NO: 13   HP70      .......... .......... .ATGTCTCAT GATTCGCAAC CCCGTTTGCG
SEQ ID NO: 16   SP        .......... .......... .ATGTCGACT GCGTCTCTCC GC...AAGCG
SEQ ID NO: 17   BLAP      .......... .......... .......... .......... ..........

51                                                        100
                HP53      TCAGCGTGCC TTGGTTGTAC TCGGTGGTTC GGTGCTTTCG ACCCTGCTCC
                HP70      TCAGCGTGCA TTGGTTGTAC TCGGCGCGTC CGTCCTGTCC ACCCTGCTGC
                SP        TACTGGCTCG CTCACCATCC TGGGCGCGTC CGCCCTGACC TCGCTGCTGC
                BLAP      .......... .......... .......... .......... ..........

101                                                       150
                HP53      TGGCGGCGCC GGCATTCGCC GGCGACGTGC AGTTGAGTGG CCTGGCCTCG
                HP70      TGGCCGCCCC GGCATTCGCC GGCGATGTGC AGCTGAGCGG CTTGTCGTCG
                SP        TCGCGATGCC GGCCTTTGCC GGCGAGGTCT ACCTGGATGG CCTGGCCACC
                BLAP      .......... .......... .......... .......... ..........

151                                                       200
                HP53      GCCCCGACCC ACCAGCGTTT CATCGTCAAG TACAAGGACG GCGCCACCGA
                HP70      GCACCGACGC ACCAGCGTTT CATCGTCAAA TACAAGGATG GCGCCAACCT
                SP        GCACAGACCC ATCAGAAATT CATCGTGACC TACAAGGACG GCAGCACCGC
                BLAP      .......... .......... .ATGATGAGG AAAAAGAGTT TTTG......

201                                                       250
                HP53      CGTGGCCACC CCGACCGCAC TGGCCAGTTC GCTCAAGGCC GCCGCCCAAG
                HP70      GGTCGCCACC CCGACCGCAC TGGCCAGCTC GTTGAAGGCG GCGGCCCTCG
                SP        GCTGGCCAGC CCGTCCGCGT TGACCACCTC GCTGCGCACT GCTGCGCGCG
                BLAP      GCTTGGGATG CTGACGGCCT TCATGCTCGT GTTCACGATG GCATTC..AG 251                                                       300
                HP53      CCGTTCCCGC CGCGCAGGGG CGCGCGCTGG GCCTGCAGAA GCTGCGCCAG
                HP70      CCGTACCGGC TGCGCAGGGT CGCGCGCTGG GCCTGCAGAA GCTGCGCCAG
                SP        CGGTGCCGGC CAAAGCCGGC AAGGCGCTGG GCCTGAACTC GGTGCGCCGC
                BLAP      CGATTCCGCT TCTGCA.G.. CCCGGGCTGA GGAAGCAAAA GAA....AAA 301                                                       350
                HP53      CTGGCCATCG GCCCGACCGT GGTCAAGGCC GACCGCCCGC TGGATGCCGC
                HP70      CTGGCCATTG GCCCGACCGT GGTCAAGGCC GACCGTCCGC TGGATGCCGG
                SP        CTGGCGTTGG GGCCGGAACT GGTAAGGGCA GACCGCGCCC TGGACCGCGC
                BLAP      TATTTAATTG GCTTTAATGA GCAGGAAGCT GTCAGTGAGT TTGTAGAA..
```

Figure 2 / Part 2

```
                           351                                                                  400
SEQ ID NO: 6   HP53        CGAATCGGAA CTGCTGATGC GTCGCCTGGC CCCCGATCCG AACGTGGAAT
SEQ ID NO: 3   HP70        CGAGTCGGAA CTGCTGATGC GCCGCCTGGC GGCCGACCCG AACGTGGAAT
SEQ ID NO: 16  SP          CGAGGCCGAA ACCCTGATGC GGCAATTGGC CGCTGATCCC AACGTGCAGA
SEQ ID NO: 17  BLAP        CAAGTAGAGG CAAATGACGA GG....TCGC CATTCTCTCT GAGGAAGAGG 401                                                                  450
               HP53        ACGTCGAAGT CGACCAGCTG ATGCACGCCA CCCTGGTGCC CAACGACAGC
               HP70        ACGTCGAAGT CGATCAGCTG ATGCACGCCA CCCTGGTGCC CAACGACGCG
               SP          GCGTTGAAGT CGACCAGATC CTGCATGCCA CGCTCACCCC CAACGACACC
               BLAP        AAGTCGAAAT TGAAC...TG CTTCATGA.. .....GTTTG AAACGATT..

451                                                                  500
               HP53        CGCCTGTCCG AGCAGTGGGG CTTCGGCACC AGCAACGCCT CGATCAACGT
               HP70        CGCCTGTCCG AGCAGTGGGG CTTCGGCACC AGCAACGCCT CGATCAACGT
               SP          CGGTTGTCCG AGCAGTGGGC GTTCGGCACC ACCAACGCCG GCCTGAACAT
               BLAP        C..CTGTTTT ATCCGTTGAG .TTAAGC.CC AGAA...... .GATGTGGAC 501                                                                  550
               HP53        GCGCCCGGCC TGGGACAAGG CCA..CGGGG ACCGGCGTGG TGGTGGCGGT
               HP70        GCGCCCGGCA TGGGACAAGG CCA..CCGGT ACCGGCGTGG TGGTGGCGGT
               SP          CCGCCCGGCC TGGGACAAGG CCA..CCGGC AGCGGCACGG TCGTGGCGGT
               BLAP        GCGCTTGAAC TTGATCCAGC GATTTCTTAT ATTGAAGAGG ATGCAGAAGT 551                                                                  600
               HP53        GATCGATACC GGCATCACCA A..CCATCCG GATCTGAACG CCAACATCCT
               HP70        GATCGACACC GGCATCACCA A..CCATCCG GACCTCAACG CCAACATCCT
               SP          GATTGATACC GGCATCACCA G..TCATGCC GACCTCAACG CCAACATCCT
               BLAP        .AACGACAAT GGCGCAATCA GTGCCATGGG GAATTAGCCG TGTGCAAGC.

601                                                                  650
               HP53        GCCCGGCTAT GACTTCATCA GCGAT.GCCG CGATGGCGCG CGATGGCGGT
               HP70        GCCCGGCTAT GACTTCATCA GCGAC.GCGG CGATGGCGCG CGATGGTGGC
               SP          CGCGGGCTAC GACTTCATCA GCGAT.GCGA CCACCGCACG CGATGGCAAC
               BLAP        .CCCGGCTGC C.CATAACCG TGGATTGACA GGTTCTGGTG TAAAAGTTGC 651                                                                  700
               HP53        GG.CCGCGAC A...ACAATG CCAACGACGA AGGCG..... ACTGGTA.TG
               HP70        GG.CCGTGAC A...ACAACG CGAACGATGA AGGCG..... ACTGGTA.CG
               SP          GG.CCGTGAC A...GCAACG CCGCCGACGA AGGCG..... ACTGGTA.CG
               BLAP        TGTCCTCGAT ACAGGTATTT CCACTCATCC AGACTTAAAT ATTCGTGGTG
```

Figure 2 / Part 3

```
                              701                                                               750
SEQ ID NO: 6   HP53    CCGCCAACGA ATGCGGCGCC GGCTACCCGG CCTCCAATTC CAGCTGG.CA
SEQ ID NO: 3   HP70    CCGCCAACGA GTGCGGCTCG GGCATTCCGG CGTCGAACTC GAGCTGG.CA
SEQ ID NO: 16  SP      CCGCCAACGA ATGCGGCGCC GGCAPTCCCG CCGCCAGCTC CAGCTGG.CA
SEQ ID NO: 17  BLAP    GCGCTAGCTT .TGTACCAGG GGAACCATCC ACTCAAGATG GGAATGGGCA 751                                                               800
               HP53    CGGCACCCAC GTGGCCGGCA CCATCGCCGC GGTGACCAAC AACACCACCG
               HP70    CGGTACCCAC GTAGCCGGCA CCATCGCGGC GGTGACCAAC AACAGCACTG
               SP      CGGCACCCAT GTGGCCGGCA CGGTCGCGGC AGTGACCAAC AACACCACCG
               BLAP    TGGCACGCAT GTGGCCGGGA CGATTGCTGC TTTA...AAC AATTCGATTG 801                                                               850
               HP53    GCGTGGCCGG CACCGCCTAC AACGCCAAGG TCGTCCGGT GCGCGTGCTG
               HP70    GCGTGGCCGG TACGGCATTC AACGCGAAGG TCGTCCCGGT GCGCGTGCTC
               SP      GCGTAGCCGG CACCGCCTAC GCGCCAAGG TCGTACCGGT GCGCGTGCTC
               BLAP    GCGTTCTTGG CGTAGCGCCT AGTGCGGAAC TATACGCTGT TAAAGTTTTA 851                                                               900
               HP53    GGCAAGTGCG GCGGCTATAC CTCCGA.CAT CGCCGATGCG ATCGTGTGCG
               HP70    GGCAAGTGCG GCGGTTACAC CTCCGA.CAT CGCCGATGCG ATCGTGTCGG
               SP      GGCAAGTGCG GTGGGTCGCT GTCGGA.TAT CGCCGACGCC ATCGTCTGGG
               BLAP    GGA....GCC GACGGTAGAG GTGCAATCAG CTCGATTGCC CAAGCGTTGG 901                                                               950
               HP53    CATCCGGCGG CACCGTCAGC GGCGTGCCGG CCAATGCCAA CCCGGCCGAA
               HP70    CCTCCGGCGG CACGGTCAGC GGCGTGCCGG CCAATGCCAA CCCGGCCGAA
               SP      CCTCCGGCGG CACCGTCAGC GGCATCCCGG CCAATGCTAA CCCGGCCGAG
               BLAP    AATGGGCAGG GAA...CAAT GGCATGCACG ...TTGCTAA TTTG.....A 951                                                              1000
               HP53    GTGATCAACA TGTCCCTCGG CGGCGGCGGC AGCTGCTCGA CCACCTACCA
               HP70    GTGATCAACA TGTCGCTGGG CGGCGGTGGC ACCTGCTCGA CCACCTACCA
               SP      GTGATCAACA TGTCGCTCGG CGGCGGCGGT AGCTGCTCGA CCACCATGCA
               BLAP    GT..TTAGGA AGCCCTTCGC CAAGTGCCAC ACTTG..... .........A 1001                                                             1050
               HP53    GAACGCCATC AACGGCGCGG TGTCGCGCGG CACCACCGTG GTGGTGGCAG
               HP70    GAACGCCATC AACGGCGCGG TGTCGCGCGG CACGACGGTG GTGGTGGCGG
               SP      GAACGCCATC AACGGTGCGG TGTCGCGCGG CACCACGGTG GTGGTCGCGG
               BLAP    GCAAGCTGTT AATAGCGCGA CTTCTAGAGG CGTTCTTGTT GTAGCGGCAT
```

Figure 2 / Part 4

```
                        1051                                                                      1100
SEQ ID NO: 6    HP53    CGGGCAACAG  CAACACCAAC  GTGTCCTCGT  CGGTGCCGGC  CAACTGCGCC
SEQ ID NO: 3    HP70    CGGGCAACAG  CAACACCAAC  GTGTCCTCGT  CGGTGCCGGC  CAACTGCGCC
SEQ ID NO: 16   SP      CCCGCAACGA  TGCGTCCAAT  GTGTCCGGTT  CGCTGCCGGC  CAACTGCGCG
SEQ ID NO: 17   BLAP    CTGGGAATT.  CAGGTGCAAG  CTCAA.TCAG  CTAT.CCGGC  CCGTTATGCG 1101                                                                      1150
                HP53    AACGTGATCG  CGGTGGCCGC  CACCACCTCG  GCCGGCGCCC  GCGCCAGCTT
                HP70    AACGTGATCG  CGGTGGCCGC  CACGACGTCG  GCCGGCGCGC  GCGCGAGCTT
                SP      AACGTGATTG  CGGTGGCCGC  CACCACCTCG  GCGGGCGCGA  AGGCCAGCTA
                BLAP    AACGCAATGG  CAGTCGGAGC  TACTGACCAA  AACAACAACC  GCGCCAGCTT 1151                                                                      1200
                HP53    CTCCAACTAC  GGTGCCGGCA  TCGATGTCTC  GGCGCCGGGC  CAGGCGATCC
                HP70    CTCGAACTAC  GGTGCCGGCA  TCGATATTTC  GGCGCCGGGG  CAGGCGATCC
                SP      TTCCAACTTC  GGCACCGGTA  TCGATGTGTC  GGCGCCCGGC  TCGTCGATCC
                BLAP    TTCACAGTAT  GGCGCAGGGC  TTGACATTGT  CGCACCAGG.  ...GGTAAACG 1201                                                                      1250
                HP53    TGTCCACGCT  CAACAGCGGC  ACCACCGTGC  CGGGCGCTGC  GTCCTATGCG
                HP70    TGTCCACGCT  CAACAGCGGT  ACGACGGTGC  CGGGCACGGC  GTCCTACGCG
                SP      TGTCCACGCT  CAACAGCGGC  ACCACCACGC  CGGGTAGCGC  CAGCTATGCC
                BLAP    TG......C.  ....AG....  AGCACATACC  CAGGTTCAAC  G...TATGCC 1251                                                                      1300
                HP53    TCGTACAACG  GCACCTCGAT  GGCGGCCCCG  CACGTGGCCG  GCGTGGTCGC
                HP70    TCCTACAACG  GGACGTCGAT  GGCGGCGCCG  CACGTGGCCG  GCGTGGTGGC
                SP      TCCTACAACG  GCACCTCGAT  GGCGTCGCCG  CATGTGGCCG  GCGTGGTCGC
                BLAP    AGCTTAAACG  GTACATCGAT  GGCTACTCCT  CATGTTGCAG  GTGCAGCAGC 1301                                                                      1350
                HP53    GCTGGTGCAG  TCGGTCGCGC  CCACCGCGCT  GTCGCCGGCA  GCCATCGAGA
                HP70    GCTGGTGCAG  TCGGTGGCAC  CGACGGCGTT  GACGCCGGCG  GCGATCGAGA
                SP      GCTGGTGCAG  TCGGTCGCCC  CGACCGCGCT  GACGCCAGCA  GCGGTGGAAA
                BLAP    CCTTGTTAAA  .CAAAAGAAC  CCATCTTG..  GTCCAATGTA  CAAATCCGCA 1351                                                                      1400
                HP53    CGCTGCTCAA  GAACACCGCA  CGGGCCCTGC  CGGGCGCCTG  CAGCGGCGGC
                HP70    CGTTGCTGAA  GAACACGGCA  CGGGCATTGC  CGGGCGCATG  CAGCGGTGGG
                SP      CCTTGTTGAA  GAACACCGCG  CGTGCTTTAC  CGGGCGCCTG  CTCGGGCGGC
                BLAP    ACCATCTAAA  GAATACGGCA  ACGAGCTTA.  .GGAAGCACG  AACTTG....
```

Figure 2 / Part 5

```
                          1401                                                    1450
SEQ ID NO: 6   HP53       TGCGGCGCGG GCATCGTCGA TGCGGATGCG GCCGTCACCG CCGCGCTG..
SEQ ID NO: 3   HP70       TGCGGCGCGG GCATCGTGGA CGCCGATGCG GCGGTCACGG CGGCGCTG..
SEQ ID NO: 16  SP         TGCGGTGCCG GCATCGTCAA CGCCGATGCC GCGGTCACTG CGGCCATCAA
SEQ ID NO: 17  BLAP       TATGGAAGCG GACTTGTCAA TGCAGAAGCG GCAA.CACGC TAA.......

1451                                                    1500
               HP53       .GGCGGGA.C CAACCCGAAC CCGGGCACCG GCACG...CT GCAGAACAAC
               HP70       .GGCGGGA.C GAATCCGAAC CCGGGCACGG GGACGGTGCT GCAGAACAAT
               SP         TGGCGGGAGC GGCGGCGGTG GCGGTGGTGG AAACACC.TT GACCAACGGC
               BLAP       .......... .......... .......... .......... ..........

1501                                                    1550
               HP53       GTGCCGGTCA GCGGCCTGGG TGCTTCCAGC GGTGCATCGC TGGCCTACAC
               HP70       GTGCCGGTGA GCGGTCTGGG CGCGGCCAGC GGGGCATCGC TGTCCTATAC
               SP         ACTCCGGTGA CCGGCCTGGG CGCGGCGACT GGCGCGGAAT TGAACTACAC
               BLAP       .......... .......... .......... .......... ..........

1551                                                    1600
               HP53       CGTGGCCGTG CCCTCGGGTC GCTCGCAGCT .GAAGGTGAC CATCGCCGGC
               HP70       GGTGGTGGTG CCGTCGGGCC GTTCGCAGCT .GAAGGTGAG CATCGCCGGT
               SP         CATCACCGTG CCGGCCGGCA GCG.GCACCT TGACGGTGAC CACCAGCGGC
               BLAP       .......... .......... .......... .......... ..........

1601                                                    1650
               HP53       GGCACGGGCG ATGCGGACCT GTACGTGCGC TCGGGCAGCG CGCCCACCGA
               HP70       GGCAGTGGTG ATGCGGATCT GTACGTGCGT TCGGGCAGCG CGCCGACCGA
               SP         GGCAGCGGCG ATGCCGACCT GTATGTGCGC GCCGGCAGTG CACCGACCGA
               BLAP       .......... .......... .......... .......... ..........

1651                                                    1700
               HP53       CACCGTGTAC ACCTGCCGCC CGTACCTGAG CGGCAACAAC GAAACCTGCA
               HP70       CACGGTGTAC AACTGCCGTC CGTACCTGAG CGGCAACAAC GAGACCTGCA
               SP         CTCGGCTTAC ACCTGCCGCC CATACCGCAG CGGCAATGCC GAGACCTGCA
               BLAP       .......... .......... .......... .......... ..........

1701                                                    1750
               HP53       CGATCACCG  CCCCGGCCGCG GGGACCTGGC ATGTCCGGGT GAAGGCCTAC
               HP70       HP70       CGATCACTT  CACCGGCGGCC GGTACCTGGC ACGTGCGGGT GAAGGGCTAC
               SP         CCATCACCG  CACCGTC...C GGAACGTATT ACGTGCGTCT GAAGGCCTAC
               BLAP       .......... .......... .......... .......... ..........
```

Figure 2 / Part 6

```
                        1751                                              1789
SEQ ID NO: 6   HP53     AGCACCTTC  TCCGGCGTGAC  CCTGACCGCG  CAGTATTGA
SEQ ID NO: 3   HP70     TCGACCTTC  TCCGGGGTCAC  CCTGACCGCG  CAGTACTGA
SEQ ID NO: 16  SP       AGCACGTTC  TCCGGCGTCAC  CCTGCGCGCC  AGCTACTAA
SEQ ID NO: 17  BLAP     .........  ...........  ..........  .........
```

Figure 4 / Part 1

```
                       1                                                      50
SEQ ID NO: 4   HP70    M.SHDS.... .QPRLRQRAL VVLGASVLST LLLAAPAFAG DVQLSGLSSA
SEQ ID NO: 7   HP53    MITNSSSVPG DPQRLRQRAL VVLGGSVLST LLLAAPAFAG DVQLSGLASA
SEQ ID NO: 9   Cons.   MXXXXSXXXX XXXRLRQRAL VVLGXSVLST LLLAAPAFAG DVQLSGLXSA 51                                                    100
               HP70    PTHQRFIVKY KDGANLVATP TALASSLKAA ASAVPAAQGR ALGLQKLRQL
               HP53    PTHQRFIVKY KDGATDVATP TALASSLKAA AQAVPAAQGR ALGLQKLRQL
               Cons.   PTHQRFIVKY KDGAXXVATP TALASSLKAA AXAVPAAQGR ALGLQKLRQL 101                                                   150
               HP70    AIGPTVVKAD RPLDAAESEL LMRRLAADPN VEYVEVDQLM HATLVPNDAR
               HP53    AIGPTVVKAD RPLDAAESEL LMRRLAADPN VEYVEVDQLM HATLVPNDSR
               Cons.   AIGPTVVKAD RPLDAAESEL LMRRLAADPN VEYVEVDQLM HATLVPNDXR 151                                                   200
               HP70    LSEQWGFGTS NASINVRPAW DKATGTGVVV AVIDTGITNH PDLNANILPG
               HP53    LSEQWGFGTS NASINVRPAW DKATGTGVVV AVIDTGITNH PDLNANILPG
               Cons.   LSEQWGFGTS NASINVRPAW DKATGTGVVV AVIDTGITNH PDLNANILPG 201                                                   250
               HP70    YDFISDAAMA RDGGGRDNNA NDEGDWYAAN ECGSGIPASN SSWHGTHVAG
               HP53    YDFISDAAMA RDGGGRDNNA NDEGDWYAAN ECGAGYPASN SSWHGTHVAG
               Cons.   YDFISDAAMA RDGGGRDNNA NDEGDWYAAN ECGXGXPASN SSWHGTHVAG 251                                                   300
               HP70    TIAAVTNNST GVAGTAFNAK VVPVRVLGKC GGYTSDIADA IVWASGGTVS
               HP53    TIAAVTNNTT GVAGTAYNAK VVPVRVLGKC GGYTSDIADA IVWASGGTVS
               Cons.   TIAAVTNNXT GVAGTAXNAK VVPVRVLGKC GGYTSDIADA IVWASGGTVS
```

Figure 4 / Part 2

```
                            301                                                            350
SEQ ID NO: 4   HP70    GVPANANPAE VINMSLGGGG TCSTTYQNAI NGAVSRGTTV VVAAGNSNTN
SEQ ID NO: 7   HP53    GVPANANPAE VINMSLGGGG SCSTTYQNAI NGAVSRGTTV VVAAGNSNTN
SEQ ID NO: 9   Cons.   GVPANANPAE VINMSLGGGG XCSTTYQNAI NGAVSRGTTV VVAAGNSNTN 351                                                            400
               HP70    VSSSVPANCA NVIAVAATTS AGARASFSNY GAGIDISAPG QAILSTLNSG
               HP53    VSSSVPANCA NVIAVAATTS AGARASFSNY GAGIDVSAPG QAILSTLNSG
               Cons.   VSSSVPANCA NVIAVAATTS AGARASFSNY GAGIDXSAPG QAILSTLNSG 401                                                            450
               HP70    TTVPGTASYA SYNGTSMAAP HVAGVVALVQ SVAPTALTPA AIETLLKNTA
               HP53    TTVPGAASYA SYNGTSMAAP HVAGVVALVQ SVAPTALSPA AIETLLKNTA
               Cons.   TTVPGXASYA SYNGTSMAAP HVAGVVALVQ SVAPTALXPA AIETLLKNTA 451                                                            500
               HP70    RALPGACSGG CGAGIVDADA AVTAALGGTN PNPGTGTVLQ NNVPVSGLGA
               HP53    RALPGACSGG CGAGIVDADA AVTAALGGTN PNPGTG.TLQ NNVPVSGLGA
               Cons.   RALPGACSGG CGAGIVDADA AVTAALGGTN PNPGTGXXLQ NNVPVSGLGA 501                                                            550
               HP70    ASGASLSYTV VVPSGRSQLK VSIAGGSGDA DLYVRSGSAP TDTVYNCRPY
               HP53    SSGASLAYTV AVPSGRSQLK VTIAGGTGDA DLYVRSGSAP TDTVYTCRPY
               Cons.   XSGASLXYTV XVPSGRSQLK VXIAGGXGDA DLYVRSGSAP TDTVYXCRPY 551                              587
               HP70    LSGNNETCTI TSPAAGTWHV RVKGYSTFSG VTLTAQY
               HP53    LSGNNETCTI TAPAAGTWHV RVKAYSTFSG VTLTAQY
               Cons.   LSGNNETCTI TXPAAGTWHV RVKXYSTFSG VTLTAQY
```

ALKALINE PROTEASES AND DETERGENTS AND CLEANERS COMPRISING THESE ALKALINE PROTEASES

CROSS REFERENCE TO RELATED APPLICATIONS

This application is a divisional of U.S. application Ser. No. 11/552,061 filed 23 Oct. 2006, now issued U.S. Pat. No. 7,691,618, which is a continuation of PCT/EP2005/003983 filed 15 Apr. 2005, which in turn claims priority to German Patent Application No. 10 2004 019 751.2 filed 23 Apr. 2004, each of which is incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 22, 2011, is named 20131002.txt and is 58,059 bytes in size.

FIELD OF THE INVENTION

The present application relates to two novel alkaline proteases which are similar to one another, encoded by DNA obtained from soil samples, to C-terminally deleted, likewise proteolytically active fragments thereof and all sufficiently similar alkaline proteases and nucleic acids, and methods of use of these proteases, particularly in detergents and cleaners.

BACKGROUND OF THE INVENTION

Proteases belong to the industrially most important enzymes in general. Among these, in turn, serine proteases of the subtilisin type (subtilases, subtilopeptidases, EC 3.4.21.62) which contain catalytically active amino acids are particularly important. These enzymes are nonspecific endopeptidases, i.e., they hydrolyze acid amide bonds which lie in the interior of peptides or proteins. Their pH optimum usually lies in the distinctly alkaline range. The article "Subtilases: Subtilisin-like Proteases" by R. Siezen, *Subtilisin Enzymes*, ed. R. Bott and C. Betzel, (New York 1996), pp. 75-95, for example, offers an overview of this family. Subtilases are naturally formed from microorganisms. Among these subtilases, the subtilisins formed and secreted by *Bacillus* species are of particular interest.

Proteases are established, active ingredients present in a variety of detergents and cleaners as they catalyze the breakdown of protein-containing soil on the goods to be cleaned. Ideally, synergistic effects result between the enzymes and the other constituents present in the compositions concerned. Among the detergent and cleaner proteases, subtilases are particularly preferred due to their favorable enzymatic properties, including stability and pH optimum. In addition, they are also suitable for a large number of further industrial uses, for example, as constituents of cosmetics and in the synthesis of organic chemicals.

Microorganism-containing samples from natural habitats may be cultured under conditions suitable for the production of novel enzymes, e.g., under alkaline conditions. In this way, novel alkaline proteases may be isolated. The microorganisms producing the most efficient enzymes are then selected for and purified, for example by means of plating out on protein-containing agar plates and measuring the lysis halos formed. Optionally, the genes encoding the proteases may be cloned. Such a procedure is described, for example, in the textbook *Alkalophilic Microorganisms. A new microbial world*, by K. Horikoshi and T. Akiba (Japan Scientific Societies Press, Springer-Verlag, N.Y., Heidelberg, Berlin, ISBN 0-387-10924-2, 1982), Chpt. 2, pp. 9-26.

Notably, microbially-produced alkaline proteases are already employed in detergents and cleaners. For example, see WO 93/07276 A1 which describes the protease 164-A1 from Chemgen Corp., Gaithersburg, Md., USA, and Vista Chemical Company, Austin, Tex., USA, obtainable from *Bacillus* spec. 164-A1 is suitable for use in detergents and cleaners. Other examples are the alkaline protease from *Bacillus* sp. PD138, NCIMB 40338 from Novozymes A/S, Bagsvaerd, Denmark (WO 93/18140 A1), the proteinase K-16 from Kao Corp., Tokyo, Japan (U.S. Pat. No. 5,344,770), originating from *Bacillus* sp. ferm. BP-3376 and the protease described in WO 96/25489 A1 (Procter & Gamble, Cincinnati, Ohio, USA) from the psychrophilic organism *Flavobacterium balustinum*.

Natural proteases may be optimized, for use in detergents and cleaners, via mutagenesis methods known in the art. Such methods include point mutagenesis, (e.g., generation of deletion, or insertion mutants) or fusion with other proteins or protein parts. The strategy of introducing specific point mutations into the known subtilisin molecules, in order to improve the washing performance, is also referred to as rational protein design. A similar strategy to improve performance entails modifying the surface charges and/or the isoelectric point of the molecules in order to modulate their interactions with the substrate via the introduction of point mutations. A further, supplementary strategy consists of increasing the stability of the proteases thereby increasing their efficacy. Stabilization by means of coupling to a polymer is described for proteases used in cosmetics, for example, in U.S. Pat. No. 5,230,891. Such proteases exhibit improved skin compatibility. However, for detergents and cleaners, stabilization by point mutations is more commonly employed.

A new approach in enzyme development entails combining elements of related, known proteins thereby generating novel enzymes having improved functional properties. Such methods are also referred to as "directed evolution". These include, without limitation: The StEP method (Zhao et al., *Nat. Biotechnol.*, Vol. 16 (1998), pp. 258-261), Random priming recombination (Shao et al., *Nucleic Acids Res.*, Vol. 26 (1998), pp. 681-683), DNA shuffling (Stemmer, W. P. C., *Nature*, Vol. 370 (1994), pp. 389-391) or RACHITT (Coco, W. M. et al., *Nat. Biotechnol.*, Vol. 19 (2001), pp. 354-359). A further shuffling method referred to as "Recombining ligation reaction" (RLR) is described in WO 00/09679 A1.

Below, an overview of the industrially most important alkaline proteases of the subtilisin type is provided. Subtilisin BPN', which originates from *Bacillus amylotiquefaciens*, or *B. subtilis*, is described by Vasantha et al. in *J. Bacteriol.*, Vol. 159 (1984), pp. 811-819 and J. A. Wells et al. in *Nucleic Acids Research*, Vol. 11 (1983), pp. 7911-7925. Subtilisin BPN' is used as a reference enzyme with respect to numbering of amino acid positions in the subtilisins.

For example, the position of point mutations in subtilisin described in EP 251446 A1, are indicated using the numbering of BPN' as a reference. Procter & Gamble Corp., of Cincinnati, Ohio, USA, refer to this material as "Protease B". The BPN' variants of EP 199404 A1 are referred to by Procter & Gamble Corp. as "Protease A". A "Protease C" is in turn characterized, according to WO 91/06637 A1, by further point mutations of BPN'. "Protease D" refers, according to WO 95/10591 A1, to variants of the protease from *Bacillus lentus*.

The protease subtilisin Carlsberg is described in the publications of E. L. Smith et al. in *J. Biol. Chem.*, Vol. 243 (1968), pp. 2184-2191, and Jacobs et al. in *Nucl. Acids Res.*, Vol. 13 (1985), pp. 8913-8926. It is formed naturally by *Bacillus licheniformis*, and was and is obtainable under the trade name Maxatase® from Genencor International Inc., Rochester, N.Y., USA, and under the trade name Alcalase® from Novozymes A/S, Bagsvaerd, Denmark.

Protease PB92 is produced naturally by the alkalophilic bacterium *Bacillus nov.* spec. 92 and is obtainable under the trade name Maxacal® from the Gist-Brocades company, Delft, Netherlands. It is described in its original sequence in Patent Application EP 283075 A2.

Subtilisins 147 and 309 are marketed under the trade names Esperase® and Savinase®, respectively, by Novozymes. They were originally obtained from *Bacillus* strains that are disclosed by Application GB 1243784 A.

Subtilisin DY was originally described by Nedkov et al. in *Biol. Chem. Hoppe-Seyler*, Vol. 366 (1985), pp. 421-430.

The alkaline protease from *B. lentus* is an alkaline protease from *Bacillus* species and is described in Application WO 91/02792 A1. It natively possesses comparatively good stability with respect to oxidation and the action of detergents. Application WO 91/02792 A1 and Patents EP 493398 B1 and U.S. Pat. No. 5,352,604 describe its heterologous expression in the host *B. licheniformis* ATCC 53926. The claims of the aforesaid US patent refer to positions 208, 210, 212, 213, and 268 as characteristic of the *B. lentus* alkaline protease; they correspond, in the numbering of the mature protein, to positions 97, 99, 101, 102, and 157. However this enzyme differs from the mature subtilisin 309 (Savinase®). The three-dimensional structure of this enzyme is described in "The crystal structure of the *Bacillus lentus* alkaline protease, Subtilisin BL, at 1.4 Å resolution", Goddette et al., *J. Mol. Biol.*, Vol. 228 (1992), pp. 580-595. Industrially important variants of this enzyme that are stabilized by point mutagenesis and are suitable in particular for use in washing and cleaning products are disclosed, inter alia, in Applications WO 92/21760 A1, WO 95/23221 A1, WO 02/088340 A2, and WO 03/038082 A2.

The enzyme thermitase, formed naturally by *Thermoactinomyces vulgaris*, was originally described by Meloun et al. (*FEBS Lett.* (1983), pp. 195-200). This is a molecule that as a whole exhibits substantial sequence discrepancies compared with the other subtilisins. The homology between the mature thermitase and the alkaline protease proteins from *B. lentus* DSM 5483 (see below) is not very high, (e.g., 45% identity; 62% similar amino acids).

Proteinase K is also a protease that exhibits comparatively low homology with the alkaline protease from *B. lentus*: only 33% identity (46% similar amino acids) at the level of the mature proteins. Proteinase K derives originally from the microorganism *Tritirachium album* Limber, and has been described by K.-D. Jany and B. Mayer in *Biol. Chem. Hoppe-Seyler*, Vol. 366 (1985), pp. 485-492.

WO 88/07581 A1 discloses proteases TW3 and TW7, which are very similar to one another, for use inter alia in washing and cleaning products.

Bacillopeptidase F from *Bacillus subtilis* possesses only 30% identity to the *B. lentus* alkaline protease at the amino-acid level. This enzyme is discussed in the aforementioned work by Siezen et al., but has not hitherto been described or claimed for use in washing and cleaning products.

Application WO 01/68821 A2 describes new subtilisins having good performance with respect to egg stains.

Further alkaline proteases that are formed from microorganisms that can be isolated from natural habitats are described in Applications WO 03/054185 A1 (from *Bacillus gibsonii* (DSM 14391)), WO 03/056017 A2 (from *Bacillus* sp. (DSM 14390)), WO 03/055974 A2 (from *Bacillus* sp. (DSM 14392)), and WO 03/054184 A1 (from *Bacillus gibsonii* (DSM 14393)). All these Applications also disclose corresponding washing and cleaning products containing these novel alkaline proteases.

A further group of industrially important proteases are the metalloproteases, e.g., enzymes that require a metal cation as a cofactor. Representatives of these are also assigned to the family of subtilases. For instance, metalloproteases from gram-positive microorganisms such as *B. subtilis*, but also from *S. cerevisiae, S. pombe, E. coli* and *H. influenzae*, are described in US 2003/0113895 A1. WO 00/60042 A1 and WO 02136727 A1, disclose detergents and cleaners containing metalloproteases. DE 10360805.2 discloses an alkaline metalloprotease whose encoding DNA is obtainable from a soil sample, and its use in detergents and cleaners.

A large number of novel proteases are described in WO 20041033668 A2. StmPr2 from *Stenotrophomonas maltophilia*, which is deposited under the entry AY253983 in GenBank (National Center for Biotechnology Information NCBI, National Institutes of Health, Bethesda, Md., USA), has also been previously described.

Further known protease enzymes are obtainable under the trade names Durazym®, Relase®, Everlase®, Nafizym, Natalase® and Kannase® from Novozymes, under the trade names Maxapem®, Purafect®, Purafect OxP® and Properase® from Genencor, under the trade name Protosol® from Advanced Biochemicals Ltd., Thane, India and under the trade name Wuxi® from Wuxi Snyder Bioproducts Ltd., China.

In light of the foregoing, it is clear that there is a great need for industrially employable proteases which exhibit altered activities from previously known proteases, particularly for their use in detergents and cleaners. A suitable protease for detergents or cleaners should exhibit a certain insensitivity to conditions suitable for cleaning—e.g., the presence of surfactants which are denaturing, of bleach, and high temperatures, etc.—and also exhibit catalytic activity against appropriate substrates such as the proteins found in food residues.

There also exists a need for new alkaline proteases, which are naturally obtainable but which are also amenable to further optimization by means of various mutagenesis strategies. Such novel proteases may be generated using recently established shuffling technologies. Nucleotide sequences (even if the encoded enzyme exhibits comparatively modest performance) can be shuffled to produce new variants and thus in turn provide entirely new artificial enzymes for use in a variety of industrial applications.

SUMMARY OF THE INFORMATION

In accordance with the present invention, alkaline proteases are provided which naturally bring about an improvement in the performance of washing or cleaning products.

Also included in the scope of the invention are methods for isolating such proteases. Further objects include provision of nucleic acids that encode such proteases and isolated proteases produced by expression of the same. Yet another object entails genetic-engineering such nucleic acids to develop improved proteases (e.g., by a shuffling procedure). The proteases obtained by the expression of the engineered nucleic acids also comprise an aspect of the invention. Such proteases may be used to advantage in washing and cleaning products and corresponding washing and cleaning methods. The proteases described herein may also be employed in industrial applications.

The present discovery was not based on conventional enrichment culture for alkaphilic, protease-producing microorganisms, rather, nucleic acids coding for alkaline proteases were isolated from soil samples. Because the isolated nucleic acids cannot be assigned to a specific strain of bacteria, such nucleic acids are referred to as "metagenomic DNA".

Surprisingly, according to this method two novel proteases were identified which have an extraordinary similarity to one another and are employable successfully in detergents and cleaners as complete mature enzymes or as C-terminal deletion mutants.

Thus the present invention provides an alkaline protease comprising an amino acid sequence which is identical to the amino acid sequence of SEQ ID NO. 4, or a sequence which is at least 90% identical thereto. Also provided is an alkaline protease having the amino acid sequence of SEQ ID NO. 7 and a sequence which is at least to 87.5% identical thereto.

Also in accordance with the present invention are nucleic acids encoding the proteases described above, cells comprising such nucleic acids and methods for their characterization. Also provided are detergents and cleaners comprising the proteases and methods of use for the same.

As the working examples confirm, enzymes encoded by SEQ ID NO. 4 and 7 and their associated mature enzymes exhibit proteolytic activities which are suitable for use in detergents and cleaners. Provision of the DNA encoding these enzymes facilitates additional optimization of these enzymes, via introduction of point mutations. Furthermore, these DNAs can be subjected to shuffling procedures, thereby producing completely novel proteases.

BRIEF DESCRIPTION OF THE DRAWINGS

FIG. 1: Alignment of the alkaline proteases HP70 and HP53 according to the invention (SEQ ID NO. 4 and 7) with alkaline proteases from the prior art. HP70: alkaline protease shown in SEQ ID NO. 4; HP53: alkaline protease as shown in SEQ ID NO. 7; SP: extracellular serine protease (SEQ ID NO: 14) (E.C. 3.4.21.-) from *Xanthomonas campestris* pv. *campestris* (ATCC 33913) (Accession No. NP_636242 at GenBank); BLAP: alkaline protease (SEQ ID NO: 15) from *Bacillus lentus* DSM 5483 (WO 92/21760 A1).

FIG. 2: Alignment of the genes of the alkaline proteases HP70 (nucleotides 1-1746 of SEQ ID NO: 3) and HP53 (SEQ ID NO: 6) according to the invention (SEQ ID NO. 3 and 6) with those of alkaline proteases from the prior art. HP70: gene of the alkaline protease HP70 shown in SEQ ID NO. 3; HP53: gene of the alkaline protease HP53 shown in SEQ ID NO. 6; SP: gene of the extracellular serine protease (SEQ ID NO: 16) (E.C. 3.4.21.-) from *Xanthomonas campestris* pv. *campestris* (ATCC 33913) (Accession No. NP_636242 at GenBank); BLAP: gene of the alkaline protease (SEQ ID NO: 17) from *Bacillus lentus* DSM 5483 (WO 92/21760 A1).

FIG. 4: Alignment of the amino acid sequences of the two proteases HP70 (SEQ ID NO. 4) and HP53 (SEQ ID NO. 7) according to the invention for the development of the consensus sequence of SEQ ID NO. 9. The amino acid positions designated therein as variables X can be attributed either to HP70 or to HP53 as shown in this figure.

DETAILED DESCRIPTION OF THE INVENTION

Figure 3:
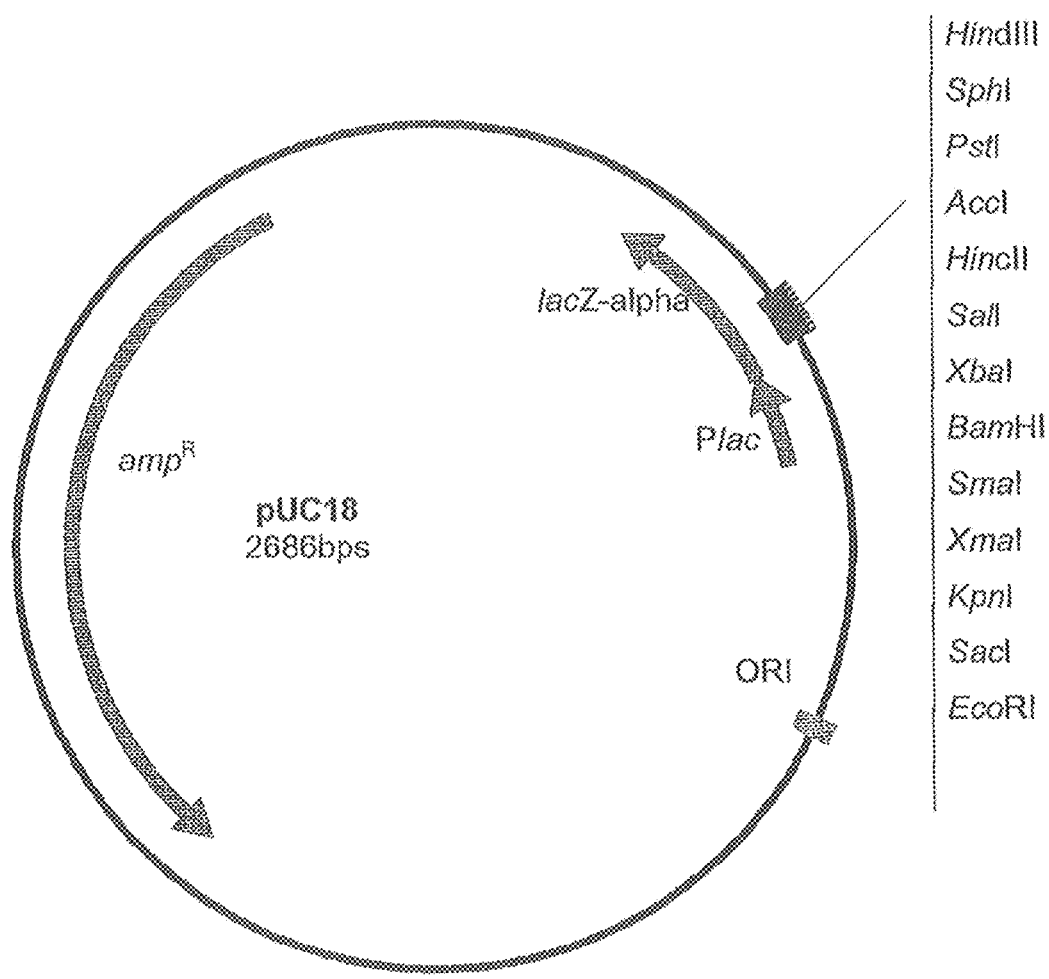
FIG. 3: Schematic representation of the plasmid vector pUC18 used for the setting up of an expression gene bank as in Example 2. The vector was linearized with Sma I for the setting up of the metagenomic DNA digested with Alu I.: ORI: replication origin Plac: lac promoter; lacZ-alpha: gene for the alpha-peptide of the beta-galactosidase; amp$^R$: ampicillin resistance-mediating beta-lactamase.

A protein within the meaning of the present application refers to a polymer composed of linearly synthesized natural amino acids, which typically assume a three-dimensional structure for effecting protein function. In the present application, the 19 proteinogenous, naturally occurring L-amino acids are designated by the customary 1- and 3-letter codes. The combination of one of these designations with a number indicates the particular amino acid residue within the respective position. Analogous designations are established for point mutations. Positional data relate, if not stated otherwise, to the mature forms of the proteins, e.g., proteins which lack signal peptides (see below).

An enzyme within the meaning of the present application is to be understood as meaning a protein which carries out a certain biochemical function. Proteolytic enzymes or enzymes having a proteolytic function are to be understood as meaning those which hydrolyze the acid amide bonds of proteins.

Numerous proteins are formed as "preproteins", that is, they also include a signal peptide sequence at the N-terminal part of the protein. Signal peptide sequences facilitate expulsion of the protein formed in the producing cell into the periplasma or the surrounding medium and/or its correct folding. Subsequently, the signal peptide is removed from the remainder of the protein under natural conditions by a signal peptidase, the mature protein exhibiting proteolytic activity.

For industrial applications, mature peptides, that is, enzymes processed as described above, are preferred compared to the pre-proteins.

Pro-proteins are inactive precursors of proteins. Their precursors having a signal sequence are designated as pre-proproteins.

Nucleic acids serve as information carriers which encode for the linear amino acid sequence in proteins or enzymes. They can be present as single stranded or as double stranded molecules. As DNA is more stable than other types of nucleic acids, it is preferred for molecular biological studies. In another aspect, nucleic acids isolated from the natural environment (e.g., an RNA) are also within the scope of the invention. (c)DNA molecules reversed transcribed from such RNA molecules also comprise as aspect of the invention.

Genes comprise the information unit of nucleic acids encoding a particular protein. In DNA, the sequences of both complementary strands are to be taken into consideration in all three possible reading frames in each case. Furthermore, various codon triplets can code for the same amino acids, so that certain amino acid sequences can be derived from a number of different nucleotide sequences, some which exhibit only low identity. This phenomenon is referred to as the degeneracy of the genetic code. Moreover, various organisms show differences in the use of these codons. For these reasons, the nucleic acids provided herein are exemplary as variations of these sequences are also within the scope of the invention due to the aforementioned degeneracy of the genetic code.

Methods such as chemical synthesis and polymerase chain reaction (PCR) in combination with other conventional molecular biology and/or protein chemistry methods, facilitate the preparation of complete genes having known DNA and/or amino acid sequences. Such methods are described, for example, in "Lexikon der Biochemie" [Encyclopedia of Biochemistry], Spektrum Akademischer Verlag, Berlin, Vol.

1 (1999), pp. 267-271 and Vol. 2, pp. 227-229. For example, known DNA sequences can be amplified with sequence specific PCR primers using isolated mRNA molecules. Nucleic acids from such strains can then be synthesized, cloned and, if desired, further mutagenized.

Modifications to the nucleotide sequence are referred to as mutations. Such mutations can include modification, deletion, insertion or substitution mutations or those in which various genes or parts of genes are shuffled or fused with one another. The organisms producing such modified nucleic acids are designated as mutants. The proteins derived from mutated nucleic acids are designated as variants. For instance, deletion, insertion, substitution mutations or fusions lead to deletion-, insertion-, substitution-mutated or fusion genes and, at the protein level, to corresponding deletion, insertion or substitution variants, or fusion proteins.

Point mutations refer single amino acid replacements and the following convention is used first, the naturally present amino acid is designated in the form of the internationally customary single-letter code, followed by the associated sequence position and finally the inserted amino acid. A number of exchanges within the same polypeptide chain are separated from one another by obliques.

Vectors within the meaning of the present invention refer to nucleic acids, which contain a gene of interest. Vectors are useful for expressing the gene of interest in a species or a cell line over a number of generations or cell divisions as a stable genetic element replicating independently of the other genome. Vectors are special plasmids, that is, circular genetic elements, when used in bacteria. A differentiation is made in genetic engineering between those vectors which are used for storage, e.g., "cloning vectors", and those which fulfill the function of producing the gene of interest in the host cell, e.g., expression vectors.

Both bacterial cells and eukaryotic cells which contain said vectors are generally designated as cells regardless of their differences. Those cells which contain a vector, in particular an expression vector, and can thus be used for the expression of a transgene, are designated as host cells, since they accommodate the genetic system concerned.

Homologization is the comparison of a nucleic acid or amino acid sequence with that of known genes or proteins. It is performed, for example, by means of alignment. The measure of the homology is a percentage of identity, as can be determined, according to the method indicated by D. J. Lipman and W. R. Pearson in *Science*, Vol. 227 (1985), pp. 1435-1441. Preferably, it is carried out by means of algorithms, which are provided by commercially obtainable computer programs. These include, for example, the program Vector NTI® Suite 7.0, obtainable from InforMax, Inc., Bethesda, USA, preferably using the specified default parameters. The homology indication can relate to the entire protein or to the range to be assigned in each case. A more widely used homology term, "similarity", relates to conserved variations, that is, amino acids having a similar chemical structures which usually exert similar chemical activities within the protein. With nucleic acids, only the percentage of identity is known.

By homologization, the functions of individual sequence ranges and the enzymatic activity of the entire enzyme can be determined from the amino acid or nucleotide sequence. Homologous ranges of different proteins are those having comparable functions, which can be recognized by identity or conserved exchanges in the primary amino acid sequence. They comprise individual amino acids, very small regions, "boxes", which are a few amino acids in length, up to long regions in the primary amino acid sequence. The functions of the homologous regions are thus also to be understood as meaning very small subfunctions of the function exerted by the entire protein, such as, for example, the formation of individual hydrogen bonds for the complexation of a substrate or transition complex. Other regions of the protein which are not involved in the actual enzymatic reaction can qualitatively or quantitatively modify them. This relates, for example, to the enzyme stability, the activity, the reaction conditions or the substrate specificity.

The term "proteolytic enzyme" or protease is therefore to be understood as meaning, beyond the functions of the few amino acid residues of the catalytically active center, all functions such as result due to the action of the entire other protein or of a part or a number of parts of the other protein on the actually catalytically active regions. It is moreover possible that also the activities of other proteases are qualitatively or quantitatively modified by one or more parts, for example of the protein according to the invention. This influencing of other factors is likewise regarded as a proteolytic activity. Proteolytically active enzymes are also those proteases whose activity at a given point in time is blocked, for example by an inhibitor. Their principal suitability is decisive for the corresponding proteolysis reaction.

Fragments are understood as meaning all proteins or peptides which are smaller than natural proteins or those which correspond to completely translated genes, and, for example, can also be obtained synthetically. On account of their amino acid sequences, they can be assigned to the complete proteins concerned. They can, for example, assume identical structures or exert proteolytic activities or subactivities. Fragments and deletion variants of starting proteins are in principle similar; while fragments are more likely smaller pieces, the deletion mutants more likely lack only short regions, and thus only individual subfunctions.

Chimeric or hybrid proteins are to be understood within the meaning of the present application as those proteins which are composed of elements which naturally originate from different polypeptide chains of the same organism or from different organisms. This procedure is also called shuffling or fusion mutagenesis. The point of such a fusion consists, for example, in bringing about or modifying an enzymatic function with the aid of the fused-on protein part according to the invention.

Proteins obtained by insertion mutation are to be understood as meaning those variants which have been obtained by means of methods known per se by insertion of a nucleic acid fragment, or protein fragment into the starting sequences. They are to be designated as chimeric proteins because of their similarity in principle. They differ from these only in the size ratio of the unmodified protein part to the size of the entire protein. In such insertion-mutated proteins, the proportion of foreign protein is lower than in chimeric proteins.

Inversion mutagenesis, that is a partial sequence reversal, can be regarded as a special form both of deletion, but also of insertion. The same applies for a new grouping of different molecular parts differing from the original amino acid sequence. It can be regarded as a deletion variant, as an insertion variant, and as a shuffling variant of the original protein.

Derivatives are understood within the meaning of the present application as meaning those proteins whose pure amino acid chain has been chemically modified. Such derivatizations can be carried out, for example, biologically in connection with the protein biosynthesis by the host organism. For this, for example, molecular biological methods, for example cotransformation with genes which provide for the modification concerned, can be employed. Derivatizations, however, can also be carried out chemically, for example by the chemical conversion of a side chain of an amino acid or by covalent bonding of another compound to the protein. Such a compound, for example, can also be other proteins which, for example, are bonded to proteins according to the invention by means of bifunctional chemical bonds. Such modifications, for example, influence the substrate specificity or the binding strength to the substrate or bring about a temporary blockage of the enzymatic activity, if the coupled substance is an inhibitor. This is useful, for example, for the storage time period. Likewise, derivatization is to be understood as meaning covalent bonding to a macromolecular carrier.

The performance of an enzyme is understood as meaning its activity in the industrial field, preferably in the context of a correspondingly aligned composition. This is based on the actual enzymatic activity, but moreover depends on further factors relevant to the particular process. These include, for example, stability, substrate binding, interaction with the material carrying the substrate or interactions with other constituents, in particular synergies.

The washing performance or the cleaning performance of a detergent, or cleaner, is to be understood within the meaning of the present application as meaning the effect which the composition considered exerts on the soiled article, for example textiles or articles with hard surfaces. Individual components of such compositions, for example individual enzymes, are assessed with respect to their contribution to the washing or cleaning performance of the entire detergent, or cleaner. From the enzymatic properties of an enzyme, a conclusion cannot be made without problems on its contribution to the washing performance of a composition. Here, further factors, for example, stability, substrate binding, binding to the articles to be cleaned or interactions with other constituents of the detergent or cleaner, in particular synergies, play a role in the removal of the soiling.

The amino acid sequences indicated in SEQ ID NO. 4 and 7 have, as described in the examples of the present application, been derived from nucleic acids which have been isolated from soil samples. Their sequences are indicated under SEQ ID NO. 3 or 6. The derived proteins are designated according to the invention as protease HP70 (for SEQ ID NO. 3 and 4) or HP53 (for SEQ ID NO. 6 and 7). As can be comprehended with the aid of alignment, for example by means of FIG. 4, they have a homology to one another at the amino acid level of 93.9%.

An extracellular serine protease (E.C. 3.4.21.-) from *Xanthomonas campestris* pv. *campestris* (ATCC 33913), having GenBank (National Center for Biotechnology Information NCBI, National Institutes of Health, Bethesda, Md., USA) accession number NP_636242 is the most similar to the enzymes described herein. Another similar enzyme is an extracellular serine protease (E.C. 3.4.21.-) from *Xanthomonas campestris* pv. *campestris* (ATCC 33913), which in GenBank (National Center for Biotechnology Information NCBI, National Institutes of Health, Bethesda, Md., USA) carries the accession number NP_636242. The homology of this enzyme, determined like all subsequent homology values by means of the computer program Vector NTI® Suite 7.0, obtainable from InforMax, Inc., Bethesda, USA, using the specified default parameters is, at the amino acid level, 75.0% identity to HP70 and 75.4% identity to HP53.

Other similar enzymes are compiled in Examples 4 and 5 in tabular form; they are each extracellular proteases from *Xanthomonas campestris* and *X. axonopodis*. A homology of 26.2% identity and at the nucleotide level of 33.6% results in the established *B. lentus* alkaline protease (WO 92/21760 A1) over the entire length of the alkaline protease HP70 at the amino acid level. HP53 has homology values of 25.9% and 33.5% identity to the *B. lentus* alkaline protease.

These data compiled according to the Examples can be updated in the following way. The protease StmPr2 from *St. maltophilia*, (GenBank: AY253983) has a sequence homology of 84.7% to the protease HP70 according to the invention (SEQ ID NO. 4) and of 82.5% identity to HP53 (SEQ ID NO. 7). The protease disclosed under SEQ ID NO. 66 in WO 2004/033668 A2 is 83.1% identical to HP70 and 81.1% identical to HP53. Compared to the protease disclosed under SEQ ID NO. 70 in WO 2004/033668 A2, homology values of 85.0% identity to HP70 and of 82.3% identity to HP53 result.

Alkaline proteases within the scope of the invention are encoded by SEQ ID NO. 4, or sequences which are at least 90% identical thereto, SEQ ID NO. 7 or sequences which are at least 87.5% identical thereto.

Among these, functional alkaline proteases are preferred.

Increasingly preferred are all alkaline proteases of this type whose amino acid sequences are identical to the amino acid sequence indicated in SEQ ID NO. 4 to at least 95% and increasingly preferably to at least 96%, 97%, 98%, 99% and very particularly preferably to 100% identical or to the amino acid sequence indicated in SEQ ID NO. 7, including sequences which are at least 90% and increasingly preferably to at least 91%, 92%, 93%, 94%, 95%, 96%, 97%, 98%, 99% and very particularly preferably to 100% identical thereto where in each case all integral or fractional intermediate values are correspondingly included.

The associated vectors described in the examples, coding for the proteins which are derived from the vector shown in FIG. 3, were given the designations 70-pUC(AWB403) for HP70 and 53-pUC(AWB403) for HP53. They were deposited under this name on Oct. 2, 2003 at the Deutsche Sammlung von Mikroorganismen and Zellkulturen GmbH, Mascheroder Weg 1b, 38124 Brunswick and there carry the deposit numbers DSM 15977 and DSM 15976 respectively. The respective viability was confirmed by the DSMZ on Oct. 17, 2003. The proteases encoded by these vectors, investigated in the examples of the present application and therefore most strongly preferred, are designated as HP70 and HP53 respectively.

Those alkaline proteases according to the invention also encompass fragments of the sequences which correspond to the amino acid positions 33 to 581 as in SEQ ID NO. 4 or 39 to 586 as in SEQ ID NO. 7.

The mature protein is included above as the mature forms exert the industrially relevant functions. Currently, it still cannot be said without doubt which amino acid in each case represents the N-terminus of the mature protein. At the present time, the beginning in positions 33 or 39 only appears most probable. Should it turn out at a later point in time that other amino acids represent the respective N-terminus, the claimed field of protection will be based thereon, where the position mentioned in each case designates the first amino acid of the mature protein.

A sequence comparison of these mature enzymes carried out as in example 4 with the nearest similar ones from the prior art has yielded the following result: the (presumably) mature protease HP70 (SEQ ID NO. 4, positions 33 to 581) is identical to the homologous region of SEQ ID NO. 66 from WO 2004/033668 A2 to 84.2%, to that of SEQ ID NO. 70 from WO 2004/033668 A2 to 86.2% and to that of the protease STmPr2 to 85.8%. The (presumably) mature protease HP53 (SEQ ID NO. 7, positions 39 to 586) is identical to the homologous region of SEQ ID NO. 66 from WO 2004/

033668 A2 to 83.8%, to that of SEQ ID NO. 70 from WO 2004/033668 A2 to 85.0% and to that of the protease STmPr2 to 85.2%.

The same applies for the C-terminus. At present, positions 581 and 586 as in SEQ ID NO. 4 and 7 appear to be the C-termini, because the nucleotide positions 1744 to 1746 as in SEQ ID NO. 3 and the positions 1759 to 1761 as in SEQ ID NO.6 in each case represent a stop codon. Should it turn out at a later point in time, however, that as a result of processing another amino acid represents the C-terminus of the mature, active protein, the claimed scope of protection will be related thereto, where the numbers indicated in each case designate the last amino acid of the mature, active protein. In principle, the same applies for the case where on maturation of the protein internal fragments are possibly excised. The amino acid sequence of the mature, active protein is in each case particularly preferred.

Any of the alkaline proteases described up to now is furthermore preferred in which the homology values from at least 90% identity in each case apply for the region which corresponds to the amino acid positions 33 to 470 as in SEQ ID NO. 5 or 33 to 470 as in SEQ ID NO. 8.

As is described in the Examples, the C-terminal regions mentioned therein and hereby excluded from the preferred scope of protection could be deleted both from HP70 and from HP53 without the deletion variants losing their protease activity, in particular, the proteolytic activity needed during the washing or cleaning process. The advantage in this drastic deletion consists in the saving of expenditure and costs in the biotechnological preparation of the proteins concerned. Thus, in a shorter time more enzymes usable according to the invention, particularly for use in detergents and cleaners, are obtained, which is also accompanied, for example, by a better utilization of the media constituents necessary for the fermentation of the producing microorganisms.

A sequence comparison of these mature and C-terminally deleted enzymes with the nearest similar ones from the prior art carried out as in Example 4 has yielded the following result: the (presumably) mature and C-terminally deleted protease HP70 (SEQ ID NO. 5, positions 33 to 470) is identical to the homologous region of SEQ ID NO. 66 from WO 2004/033668 A2 to 85.2%, to that of SEQ ID NO. 70 from WO 2004/033668 A2 to 88.1% and to that of the protease STmPr2 to 87.7%. The (presumably) mature and C-terminally deleted protease HP53 (SEQ ID NO. 8, positions 33 to 470) is identical to the homologous region of SEQ ID NO. 66 from WO 2004/033668 A2 to 85.4%, to that of SEQ ID NO. 70 from WO 20041033668 A2 to 87.0% and to that of the protease STmPr2 likewise to 87.0%.

Any of the alkaline proteases described up to now having an amino acid sequence as in the consensus sequence of SEQ ID NO. 9, preferably in the range of the amino acid positions 39 to 587, particularly preferably in the range of the amino acid positions 39 to 476, is furthermore preferred.

SEQ ID NO. 9 represents the consensus sequence obtainable from the two amino acid sequences SEQ ID NO. 4 and 7, as can be established, for example, by means of the alignment of FIG. 4. It comprises those proteases whose amino acid sequences in each of their position can be traced back either to SEQ ID NO. 4 or SEQ ID NO. 7. These two sequences thus provide sequence information for subtilisin proteases related to or similar to one another. They have the general sequence indicated in SEQ ID NO. 9, where in the following 35 positions two different amino acids in each case can be present or a certain amino acid (indicated in the three-letter code) or no (—) amino acid; to be precise the following possibilities (in the sequence protocol in each case defined as a "variant"): position 2: — or Ile, position 3: Ser or Thr, position 4: His or Asn, position 5: Asp or Ser, position 7: — or Ser, position 8: — or Val, position 9: — or Pro, position 10: — or Gly, position 11: — or Asp, position 12: Gln or Pro, position 13: Pro or Gin, position 25: Ala or Gly, position 48: Ser or Ala, position 65: Asn or Thr, position 66: Leu or Asp, position 82: Ser or Gin, position 149: Ala or Ser, position 234: Ser or Ala, position 236: Ile or Tyr, position 259: Ser or Thr, position 267: Phe or Tyr, position 321: Thr or Ser, position 386: Ile or Val, position 406: Thr or Ala, position 438: Thr or Ser, position 487: Thr or —, position 488: Val or Thr, position 501: Ala or Ser, position 507: Ser or Ala, position 511: Val or Ala, position 522: Ser or Thr, position 527: Ser or Thr, position 546: Asn or Thr, position 562: Ser or Ala and, finally, position 574: Gly or Ala.

Since the two enzymes HP70 and HP53 in the investigations documented by the present examples have advantages according to the invention and moreover agree to 93.9%, it is to be expected that each further enzyme which belongs to this protease subfamily has comparably favorable properties.

This applies correspondingly to what has been said above, in particular for the parts of the in each case mature, that is active, enzyme and very particularly for those deletion variants in which large parts of the C-terminus are removed without noticeable loss of the protease activity.

Each of the alkaline proteases described up to now is furthermore preferred which is encoded by a nucleotide sequence which is identical to the nucleotide sequence indicated in SEQ ID NO. 3 at least to 85% and increasingly preferably to at least 90%, 95%, 96%, 97%, 98%, 99% and very particularly preferably to 100%, in particular for the region corresponding to nucleotide positions 97 to 1746 as in SEQ ID NO. 3, very particularly for the region corresponding to nucleotide positions 97 to 1410 as in SEQ ID NO. 3, or which is encoded by a nucleotide sequence which is identical to the nucleotide sequence indicated in SEQ ID NO. 6 at least to 85% and increasingly preferably to at least 90%, 95%, 96%, 97%, 98%, 99% and very particularly preferably to 100%, in particular for the region which corresponds to the nucleotide positions 115 to 1761 as in SEQ ID NO. 6, very particularly for the region corresponding to nucleotide positions 115 to 1428 as in SEQ ID NO. 6, where in each case all integral or fractional intermediate values are correspondingly included.

As is explained in examples 3 and 4, the nearest similar enzyme to HP70 and HP53 at the nucleotide level, an extracellular serine protease (E.C. 3.4.21.-) from *Xanthomonas campestris* pv. *campestris* (ATCC 33913; NP_636242), as can be determined by means of the computer program Vector NTI® Suite 7.0, obtainable from InforMax, Inc., Bethesda, USA, using the specified default parameters, has a homology of 74.4 or 75.0% identity at the nucleotide level. Accordingly, all alkaline proteases and proteins which are encoded by significantly more similar nucleic acids are included in the scope of protection.

These data compiled according to the examples can be updated in the following way: The protease StmPr2 from *St. maltophilia*, (GenBank: AY253983) has a sequence homology of 80.8 at the DNA level to the protease HP70 according to the invention (SEQ ID NO. 3) in the homologizable region and to the DNA sequence of HP53 (SEQ ID NO. 6) of 81.2% identity. The protease DNA sequence disclosed under SEQ ID NO. 65 in WO 2004/033668 A2 is identical to that of HP70 to 79.6% and to that of HP53 to 79.9%. In comparison to the protease-encoding DNA sequence disclosed under SEQ ID NO. 69 in WO 2004/033668 A2, homology values of 81.3% identity to the HP70 DNA and of 81.1% identity to the HP53 DNA result.

The statements up to now apply correspondingly particularly for the nucleic acid sequences which code for the mature proteins and very particularly for the C-terminally deleted, proteolytically active variants thereof. These are the enzymes whose proteolytic activities and in particular whose contributions to the washing or cleaning performance of corresponding formulations are covered in the examples of the present application.

A sequence comparison of these DNA sections coding for the mature enzymes carried out as in example 4 with the nearest similar ones from the prior art has yielded the following result: the gene for the (presumably) mature protease HP70 (SEQ ID NO. 3, positions 97 to 1746) is identical to the homologous region of SEQ ID NO. 65 from WO 2004/033668 A2 to 80.0%, to that of SEQ ID NO. 69 from WO 2004/033668 A2 to 81.8% and to that of the protease STmPr2 to 81.3%. The gene for the (presumably) mature protease HP53 (SEQ ID NO. 6, positions 115 to 1761) is identical to the homologous region of SEQ ID NO. 65 from WO 2004/033668 A2 to 81.0%, to that of SEQ ID NO. 69 from WO 2004/033668 A2 to 82.2% and to that of the protease STmPr2 to 82.9%.

The alkaline proteases derived therefrom are accordingly preferred.

A further sequence comparison of the DNA sections encoding for these mature and C-terminally deleted enzymes is provided in example 4 with the closest similar ones from the prior art yielding the following result: the gene for the (presumably) mature and C-terminally deleted protease HP70 (SEQ ID NO. 3, positions 97 to 1410) is identical to the homologous region of SEQ ID NO. 65 from WO 2004/033668 A2 to 81.4%, to that of SEQ ID NO. 69 from WO 2004/033668 A2 to 83.7% and to that of the protease STmPr2 to 83.2%. The nucleic acid encoding for the (presumably) mature and C-terminally deleted protease HP53 (SEQ ID NO. 6, positions 115 to 1428) is identical to the homologous region of SEQ ID NO. 65 from WO 2004/033668 A2 to 82.1%, to that of SEQ ID NO. 69 from WO 2004/033668 A2 to 83.6% and to that of the protease STmPr2 to 83.9%.

The alkaline proteases encoding from these DNA sections are accordingly particularly preferred.

Furthermore, each of the alkaline proteases according to the invention described up to now, which is isolable from a natural habitat or which is derived from a nucleic acid isolable from a natural habitat, is preferred.

It is to be assumed that the DNAs isolated using the method described in the examples have been formed from natural organisms and also code in vivo for functional proteins. Thus, the associated enzymes themselves must also be able to be found by means of analogous methods, in particular if they are not pseudogenes but actually formed proteins. On the other hand, the isolation of the nucleic acids leads immediately to a gene which can be introduced into molecular biological characterizations and produced. Moreover, it cannot always be expected that the genes concerned are expressed under all conditions, so that nontranslated genes are also instantly accessible by means of the nucleic acid isolation.

Furthermore, each of the alkaline proteases according to the invention described up to now, which itself or whose associated nucleic acid originates from an organism which is isolable from a natural habitat, is preferred.

This embodiment is therefore particularly advantageous, because then the associated organism itself can be taken into culture. Advantageously, the proteases according to the invention can then be isolated and prepared from its cell extracts or culture supernatants.

Among these, those alkaline proteases are preferred where a microorganism is involved, preferably a fungus or a bacterium, among these preferably a gram-positive bacterium and particularly preferably one of the genus *Bacillus*.

Particularly for these organisms, culture methods are known and established in the prior art. This applies in particular for Bacilli, which take up an outstanding role in industrial enzyme production. Those alkaline proteases and proteins which originate from *Xanthomonas* species are a further embodiment. From one of these gram-negative species originate the known enzymes determined as the nearest similar ones (see above); there is also already experience in the biotechnological fermentation of xanthomonads.

Alkaline proteases derived from one of the alkaline proteases according to the invention described up to now by fragmentation or deletion mutagenesis or proteins having at least 100 and increasingly preferably at least 150, 200, 250 and very particularly preferably at least 300 amino acids already connected in the starting molecule are furthermore preferred.

Thus it is possible, for example, to delete individual amino acids at the termini or in the loops of the enzyme without the proteolytic activity being lost as a result. Such mutations are described, for example, in WO 99/49057 A1. WO 01/07575 A2 teaches that by means of such deletions the allergenicity of proteases can be lowered and thus overall their employability can be improved. The fragmentation works to the advantage of the insertion or substitution mutagenesis and/or fusion carried out later with other enzymes. With respect to the intended use of these enzymes, it is preferred if they also have a proteolytic activity after fragmentation or deletion mutagenesis; it is particularly preferred if they have an activity additionally increased hereby.

Alkaline proteases or proteins as have been previously described as according to the invention and are derived from one of the alkaline proteases or proteins described up to now by insertion mutagenesis, by substitution mutagenesis and/or by fusion with at least one other protein are furthermore preferred.

Numerous documents from the prior art disclose advantageous effects of insertions and substitutions in proteases; among them also said publications WO 99/49057 A1 and WO 01/07575 A2. In principle, these also include individual replacements of amino acids; however, a number of connected amino acids can also be replaced by others. These also include novel combinations of relatively large enzyme sections, that is the above-mentioned fragments, with other proteases or proteins of other function. Thus it is possible, for example, following WO 99/57254 A1, to provide a protein according to the invention or parts thereof via peptide linkers or directly as a fusion protein with binding domains from other proteins, for example the cellulose binding domain, and as a result to make the hydrolysis of the substrate more effective. Likewise, proteins according to the invention can, for example, also be linked with amylases or cellulases to exert a dual function.

Among these, the alkaline proteases or proteins having one or more amino acid replacements in the positions 3, 4, 36, 42, 47, 56, 61, 69, 87, 96, 99, 101, 102, 104, 114, 118, 120, 130, 139, 141, 142, 154, 157, 188, 193, 199, 205, 211, 224, 229, 236, 237, 242, 243, 255 and 268 in the numbering of the alkaline protease from *Bacillus lentus* are preferred, where these positions are to be assigned by means of the alignment in FIG. 1.

Here, the following amino acid residues lie in the wild-type molecule of the *B. lentus* alkaline protease: S3, V4, S36, N42, A47, T56, G61, T69, E87, A96, R99, A101, I102, S104, N114, H118, A120, S130, S139, T141, S142, S154, S157, A188, V193, V199, G205, L211, A224, K229, S236, N237, N242, H243, N255 and T268.

Since, in addition to the alkaline protease from *Bacillus licheniformis*, the *B. lentus* alkaline protease in the prior art is an important reference molecule for the description of novel proteases and of point mutations, the novel protease described here and thus also its sequence were unknown up to now, it appears advantageous to refer to this numbering in the assignment of the point mutations. On the other hand, the numbering in general depends on the mature protein, and as mentioned above it is still not definite at the present point in time with which amino acid the mature protein begins. In the numbering of SEQ ID NO. 4 (HP70), these positions—as can be understood by means of FIG. 1—correspond to the following position numbers: P140, N141, T182, N188, Y195, A204, G209, T245, K264, K273, (−), Y277, T278, D280, V296, E304, I306, S317, G326, V328, S329, S341, V345, A376, S381, S393, G399, Y406, V419, Q424, T432, P433, T438, L439, G453 and V466.

In the numbering of SEQ ID NO. 7, that is HP53, these are the following positions: P146, N147, T188, N194, Y201, A210, G215, T251, K270, K279, (−), Y283, T284, D286, V302, E310, I312, S323, G332, V334, S335, S347, V351, A382, S387, S399, G405, Y412, V425, Q430, S438, P439, T444, L445, G459 and V472.

Thus, from the application WO 92/21760 A1 single and multiple variants of the subtilisin from *Bacillus lentus* DSM 5483 in the following positions follow: 3, 4, 36, 42, 47, 56, 69, 87, 96, 101, 102, 104, 114, 118, 120, 130, 139, 141, 142, 157, 188, 193, 199, 205, 224, 229, 236, 237, 242, 243, 255 and 268. The application WO 95/23221 A1 additionally discloses replacements in this molecule in positions 99, 154 and 211, in particular R99G, R99A, R99S, S154D, S154E, L211D and L211E. On account of the application WO 95/07770 A1, such variants are particularly also suitable for use in cosmetics. In addition to other replacements, the replacement L211G is also described in the application WO 02/088340 A2, and the replacement G61A in WO 03/038082 A2.

Among these, accordingly those are preferred in which the further amino acid replacements are present in one or more of the positions 3, 4, 61, 188, 193, 199 and 211. In HP70, the positions P140, N141, G209, A376, S381, S393 and Y406 correspond to this and in HP53 the positions P146, N147, G215, A382, S387, S399 and Y412.

Among these, corresponding to what has been said above, those are in turn preferred which are one or more of the amino acid replacements 3T, 4I, 61A, 188P, 193M, 199I and 211D or 211G, providing the correspondingly homologous positions are not already naturally taken by one of these preferred amino acids.

The replacements S3T and V4I lead, as is explained in particular in WO 02/088340 A2, presumably by means of a stabilizing effect to the molecule, to an improvement of its contribution to the washing performance of a detergent or cleaner. The replacements S3T, V4I, A188P, V193M, V199I and L211D characterize the protease designated as F49 according to WO 95/23221 A1, which has been used in Examples 7 and 8 of the present application as an efficient comparison enzyme established in the prior art. On the other hand, the proteases HP70 and HP53 are still unmodified wild-type molecules, whose activity, in particular their contribution to the washing performance, might be improved by these same replacements.

An alkaline protease according to the invention described beforehand or such a protein which is additionally stabilized is further preferred.

An increase in stability during storage and/or during use, for example in the washing process, leads to its activity lasting longer and thus being increased in action. As stabilization possibilities, all strategies which are described and expedient in the prior art are suitable, for example, according to U.S. Pat. No. 5,230,891, covalent coupling to a polymer.

Stabilizations are preferred which are possible by means of point mutagenesis of the molecule itself. These necessitate, following the protein recovery, no further working steps. Some point mutations suitable for this are known per se from the prior art. Thus, according to U.S. Pat. Nos. 6,087,315 and 6,110,884, proteases can be stabilized by replacing certain tyrosine residues for others.

Further possibilities are, for example:
modification of the binding of metal ions, in particular of the calcium binding sites, for example according to the teaching of the applications WO 88/08028 A1 and WO 88/08033 A1; according to the first of these specifications one or more of the amino acid residues involved in the calcium binding must be replaced by negatively charged amino acids; according to the teaching of the application WO 88/08033, for stabilization by means of the calcium binding, point mutations must be introduced simultaneously into at least one of the sequences of the two radicals arginine/glycine;
according to the U.S. Pat. No. 5,453,372, proteins can be protected against the influence of denaturing agents such as surfactants by certain mutations on the surface.

Another possibility for stabilization with regard to increased temperature and the action of surfactants would be, in application of the teaching of WO 92/21760 A1, WO 02/088340 A2 and WO 03/038082 A2, stabilization by means of the replacement of amino acids which lie near the N-terminus by those which presumably come into contact with the remainder of the molecule by means of noncovalent interactions and thus make a contribution to the maintenance of the globular structure. This is in particular advisable for alkaline proteases which have originally been obtained as *B. lentus*. Appropriate mutants having the variants as in SEQ ID NO. 12 and 16 are described in the examples of the present application.

Preferred embodiments are those in which the molecule is stabilized in a number of ways. For example, according to WO 89/09819 A1 it can be assumed that a number of stabilizing mutations act additively.

An alkaline protease according to the invention described beforehand or such a protein which is additionally derivatized is further preferred.

Derivatives are understood as meaning those proteins which are derived by means of an additional modification of the proteins produced. Such modifications can, for example, influence the stability, substrate specificity or the binding strength to the substrate or the enzymatic activity. They can also serve to reduce the allergenicity and/or immunogenicity of the protein and thus, for example, to increase its skin compatibility.

Such derivatizations can be carried out, for example, biologically, for example in connection with the protein biosynthesis by the producing host organism. Here, couplings of low molecular weight compounds such as of lipids or oligosaccharides are particularly to be emphasized.

Derivatizations, however, can also be carried out chemically, for example by the chemical conversion of a side chain or by covalent bonding of another, for example macromolecular, compound to the protein. A chemical modification is described, for example, in the application DE 4013142 A1. For example, the coupling of amines to carboxyl groups of an enzyme for the modification of the isoelectric point follows from WO 95/26398 A1. For example, macromolecules such as proteins can be bonded to proteins according to the invention, for example by means of bifunctional chemical compounds. For example, using the teaching of WO 99/57154 A1 it is possible to provide a protein according to the invention with a specific binding domain also by means of a non-protein linker. Such derivatives are particularly suitable for use in detergents or cleaners. Analogously to WO 00/01831 A2, protease inhibitors can also be bonded to the proteins according to the invention via linkers, in particular amino acid linkers. Couplings with other macromolecular compounds, such as, for example, polyethylene glycol, improve the molecule with respect to further properties such as stability or skin compatibility; this has already been explained.

Derivatives of proteins according to the invention can in the widest sense also be understood as meaning preparations of these enzymes. Depending on obtainment, workup or preparation, a protein can be associated with various other substances, for example from the culture of the producing microorganisms. A protein can also have been treated, for example for increasing its storage stability, specifically with certain other substances. All preparations of a protein according to the invention are therefore also according to the invention. This is also independent of whether it actually displays this enzymatic activity or not in a certain preparation. It can be desirable that during storage it has no or only low activity, and only displays its proteolytic function at the time of use. This can be controlled, for example, by means of appropriate concomitant substances. In particular, the joint preparation of proteases with protease inhibitors is advantageous and is known from the prior art (WO 00/01826 A2).

An alkaline protease according to the invention described beforehand or such a protein which has at least one antigenic determinant in common with one of the alkaline proteases or proteins designated beforehand, in particular over at least one of the epitope regions within which the positions 3, 4, 36, 42, 47, 56, 61, 69, 87, 96, 99, 101, 102, 104, 114, 118, 120, 130, 139, 141, 142, 154, 157, 188, 193, 199, 205, 211, 224, 229, 236, 237, 242, 243, 255 and 268 lie in the numbering of the alkaline protease from *Bacillus lentus*, to be assigned by means of the alignment in FIG. 1, is further preferred.

This applies in particular for the variants in these positions described above, since on the one hand they are preferred per se and on the other hand they can be differentiated by means of antibodies which have been specifically formed against these regions from the proteases which agree in these positions with the wild-type molecule.

The achievement of a subtask and thus an independent subject of the invention are nucleic acids having a nucleotide sequence which is identical to the nucleotide sequence indicated in SEQ ID NO. 3 at least to 85% or to the nucleotide sequence indicated in SEQ ID NO. 6 at least to 85%.

On the one hand, the detection of the protease described in the examples is based on the isolation of the associated DNA. On the other hand, the nucleic acids can be immediately cloned and thus incorporated into the recombinant DNA production of the directed enzymes.

Among these, those are increasingly preferred which are identical to one of the indicated nucleotide sequences increasingly preferably to at least 87.5%, 90%, 91%, 92%, 93%, 94%, 95%, 96%, 97%, 98%, 99% and very particularly preferably to 100%, where in each case all integral or fractional intermediate values are included.

Corresponding to the remarks made above and as is described in the examples, as the nearest similar nucleotide sequences to SEQ ID NO. 3 and SEQ ID NO. 6 only those having 74.4% and 75.0% identity could be found in the prior art.

The further DNA sequences following from WO 2004/033668 A2 and the GenBank entry AY253983 have already been discussed above and are sufficiently different to the nucleotide sequences according to the invention described here.

Those nucleic acids according to the invention in which the homology values in each case apply for the region which corresponds to the nucleotide positions 97 to 1746 as in SEQ ID NO. 3 or to the nucleotide positions 115 to 1761 as in SEQ ID NO. 6 are further-more preferred.

Corresponding to what has been said above, the region is hereby meant which codes for the in each case mature, that is active, protein. The stop codon is also included because its existence makes sure that a larger possibly no longer functional, unintentional fusion protein is not formed. Thus, in the cloning, care is to be taken that a stop codon likewise lies in this position, if a protein fusion is not specifically to be caused by means of the C-terminus. Should it later turn out that the mature protein is formed from another part of this sequence, the scope of protection correspondingly applies for this part.

Those nucleic acids according to the invention are furthermore preferred in which the homology values in each case apply for the region which corresponds to the nucleotide positions 97 to 1410 as in SEQ ID NO. 3 or to the nucleotide positions 115 to 1428 as in SEQ ID NO. 6.

As is described in the examples, it suffices in the case of the proteins HP70 and HP53 to use the N-terminal part of the total protein; a considerable C-terminal deletion in both cases led to an enzyme proteolytically active in detergents and cleaners, which has provided a corresponding contribution to the total cleaning performance of the composition concerned. Nucleic acids which code for such variants are therefore preferred embodiments, because they make possible a more cost-efficient biotechnological preparation of the proteins concerned.

Furthermore and corresponding to the previous remarks, those nucleic acids according to the invention are preferred which code for an alkaline protease or a protein of the first subject of the invention.

The same proteins should be made available by the present application, so that nucleic acids which code for only inactive proteins are not a solution according to the invention. Those nucleic acids which code for mature proteins are preferred and, increasingly particularly, those which code for increasingly more active variants.

Those nucleic acids according to the invention of which one or preferably more codons are replaced by synonymous codons are furthermore preferred.

This aspect relates in particular to the heterologous expression of the proteases concerned. Thus each organism, in particular each production strain has a certain codon usage. Here, bottlenecks in the protein biosynthesis can occur if the codons lying on the transgenic nucleic acid in the host cell are opposite to a comparatively small number of loaded tRNAs. Synonymous codons code, on the other hand, for the same amino acids and can be better translated, depending on the host. This optionally necessary transcription thus depends on the choice of the expression system. In particular with samples from unknown, possibly not culturable organisms, a corresponding adjustment may be necessary.

Corresponding to the remarks made above, the cells of an organism in the scope of protection are furthermore included and are an individual subject of the invention, which naturally contains a nucleic acid according to the invention.

By means of their culturing, the desired enzymes can be directly accessible.

Particularly preferred among these are those cells which naturally express and preferably secrete a protease or a protein of the first subject of the invention.

By means of this, proteases according to the invention can be immediately tested with respect to their intended area of application and possibly obtained in relatively large amounts by immediate culturing of this organism.

Among these, in turn, those cells are preferred which are microorganisms, preferably fungi or bacteria, among them preferably gram-positive bacteria and particularly preferably those of the genus *Bacillus* or gram-negative bacteria of the genus *Xanthomonas*.

With microorganisms, there has been in the prior art extensive experience with respect to the molecular biological techniques and the production. This applies particularly for gram-positive bacteria, of which those of the genus *Bacillus* belong to the most familiar production strains. No less preferred, however, are gram-negative bacteria of the genus *Xanthomonas*, which up to now were utilized in particular for the production of the extracellular polysaccharide xanthan. On account of the homology comparisons already discussed and shown in the examples, it moreover appears possible that strains of this genus naturally produce the particularly preferred proteases according to the invention HP70 and HP53. At least, their production in closely related strains should be particularly advantageously realizable, for example as far as their codon usage is concerned.

A further independent subject of the invention are methods for the identification of an alkaline protease of the first subject of the invention, which are based on the isolation of a nucleic acid from a naturally colonized habitat.

As is confirmed by the present invention, for the identification of novel proteases it is not absolutely necessary also to isolate the proteases and microorganisms concerned from nature. In particular by means of shotgun cloning or alternatively by means of PCR primers for known sequence motifs it is possible to discover the nucleic acids concerned directly. Such a method is presented in examples 1 to 3 of the present application. Accordingly, it is possible, for example, to culture the microorganism flora of soil samples, to isolate DNA therefrom and by means of cloning in an expression vector to test for protease expression.

Among said methods, those are preferred in which one, preferably two, oligonucleotides corresponding to one another are employed, which can serve as PCR primers and are derived from one of the two sequences SEQ ID NO. 3 or 6.

A comparable approach based on a PCR using suitable primers follows, for example, from the application WO 03/002711 A2 in the example of α-amylases. Thus, it is possible, instead of culturing the microorganisms and preparing the DNA therefrom, directly to amplify the nucleic acids contained in a soil sample. For this, PCR-based approaches are suitable. In this case, the nucleotide sequences indicated under SEQ ID NO. 3 and 6 can serve as a prototype for the design of corresponding PCR primers. It is advantageous here to design primers according to methods known per se, which exclusively or in particular N-terminal comprise only little more than the mature protein; moreover, the knowledge obtained on the dc variants (Example 6) can be utilized to the effect that by means of the PCR only nucleic acids coding for correspondingly truncated proteins are amplified.

Furthermore, those methods are preferred in which the isolated nucleic acid is cloned, preferably expressed and particularly preferably identified as a protease by means of the protease activity of the expression product.

Cloning usually represents, even if a PCR has not been carried out beforehand, the essential molecular biological step by which the obtainment of the associated enzyme is initiated. Expression serves for the biochemical characterization of the protein derived from the nucleic acid. In particular, if the test for protease activity, for example by means of the degradation of a protein substrate (compare examples) is successful, it is possible to be certain to have found a protease, which can be investigated in subsequent tests with respect to its industrial usability.

A further independent subject of the invention are vectors which contain a nucleic acid region according to the invention designated beforehand.

In order to deal with the nucleic acids relevant to the invention, and thus in particular to prepare for the production of proteins according to the invention, they are suitably ligated in vectors. Such vectors and the associated working methods are described in detail in the prior art. Vectors are commercially obtainable in great number and variation width, both for cloning and for expression. These include, for example, vectors which are derived from bacterial plasmids, from bacteriophages or from viruses, or mainly synthetic vectors. Furthermore, they are differentiated by the kind of cell types in which they are able to be established, for example by vectors for gram-negative, for gram-positive bacteria, for yeasts or for higher eukaryotes. They form suitable starting points, for example, for molecular biological and biochemical investigations and for the expression of the gene concerned or associated protein.

In one embodiment, vectors according to the invention are cloning vectors.

Cloning vectors are suitable, in addition to the storage, the biological amplification or the selection of the gene of interest, for its molecular biological characterization. Simultaneously, they are transportable and storable forms of the claimed nucleic acids and are also starting points for molecular biological techniques, which are not tied to cells, such as, for example, the PCR or in vitro mutagenesis methods.

Preferably, vectors according to the invention are expression vectors.

Such expression vectors are the basis for producing the corresponding nucleic acids in biological production systems and therewith producing the associated proteins. Preferred embodiments of this subject of the invention are expression vectors which carry the genetic elements necessary for expression, for example the natural promoter, originally located upstream of this gene, or a promoter from another organism. These elements can be arranged, for example, in the form of an "expression cassette". Alternatively, individual or all regulation elements can also be made available by the respective host cell. Particularly preferably, the expression vectors are matched with respect to further properties, such as, for example, the optimal copy number, with the chosen expression system, in particular the host cell (see below).

An independent subject of the invention are cells which after recombinant DNA modification contain one of the nucleic acid regions according to the invention designated beforehand.

These cells contain the genetic information for the synthesis of a protein according to the invention. Among them, in contrast to the natural producers likewise claimed described above, those cells are meant which according to methods known per se have been provided with the nucleic acids according to the invention, or which are derived from such cells. For this, suitably those host cells are selected which can be cultured comparatively simply and/or produce high product yields.

They make possible, for example, the amplification of the corresponding genes, but also their mutagenesis or transcription and translation and finally the biotechnological production of the proteins concerned. This genetic information can either be present extrachromosomally as a separate genetic element that is in bacteria in a plasmidal location, or integrated into a chromosome. The choice of a suitable system depends on questions such as, for example, the type and duration of the storage of the gene, or of the organism or the type of mutagenesis or selection. For instance, mutagenesis and selection methods for the development of detergent enzymes based on bacteriophages—and their specific host cells—are described in the prior art (WO 97/09446 A1).

In the countries where appropriate national laws demand that human embryonic stem cells are excluded from such an application subject, the present invention is only claimed for a correspondingly restricted subject.

Preferably, said nucleic acid region lies on one of the vectors according to the invention designated above, in particular on a cloning or expression vector.

They hereby become relevant to the realization of the present invention.

Furthermore, those cells are preferred which express, preferably secrete, an alkaline protease or a protein of the first subject of the invention.

Protein-forming host cells make possible their biotechnological production. Suitable host cells for protein expression are in principle all organisms, that is prokaryotes, eukaryotes or Cyanophyta. Those host cells are preferred which genetically can be readily handled, which concerns, for example, the transformation with the expression vector, its stable establishment and the regulation of the expression, for example monocellular fungi or bacteria. Moreover, preferred host cells are distinguished by good microbiological and biotechnological handleability. This relates, for example, to easy culturability, high growth rates, low requirements for fermentation media and good production and secretion rates for foreign proteins. Preferably, laboratory strains are chosen which are oriented to expression. Such strains are obtainable commercially or by means of generally accessible strain collections. Each protein according to the invention can in this way theoretically be obtained from a large number of host organisms. From the abundance of various systems available according to the prior art, the optimal expression systems for the individual case must be determined experimentally.

Host cells are particularly advantageous which are themselves protease-negative and thus do not degrade proteins formed.

Preferred embodiments are those host cells which on account of appropriate genetic elements are regulatable in their activity, for example by controlled addition of chemical compounds, by modification of the culturing conditions or as a function of the respective cell density. This controllable expression makes possible a very economical production of the proteins of interest; it is realizable, for example, by means of an appropriate element on the vector concerned. Suitably, gene, expression vector and host cell are matched to one another, as far as, for example, the genetic elements necessary for expression (ribosome binding site, promoters, terminators) or the codon usage are concerned.

Among these, host cells are preferred which are characterized in that they are bacteria.

Bacteria are distinguished by short generation times and low demands on the culturing conditions. Inexpensive methods can thereby be established. Moreover, we have an extensive wealth of experience with bacteria in fermentation technology. Gram-negative or gram-positive bacteria can be suitable for a special production for the most different reasons, to be determined experimentally in the individual case, such as nutrient sources, product formation rate, time need etc.

In a preferred embodiment, these are gram-negative bacteria, in particular of the genera *Escherichia coli, Klebsiella, Pseudomonas* or *Xanthomonas*, in particular strains of *E. coli* K12, *E. coli* B or *Klebsiella planticola*, and very particularly derivatives of the strains *Escherichia coli* BL21 (DE3), *E. coli* RV308, *E. coli* DH5.alpha., *E. coli* JM109, *E. coli* XL-1 or *Klebsiella planticola* (Rf).

In gram-negative bacteria, such as, for example, *E. coli*, a large number of proteins are secreted into the periplasmatic space. This can be advantageous for special applications. In the application WO 01/81597 A1, a method is disclosed according to which it is achieved that even gram-negative bacteria expel the expressed proteins. Such a system is also suitable for the production of proteins according to the invention. The gram-negative bacteria mentioned as preferred are as a rule accessible easily, that is commercially or by means of public strain collections, and optimizable to specific production conditions in interaction with other components likewise available in large number such as, for example, vectors.

As mentioned above, *Xanthomonas*, but also *Pseudomonas* are, on account of their suspected relationship to the strains producing HP70 and/or HP53 in vivo, promising host cells; not least also because of a presumably similar codon usage.

In an alternative, no less preferred embodiment, these are a gram-positive bacterium, in particular one of the genera *Bacillus, Staphylococcus* or *Corynebacterium*, very particularly of the species *Bacillus lentus, B. licheniformis, B. amyloliquefaciens, B. subtilis, B. globigii* or *B. alcalophilus, Staphylococcus carnosus* or *Corynebacterium glutamicum*.

Gram-positive bacteria have, compared to gram-negative bacteria, the basic difference of releasing secreted proteins immediately into the nutrient medium surrounding the cells, from which, if this is desired, the expressed proteins according to the invention can be purified directly from the nutrient medium. Moreover, they are related or identical to most of the organisms of origin for industrially important subtilisins and usually themselves form comparable subtilisins, so that they have a similar codon usage and their protein synthesis apparatus is naturally accordingly oriented. A further advantage can consist in the fact that by means of this method a mixture of proteins according to the invention can be obtained with the subtilisins formed endogenously from the host strains. Such a coexpression likewise follows from the application WO 91/02792. Should they not be desired, the protease genes naturally present in the host cell must be inactivated permanently or temporarily.

Host cells are further preferred which are eukaryotic cells, preferably of the genus *Saccharomyces*.

Examples of these are fungi such as *Actinomycetes* or simply yeasts such as *Saccharomyces* or *Kluyveromyces*. Thermophilic fungal expression systems are presented, for example, in WO 96/02653 A1. These are particularly suitable for the expression of temperature-resistant variants. The modifications which eukaryotic systems carry out, particularly in connection with protein synthesis, include, for example, the binding of low molecular weight compounds such as membrane anchors or oligosaccharides. Oligosaccharide modifications of this type can be desirable, for example, for lowering the allergenicity. Coexpression with the enzymes naturally formed from cells of this type, such as, for example, cellulases, can also be advantageous.

An independent subject of the invention are methods for the production of an alkaline protease or of a protein according to the first subject of the invention.

This includes all methods for the production of a protein according to the invention described above, for example chemical synthesis methods.

On the other hand, however, all molecular biological, microbiological, or biotechnological preparation methods established in the prior art, already discussed in individual aspects above, are preferred.

Preferably, these are methods which are carried out using a nucleic acid according to the invention designated above, preferably carried out using a vector designated beforehand and particularly preferably using a cell designated beforehand.

By means of said nucleic acids, in particular the nucleic acids indicated in the sequence protocol under SEQ ID NO. 3 or 6, the correspondingly preferred genetic information is made available in microbiologically utilizable form, that is, for recombinant DNA production methods. Provision on a vector particularly successfully utilizable by the host cell or by such cells themselves is increasingly preferred. The production methods concerned are known per se to the person skilled in the art.

On the basis of the associated nucleic acid sequences, embodiments of the present invention can also be cell-free expression systems in which protein biosynthesis in vitro is understood. All elements already mentioned above can also be combined to give novel methods to produce proteins according to the invention. In this case, for each protein according to the invention a large number of combination possibilities of process steps are conceivable, so that optimal processes for each actual individual case have to be determined experimentally.

Corresponding to what has been said above under the cell-associated methods, those are preferred in which the nucleotide sequence has been adapted in one or preferably more codons to the codon usage of the host strain.

An independent subject of the invention are compositions which comprise an alkaline protease according to the invention described above.

Thereby, all types of compositions, in particular mixtures, recipes, solutions etc., whose employability is improved by addition of a protein according to the invention described above, are included in the scope of protection of the present invention. Here, depending on the area of use, these can be, for example, solid mixtures, for example powders containing freeze-dried or encapsulated proteins, or gelatinous or liquid compositions. Preferred recipes contain, for example, buffer substances, stabilizers, reaction partners and/or cofactors of the proteases and/or other ingredients synergistic with the proteases. In particular, among these are to be understood compositions for the use areas mentioned further below. Further use areas follow from the prior art and are presented, for example, in the handbook *Industrial enzymes and their applications* by H. Uhlig, (New York, Wiley-Verlag, 1998).

As a preferred embodiment, compositions are to be included in this subject of the invention which are detergents or cleaners.

As is shown in the working examples of the present application, it was surprisingly possible for detergents and cleaners containing a preferred protease according to the invention to observe a performance increase compared to the protease-free composition.

This subject of the invention includes all conceivable types of cleaners, both concentrates and compositions to be used undiluted, for use on the commercial scale, in a washing machine or a hand wash, or hand cleaning. These include, for example, detergents for textiles, carpets, or natural fibers, for which the designation detergent is used according to the present invention. These also include, for example, washing-up liquids for dishwashers or manual washing-up liquids or cleaners for hard surfaces such as metal, glass, porcelain, ceramic, tiles, stone, lacquered surfaces, plastics, wood or leather; according to the present invention the designation cleaner is used for these.

Embodiments of the present invention include all administration forms established according to the prior art and/or all expedient administration forms of the detergents or cleaners according to the invention. These include, for example, solid, pulverulent, liquid, gelatinous or pasty compositions, optionally also consisting of a number of phases, compressed or uncompressed; and further include, for example: extrudates, granules, tablets or pouches, packed both in large drums and in portions.

In addition to an alkaline protease of the subtilisin type according to the invention, a detergent or cleaner according to the invention optionally contains, according to its area of use, further ingredients such as further enzymes, enzyme stabilizers, surfactants, for example nonionic, anionic and/or amphoteric surfactants, and/or bleaches, and/or builders, and optionally further customary ingredients, which are mentioned in more detail below.

In a preferred embodiment, the detergents or cleaners according to the invention contain the alkaline proteases of the subtilisin type according to the invention described above in an amount from 2 µg to 20 mg, preferably from 5 µg to 17.5 mg, particularly preferably from 20 µg to 15 mg, very particularly preferably from 50 µg to 10 mg per gram of the composition. All integral and nonintegral values in each case lying between these numbers are included.

The protease activity in compositions of this type can be determined according to the method described in *Tenside* [Surfactants], Vol. 7 (1970), pp. 125-132. It is accordingly indicated in PU (protease units).

In the comparison of the performances of two detergent enzymes, as, for example, in the examples of the present application, a distinction must be made between protein-identical and activity-identical use. In particular in the case of recombinantly obtained preparations largely free of additional activity, protein-identical use is appropriate. Thus a statement is possible about whether the same amounts of protein—as a measure of the yield of the fermentative production—lead to comparable results. If the respective ratios of active substance to total protein (the values of the specific activity) diverge, an activity-identical comparison is to be recommended, because by this means the respective enzymatic properties are compared. Generally, it applies that a low specific activity can be compensated by addition of a relatively large amount of protein. This is, in the end, an economic consideration.

A nonexhaustive compilation of important ingredients customary for detergents and cleaners now follows. As an alternative or supplementarily, further ingredients suitable for the respective purpose can be added.

As nonionic surfactants, preferably alkoxylated, advantageously ethoxylated, in particular primary alcohols having preferably 8 to 18 C atoms and on average 1 to 12 mol of ethylene oxide (EO) per mole of alcohol are employed, in which the alcohol radical can be linear or preferably methyl-branched in the 2-position, or can contain linear and methyl-branched residues in the mixture, i.e. as are customarily present in oxoalcohol residues. In particular, however, alcohol ethoxylates having linear residues of alcohols of native origin having 12 to 18 C atoms, for example from coconut, palm, tallow fatty or oleyl alcohol, and on average 2 to 8 EO per mole of alcohol are preferred. The preferred ethoxylated alcohols include, for example, $C_{12-14}$ alcohols having 3 EO or 4 EO, $C_{9-11}$ alcohol having 7 EO, $C_{13-15}$ alcohols having 3 EO, 5 EO, 7 EO or 8 EO, $C_{12-18}$ alcohols having 3 EO, 5 EO or 7 EO and mixtures of these, such as mixtures of $C_{12-14}$ alcohol having 3 EO and $C_{12-18}$ alcohol having 5 EO. The degrees of ethoxylation indicated are statistical mean values, which for a specific product can be an integral or a fractional number. Preferred alcohol ethoxylates have a concentrated homolog distribution (narrow range ethoxylates, NRE). In addition to these nonionic surfactants, also fatty alcohols having more than 12 EO can be employed. Examples of these are tallow fatty alcohol having 14 EO, 25 EO, 30 EO or 40 EO.

A further class of preferably employed nonionic surfactants, which are employed either as a sole nonionic surfactant or in combination with other nonionic surfactants, are alkoxylated, preferably ethoxylated or ethoxylated and propoxylated fatty acid alkyl esters, preferably having 1 to 4 carbon atoms in the alkyl chain, in particular fatty acid methyl esters.

A further class of nonionic surfactants which can be advantageously employed are the alkylpolyglycosides (APG). Employable alkylpolyglycosides satisfy the general formula $RO(G)_z$, in which R is a linear or branched, in particular methyl-branched in the 2-position, saturated or unsaturated, aliphatic radical having 8 to 22, preferably 12 to 18 C atoms and G is the symbol which stands for a glycose unit having 5 or 6 C atoms, preferably for glucose. The degree of glycosylation z here lies between 1.0 and 4.0, preferably between 1.0 and 2.0 and in particular between 1.1 and 1.4. Linear alkylpolyglucosides, that is alkylpolyglycosides in which the polyglycosyl radical is a glucose radical and the alkyl radical is an n-alkyl radical, are preferably employed.

Nonionic surfactants of the amine oxides type, for example N-coconut alkyl-N,N-dimethylamine oxide and N-tallow alkyl-N,N-dihydroxyethylamine oxide, and of the fatty acid alkanolamides type can also be suitable. The content of these nonionic surfactants preferably does not lie above that of the ethoxylated fatty alcohols, in particular is not more than half thereof.

Further suitable surfactants are polyhydroxyfatty acid amides of the formula (II)—

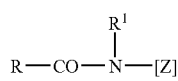

(II)

in which RCO is an aliphatic acyl radical having 6 to 22 carbon atoms, $R^1$ is hydrogen, an alkyl or hydroxyalkyl radical having 1 to 4 carbon atoms and [Z] is a linear or branched polyhydroxyalkyl radical having 3 to 10 carbon atoms and 3 to 10 hydroxyl groups. The polyhydroxyfatty acid amides are known substances, which can customarily be obtained by reductive amination of a reducing sugar with ammonia, an alkylamine or an alkanolamine and subsequent acylation with a fatty acid, a fatty acid alkyl ester or a fatty acid chloride.

The group consisting of the polyhydroxyfatty acid amides also includes compounds of the formula (III)—

(III)

in which R is a linear or branched alkyl or alkenyl radical having 7 to 12 carbon atoms, $R^1$ is a linear, branched or cyclic alkyl radical or an aryl radical having 2 to 8 carbon atoms and $R^2$ is a linear, branched or cyclic alkyl radical or an aryl radical or an oxyalkyl radical having 1 to 8 carbon atoms, where $C_{1-4}$ alkyl or phenyl radicals are preferred and [Z] is a linear polyhydroxyalkyl radical, whose alkyl chain is substituted by at least two hydroxyl groups, or alkoxylated, preferably ethoxylated or propoxylated derivatives of this radical.

[Z] is preferably obtained by reductive amination of a reducing sugar, for example glucose, fructose, maltose, lactose, galactose, mannose or xylose. The N-alkoxy- or N-aryloxy-substituted compounds can be converted, for example, to the desired polyhydroxyfatty acid amides by reaction with fatty acid methyl esters in the presence of an alkoxide as a catalyst.

Anionic surfactants employed are, for example, those of the type consisting of the sulfonates and sulfates. Possible surfactants of the sulfonate type are in this case preferably $C_{9-13}$ alkylbenzenesulfonates, olefinsulfonates, that is, mixtures of alkene- and hydroxyalkanesulfonates and disulfonates such as are obtained, for example, from $C_{12-18}$ monoolefins having a final or internal double bond by sulfonation with gaseous sulfur trioxide and subsequent alkaline or acidic hydrolysis of the sulfonation products. Also suitable are alkanesulfonates which are obtained from $C_{12-18}$ alkanes, for example, by sulfochlorination or sulfoxidation with subsequent hydrolysis or neutralization. Likewise, the esters of α-sulfofatty acids (ester sulfonates), for example the α-sulfonated methyl esters of the hydrogenated coconut, palm kernel or tallow fatty acids, are also suitable.

Further suitable anionic surfactants are sulfated fatty acid glycerol esters. Fatty acid glycerol esters are to be understood as meaning the mono-, di- and triesters and their mixtures, as are obtained in the preparation by esterification of a monoglycerol having 1 to 3 mol of fatty acid, or in the transesterification of triglycerides having 0.3 to 2 mol of glycerol. Preferred sulfated fatty acid glycerol esters here are the sulfation products of saturated fatty acids having 6 to 22 carbon atoms, for example capric acid, caprylic acid, caproic acid, myristic acid, lauric acid, palmitic acid, stearic acid or behenic acid.

Preferred alk(en)ylsulfates are the alkali metal and in particular the sodium salts of the sulfuric acid hemiesters of the $C_{12}$-$C_{18}$ fatty alcohols, for example of coconut fatty alcohol, tallow fatty alcohol, lauryl, myristyl, cetyl or stearyl alcohol or the $C_{10}$-$C_{20}$ oxo alcohols and those hemiesters of secondary alcohols of these chain lengths. Furthermore preferred are alk(en)ylsulfates having said chain length, which contain a synthetic straight-chain alkyl radical, prepared on a petrochemical basis, which have an analogous breakdown behavior to the adequate compounds based on fatty chemical raw materials. From laundry technology interest, the $C_{12}$-$C_{16}$ alkyl sulfates and $C_{12}$-$C_{15}$ alkyl sulfates and $C_{14}$-$C_{15}$ alkyl sulfates are preferred. 2,3-Alkyl sulfates are also suitable anionic surfactants.

The sulfuric acid monoesters of the straight-chain or branched $C_{7-21}$ alcohols ethoxylated with 1 to 6 mol of ethylene oxide, such as 2-methyl-branched $C_{9-11}$ alcohols having on average 3.5 mol of ethylene oxide (EO) or $C_{12-18}$ fatty alcohols having 1 to 4 EO, are also suitable. They are employed only in relatively small amounts in cleaners on account of their high foam behavior, for example in amounts up to 5% by weight, customarily from 1 to 5% by weight.

Further suitable anionic surfactants are also the salts of alkylsulfosuccinic acid, which are also designated as sulfosuccinates or as sulfosuccinic acid esters, and the monoesters and/or diesters of sulfosuccinic acid with alcohols, preferably fatty alcohols and in particular ethoxylated fatty alcohols. Preferred sulfosuccinates contain $C_{8-18}$ fatty alcohol radicals or mixtures of these. In particular, preferred sulfosuccinates contain a fatty alcohol radical, which is derived from ethoxylated fatty alcohols, which considered per se are nonionic surfactants (for description see above). Here, in turn, sulfosuccinates whose fatty alcohol radicals are derived from ethoxylated fatty alcohols having a concentrated homolog distribution are particularly preferred. Likewise, it is also possible to employ alk(en)ylsuccinic acid preferably having 8 to 18 carbon atoms in the alk(en)yl chain or its salts.

Possible further anionic surfactants are in particular soaps. Saturated fatty acid soaps, such as the salts of lauric acid, myristic acid, palmitic acid, stearic acid, hydrogenated erucic acid and behenic acid and in particular soap mixtures derived from natural fatty acids, for example coconut, palm kernel or tallow fatty acids are suitable.

The anionic surfactants including the soaps can be present in the form of their sodium, potassium or ammonium salts and as soluble salts of organic bases, such as mono-, di- or triethanolamine. Preferably, the anionic surfactants are present in the form of their sodium or potassium salts, in particular in the form of the sodium salts.

The surfactants can be contained in the cleaners or detergents according to the invention as a whole in an amount of from preferably 5% by weight to 50% by weight, in particular of 8% by weight to 30% by weight, based on the finished composition.

Detergents or cleaners according to the invention can contain bleaches. Among the compounds serving as bleaches, which yield $H_2O_2$ in water, sodium percarbonate, sodium perborate tetrahydrate and sodium perborate monohydrate have particular importance. Further utilizable bleaches are, for example, peroxopyrophosphates, citrate perhydrates and peracid salts or peracids yielding $H_2O_2$, such as persulfates and persulfuric acid. Also utilizable is the urea peroxohydrate percarbamide, which can be described by the formula $H_2N—CO—NH_2.H_2O_2$. In particular when using the compositions for cleaning hard surfaces, for example in mechanical dishwashing, they can, if desired, also contain bleaches from the group consisting of the organic bleaches, although their use in principle is also possible in compositions for textile washing. Typical organic bleaches are the diacyl peroxides, such as, for example, dibenzoyl peroxide. Further typical organic bleaches are the peroxy acids, where as examples particularly the alkylperoxy acids and the arylperoxy acids are mentioned. Preferred representatives are peroxybenzoic acid and its ring-substituted derivatives, such as alkylperoxybenzoic acids, but also peroxy-.alpha.-naphthoic acid and magnesium monoperphthalate, the aliphatic or substituted aliphatic peroxy acids, such as peroxylauric acid, peroxystearic acid, .epsilon.-phthalimidoperoxycaproic acid (phthalimidoperoxyhexanoic acid, PAP), o-carboxybenzamidoperoxycaproic acid, N-nonenylamidoperadipic acid and N-nonenylamidopersuccinates, and aliphatic and araliphatic peroxy-dicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyldi(6-aminopercaproic acid) can be employed.

The content of bleach in the detergents or cleaners can be 1 to 40% by weight and in particular 10 to 20% by weight, where advantageously perborate monohydrate or percarbonate is employed.

When washing at temperatures of 60° C. and below, and in particular during the wash pretreatment, in order to achieve an improved bleaching action the compositions can also contain bleach activators. Bleach activators employed can be compounds which under perhydrolysis conditions afford aliphatic peroxocarboxylic acids preferably having 1 to 10 C atoms, in particular 2 to 4 C atoms, and/or optionally substituted perbenzoic acid. Suitable substances are those which carry O- and/or N-acyl groups of said C atom number and/or optionally substituted benzoyl groups. Polyacylated alkylenediamines are preferred, in particular tetraacetylethylenediamine (TAED), acylated triazine derivatives, in particular 1,5-diacetyl-2,4-dioxohexahydro-1,3,5-triazine (DADHT), acylated glycolurils, in particular 1,3,4,6-tetraacetylglycoluril (TAGU), N-acylimides, in particular N-nonanoyl-succinimide (NOSI), acylated phenolsulfonates, in particular n-nonanoyl- or isononanoyloxybenzenesulfonate (n- or iso-NOBS), acylated hydroxycarboxylic acids, such as triethyl O-acetylcitrate (TEOC), carboxylic acid anhydrides, in particular phthalic anhydride, isatoic anhydride and/or succinic anhydride, carboxylic acid amides, such as N-methyldiacetamide, glycolide, acylated polyhydric alcohols, in particular triacetin, ethylene glycol diacetate, isopropenyl acetate, 2,5-diacetoxy-2,5-dihydrofuran and the enol esters known from German patent applications DE 196 16693 and DE 196 16 767 and acetylated sorbitol and mannitol or their mixtures described in European patent application EP 0 525 239 (SORMAN), acylated sugar derivatives, in particular pentaacetylglucose (PAG), penta-acetylfructose, tetraacetylxylose and octaacetyllactose and also acetylated, optionally N-alkylated glucamine or gluconolactone, triazole or triazole derivatives and/or particulate caprolactams and/or caprolactam derivatives, preferably N-acylated lactams, for example N-benzoylcaprolactam and N-acetylcaprolactam, which are known from the international patent applications WO 94/27970, WO 94/28102, WO 94/28103, WO 95/00626, WO 95/14759 and WO 95/17498. The hydrophilically substituted acylacetals known from German patent application DE 196 16 769 and the acyllactams described in German patent application DE 196 16 770 and international patent application WO 95/14075 are likewise preferably employed. The combinations of conventional bleach activators known from German patent application DE 44 43 177 can also be employed. Likewise, nitrile derivatives such as cyanopyridines, nitrilequats, for example N-alkylammonium acetonitriles, and/or cyanamide derivatives can be employed. Preferred bleach activators are sodium 4-(octanoyloxy)benzenesulfonate, n-nonanoyl- or isononanoyl oxybenzenesulfonate (n- or iso-NOBS), undecenoyl oxybenzenesulfonate (UDOBS), sodium dodecanoyloxy-benzenesulfonate (DOBS), decanoyl-oxybenzoic acid (DOBA, OBC 10) and/or dodecanoyl oxybenzenesulfonate (OBS 12), and N-methylmorpholinum acetonitrile (MMA). Bleach activators of this type can be contained in the customary range of amounts of 0.01 to 20% by weight, preferably in amounts of 0.1 to 15% by weight, in particular 1% by weight to 10% by weight, based on the total composition.

In addition to the conventional bleach activators or in their place, "bleach catalysts" can also be contained. These substances are bleach-strengthening transition metal salts or transition metal complexes such as, for example, Mn-, Fe-, Co-, Ru- or Mo-salene complexes or -carbonyl complexes. Mn, Fe, Co, Ru, Mo, Ti, V and Cu complexes with N-containing tripod ligands and Co-, Fe-, Cu- and Ru-ammine complexes are also suitable as bleach catalysts, where those compounds are preferably to be employed which are described in DE 19709284 A1.

Detergents or cleaners according to the invention as a rule contain one or more builders, in particular zeolites, silicates, carbonates, organic cobuilders and—where no ecological reasons speak against their use—also the phosphates. The latter are in particular builders preferably to be employed in cleaners for mechanical dishwashing.

Crystalline, laminar sodium silicates of the general formula $NaMSi_xO_{2x+1}\cdot yH_2O$ may be mentioned here, where M is sodium or hydrogen, x is a number from 1.6 to 4, preferably 1.9 to 4.0 and y is a number from 0 to 20 and preferred values for x are 2, 3 or 4. Crystalline layer silicates of this type are described, for example in European patent application EP 164514. Preferred crystalline layer silicates of the formula indicated are those in which M is sodium and x assumes the values 2 or 3. In particular, both β- and δ-sodium disilicates $Na_2Si_2O_5\cdot yH_2O$ are preferred. Commercially, compounds of this type are found, for example, under the name SKS® (Clariant). Thus, SKS-6® is mainly a δ-sodium disilicate having the formula $Na_2Si_2O_5\cdot yH_2O$, in the case of SKS-7® mainly the β-sodium disilicate. By reaction with acids (for example citric acid or carbonic acid), kanemite $Na_2Si_2O_5\cdot yH_2O$ is formed from the δ-sodium disilicate, commercially under the names SKS-9® and SKS-10® (Clariant). It can also be advantageous to employ chemical modifications of these layer silicates. For example, the alkalinity of the layer silicates can be suitably influenced. In comparison to δ-sodium disilicate, layer silicates doped with phosphate or with carbonate have modified crystal morphologies, dissolve more rapidly and in comparison to δ-sodium disilicate show an increased calcium-binding power. Thus layer silicates of the general empirical formula $xNa_2O\cdot ySiO_2\cdot zP_2O_5$, in which the ratio x to y corresponds to a number 0.35 to 0.6, the ratio x to z corresponds to a number from 1.75 to 1200 and the ratio y to z corresponds to a number from 4 to 2800, are described in the patent application DE 196 01 063. The solubility of the layer silicates can also be increased by employing particularly finely divided layer silicates. Compounds of the crystalline layer silicates with other ingredients can also be employed. Here, in particular compounds with cellulose derivatives, which have advantages in the disintegrating action and are in particular employed in detergent tablets, and compounds with polycarboxylates, for example citric acid, or polymeric polycarboxylates, for example copolymers of acrylic acid, may be mentioned.

Also employable are amorphous sodium silicates having a modulus $Na_2O:SiO_2$ of 1:2 to 1:3.3, preferably of 1:2 to 1:2.8 and in particular of 1:2 to 1:2.6, which are solution-retarded and have secondary wash properties. The solution retardation compared to conventional amorphous sodium silicates can have been produced here in various ways, for example by surface treatment, compounding, compaction/compression or by overdrying. In the context of this invention, the term "amorphous" is also understood as meaning "X-ray-amorphous". This means that in X-ray diffraction experiments the silicates do not produce any sharp X-ray reflections, as are typical for crystalline substances, but at most one or more maxima of the scattered X-ray radiation, which have a breadth of a number of degree units of the diffraction angle. However, it can very probably even lead to particularly good builder properties if the silicate particles in electron diffraction experiments produce indistinct or even sharp diffraction maxima. This is to be interpreted in such a way that the products have microcrystalline regions of the size 10 to a few hundred nm, where values to at most 50 nm and in particular to at most 20 nm are preferred. In particular, compressed/compacted amorphous silicates, compounded amorphous silicates and overdried X-ray amorphous silicates are preferred.

An optionally employable, fine-crystalline, synthetic and bound water-containing zeolite is preferably zeolite A and/or P. As zeolite P, zeolite MAP® (commercial product of Crosfield) is particularly preferred. However, zeolite X and mixtures of A, X and/or P are also suitable. Also commercially obtainable and in the context of the present invention preferably employable is, for example, a cocrystallizate of zeolite X and zeolite A (about 80% by weight zeolite X), which is marketed by CONDEA Augusta S.p.A. under the trade name VEGOBOND AX® and can be described by the formula

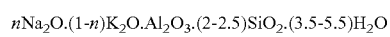
$nNa_2O\cdot(1-n)K_2O\cdot Al_2O_3\cdot(2-2.5)SiO_2\cdot(3.5-5.5)H_2O$ Suitable zeolites have a mean particle size of less than 10 μm (volume distribution; measuring method: Coulter counter) and preferably contain 18 to 22% by weight, in particular 20 to 22% by weight, of bound water.

Of course, use of the generally known phosphates as builder substances is also possible, provided a use of this type should not be avoided for ecological reasons. Among the large number of commercially obtainable phosphates, the alkali metal phosphates, with particular preference of pentasodium or pentapotassium triphosphate (sodium or potassium-tripolyphosphate), have the greatest importance in the detergent and cleaner industry.

Alkali metal phosphates is here the summary designation for the alkali metal (in particular sodium and potassium) salts of the various phosphoric acids, in which a distinction can be made between metaphosphoric acids $(HPO_3)_n$ and orthophosphoric acid $H_3PO_4$ in addition to higher molecular weight representatives. The phosphates here combine a number of advantages in themselves—they act as alkali carriers, prevent lime deposits on machine parts or lime incrustations in fabrics and moreover contribute to the cleaning performance.

Sodium dihydrogenphosphate, $NaH_2PO_4$, exists as a dihydrate (density 1.91 $gcm^{-3}$, melting point 60° C.) and as a monohydrate (density 2.04 $gcm^{-3}$). Both salts are white, very readily water-soluble powders, which on heating lose the water of crystallization and at 200° C. turn into the weakly acidic diphosphate (disodium hydrogendiphosphate, $Na_2H_2P_2O_7$), at higher temperature into sodium trimetaphosphate $(Na_3P_3O_9)$ and Maddrell's salt (see below). $NaH_2PO_4$ has an acidic reaction; it is formed when phosphoric acid is adjusted with sodium hydroxide solution to a pH of 4.5 and the mash is sprayed. Potassium dihydrogenphosphate (primary or monobasic potassium phosphate, potassium biphosphate, KDP), $KH_2PO_4$, is a white salt of density 2.33 $gcm^{-3}$, has a melting point of 253° C. [decomposition with formation of potassium polyphosphate $(KPO_3)_x$] and is readily soluble in water.

Disodium hydrogenphosphate (secondary sodium phosphate), $Na_2HPO_4$, is a colorless, very readily water-soluble crystalline salt. It exists in anhydrous form and with 2 mol (density 2.066 $gcm^{-3}$, loss of water at 95° C.), 7 mol (density 1.68 $gcm^{-3}$, melting point 48° C. with loss of $5H_2O$) and 12 mol of water (density 1.52 $gcm^{-3}$, melting point 35° C. with loss of $5H_2O$), becomes anhydrous at 100° C. and on relatively strong heating turns into the diphosphate $Na_4P_2O_7$. Disodium hydrogenphosphate is prepared by neutralization of phosphoric acid with sodium carbonate solution using phenolphthalein as an indicator. Dipotassium hydrogenphosphate (secondary or dibasic potassium phosphate), $K_2HPO_4$, is an amorphous, white salt which is readily soluble in water.

Trisodium phosphate, tertiary sodium phosphate, Na$_3$PO$_4$, are colorless crystals, which as the dodecahydrate have a density of 1.62 gcm$^{-3}$ and a melting point of 73-76° C. (decomposition), as the decahydrate (corresponding to 19-20% P$_2$O$_5$) a melting point of 100° C. and in anhydrous form (corresponding to 39-40% P$_2$O$_5$) a density of 2.536 gcm$^{-3}$. Trisodium phosphate is readily soluble in water with an alkaline reaction and is prepared by evaporating a solution of exactly 1 mol of disodium phosphate and 1 mol of NaOH. Tripotassium phosphate (tertiary or tribasic potassium phosphate), K$_3$PO$_4$, is a white, deliquescent, granular powder of density 2.56 gcm$^{-3}$, has a melting point of 1340° C. and is readily soluble in water with an alkaline reaction. It is formed, for example, on heating Thomas's slag with coal and potassium sulfate. In spite of the relatively high price, in the cleaner industry the more readily soluble, therefore highly active, potassium phosphates are widely preferred compared to corresponding sodium compounds.

Tetrasodium diphosphate (sodium pyrophosphate), Na$_4$P$_2$O$_7$, exists in anhydrous form (density 2.534 gcm$^{-3}$, melting point 988° C., also stated 880° C.) and as a decahydrate (density 1.815-1.836 gcm$^{-3}$, melting point 94° C. with loss of water). Both substances are colorless crystals soluble in water with an alkaline reaction. Na$_4$P$_2$O$_7$ is formed on heating disodium phosphate to >200° C. or by reacting phosphoric acid with sodium carbonate in the stoichiometric ratio and dehydrating the solution by spraying. The decahydrate complexes heavy metal salts and hardness formers and therefore decreases the hardness of the water. Potassium diphosphate (potassium pyrophosphate), K$_4$P$_2$O$_7$, exists in the form of the trihydrate and is a colorless, hygroscopic powder having the density 2.33 gcm$^{-3}$, which is soluble in water, the pH of the 1% strength solution being 10.4 at 25° C.

By condensation of NaH$_2$PO$_4$ or of KH$_2$PO$_4$, relatively high molecular weight sodium and potassium phosphates are formed, in which cyclic representatives, the sodium or potassium metaphosphates and chain-like types, the sodium or potassium polyphosphates, can be differentiated. In particular for the latter, a large number of designations are in use: fusible or calcined phosphates, Graham's salt, Kurrol's and Maddrell's salt. All higher sodium and potassium phosphates are together designated as condensed phosphates.

The industrially important pentasodium triphosphate (Na$_5$P$_3$O$_{10}$; sodium tripoly-phosphate) is a nonhygroscopic, white, water-soluble salt which is anhydrous or crystallizes with 6H$_2$O, of the general formula NaO—[P(O)(ONa)—O]$_n$—Na where n=3. In 100 g of water, approximately 17 g of the salt free of water of crystallization dissolve at room temperature, about 20 g at 60° C., around 32 g at 100° C.; after heating of the solution at 100° C. for two hours approximately 8% of orthophosphate and 15% of diphosphate are formed by hydrolysis. In the preparation of pentasodium triphosphate, phosphoric acid is reacted with sodium carbonate solution or sodium hydroxide solution in a stoichiometric ratio and the solution is dehydrated by spraying. Similarly to Graham's salt and sodium diphosphate, pentasodium triphosphate dissolves many insoluble metal compounds (lime, soaps, etc.). Pentapotassium triphosphate, K$_5$P$_3$O$_{10}$ (potassium tripolyphosphate), comes onto the market, for example, in the form of a 50% strength by weight solution (>23% P$_2$O$_5$, 25% K$_2$O). The potassium polyphosphates are widely used in the detergent and cleaner industry. Furthermore, sodium potassium tripolyphosphates also exist, which are likewise employable in the context of the present invention. These are formed, for example, when sodium trimetaphosphate is hydrolyzed using KOH:

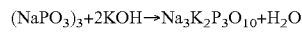

$(NaPO_3)_3 + 2KOH \rightarrow Na_3K_2P_3O_{10} + H_2O$

These are employable according to the invention precisely as sodium tripolyphosphate, potassium tripolyphosphate or mixtures of these two; mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate are also employable according to the invention.

Organic cobuilders which can be employed in the detergents and cleaners according to the invention are, in particular, polycarboxylates or polycarboxylic acids, polymeric polycarboxylates, polyaspartic acid, polyacetals, optionally oxidized dextrins, further organic cobuilders (see below) and phosphonates. These classes of substance are described below.

Usable organic builder substances are, for example, the polycarboxylic acids employable in the form of their sodium salts, polycarboxylic acids being understood as meaning those carboxylic acids which carry more than one acid function. For example, these are citric acid, adipic acid, succinic acid, glutaric acid, malic acid, tartaric acid, maleic acid, fumaric acid, sugar acids, aminocarboxylic acids, nitrilotriacetic acid (NTA), provided a use of this type is not to be avoided for ecological reasons, and mixtures of these. Preferred salts are the salts of the polycarboxylic acids such as citric acid, adipic acid, succinic acid, glutaric acid, tartaric acid, sugar acids and mixtures of these.

The acids per se can also be employed. In addition to their builder action, they typically also have the property of an acidification component and thus also serve for the setting of a relatively low and relatively mild pH of detergents or cleaners, provided the pH resulting due to the mixing of the other components is not desired. In particular, here system- and environmentally tolerable acids such as citric acid, acetic acid, tartaric acid, malic acid, lactic acid, glycolic acid, succinic acid, glutaric acid, adipic acid, gluconic acid and any desired mixtures of these may be mentioned. However, mineral acids, in particular sulfuric acid or bases, in particular ammonium or alkali metal hydroxides can also serve as pH regulators. Regulators of this type are contained in the compositions according to the invention in amounts of preferably not over 20% by weight, in particular of 1.2% by weight to 17% by weight.

As builders, further polymeric polycarboxylates are suitable, these are, for example, the alkali metal salts of polyacrylic acid or of polymethacrylic acid, for example those having a relative molecular mass of 500 to 70,000 g/mol.

Within the meaning of this specification, the molar masses indicated for polymeric polycarboxylates are weight-average molar masses Mw of the respective acid form, which were basically determined by means of gel permeation chromatography (GPC), a UV detector being employed. Measurement was carried out here against an external polyacrylic acid standard, which on account of its structural relationship with the polymers investigated yields realistic molecular weight values. These data differ distinctly from the molecular weight data in which polystyrenesulfonic acids are employed as a standard. The molar masses measured against polystyrenesulfonic acids are as a rule distinctly higher than the molar masses indicated in this specification.

Suitable polymers are in particular polyacrylates which preferably have a molecular mass of 2000 to 20,000 g/mol. On account of their superior solubility, from this group, in turn, the short-chain polyacrylates, which have molar masses of 2000 to 10,000 g/mol, and particularly preferably of 3000 to 5000 g/mol, can be preferred.

Furthermore suitable are copolymeric polycarboxylates, in particular those of acrylic acid with methacrylic acid and acrylic acid or methacrylic acid with maleic acid. Copolymers of acrylic acid with maleic acid have proven particularly suitable, which contain 50 to 90% by weight of acrylic acid and 50 to 10% by weight of maleic acid. Their relative molecular mass, based on free acids, is in general 2000 to 70,000 g/mol, preferably 20,000 to 50,000 g/mol and in particular 30,000 to 40,000 g/mol. The (co)polymeric polycarboxylates can be employed either as a powder or as an aqueous solution. The content of (co)polymeric polycarboxylates in the compositions can be from 0.5 to 20% by weight, in particular 1 to 10% by weight.

For an improvement of the water solubility, the polymers can also contain allylsulfonic acids, such as, for example, allyloxybenzenesulfonic acid and methallylsulfonic acid, as monomers.

In particular, biodegradable polymers of more than two different monomer units are also preferred, for example those which as monomers contain salts of acrylic acid and of maleic acid and vinyl alcohol or vinyl alcohol derivatives or which as monomers contain salts of acrylic acid and 2-alkylallylsulfonic acid and sugar derivatives.

Further preferred copolymers are those which as monomers preferably contain acrolein and acrylic acid/acrylic acid salts or acrolein and vinyl acetate.

Likewise, further preferred builder substances which may be mentioned are polymeric aminodicarboxylic acids, their salts or their precursor substances. Polyaspartic acids and their salts and derivatives are particularly preferred.

Further suitable builder substances are polyacetals which can be obtained by reaction of dialdehydes with polyolcarboxylic acids which have 5 to 7 C atoms and at least 3 hydroxyl groups. Preferred polyacetals are obtained from dialdehydes such as glyoxal, glutaraldehyde, terephthalaldehyde and their mixtures and from polyolcarboxylic acids such as gluconic acid and/or glucoheptonoic acid.

Further suitable organic builder substances are dextrins, for example oligomers and polymers of carbohydrates, which can be obtained by partial hydrolysis of starches. The hydrolysis can be carried out according to customary methods, for example acid- or enzyme-catalyzed methods. Preferably, they are hydrolysis products having average molar masses in the range from 400 to 500,000 g/mol. Here, a polysaccharide having a dextrose equivalent (DE) in the range from 0.5 to 40, in particular from 2 to 30, is preferred, where DE is a customary measure of the reducing action of a polysaccharide in comparison to dextrose, which has a DE of 100. Both maltodextrins having a DE between 3 and 20 and dry glucose syrups having a DE between 20 and 37 and also "yellow dextrins" and "white dextrins" having relatively high molar masses in the range from 2000 to 30,000 g/mol are usable.

The oxidized derivatives of dextrins of this type are their reaction products with oxidants which are able to oxidize at least one alcohol function of the saccharide ring to the carboxylic acid function. Particularly preferred organic builders for compositions according to the invention are oxidized starches, or their derivatives from the applications EP 472042, WO 97/25399, and EP 755944.

Oxydisuccinates and other derivatives of disuccinates, preferably ethylenediamine disuccinate, are also further suitable cobuilders. Here, ethylenediamine-N,N'-disuccinate (EDDS) is preferably used in the form of its sodium or magnesium salts. Furthermore, in this connection glycerol disuccinates and glycerol trisuccinates are also preferred. Suitable use amounts in zeolite-, carbonate- and/or silicate-containing formulations lie between 3 and 15% by weight.

Further usable organic cobuilders are, for example, acetylated hydroxycarboxylic acids and their salts, which can optionally also be present in lactone form and which contain at least 4 carbon atoms and at least one hydroxyl group and also at most two acid groups.

A further substance class with cobuilder properties are the phosphonates. These are in particular hydroxyalkane or aminoalkane phosphonates. Among the hydroxyalkane phosphonates, 1-hydroxyethane 1,1-diphosphonate (HEDP) is of particular importance as a cobuilder. It is preferably employed as the sodium salt, the disodium salt having a neutral reaction and the tetrasodium salt an alkaline reaction (pH 9). Suitable aminoalkane phosphonates are preferably ethylenediamine tetramethylenephosphonate (EDTMP), diethylenetriamine pentamethylenephosphonate (DTPMP) and their higher homologs. They are preferably employed in the form of the neutral-reacting sodium salts, e.g. as the hexasodium salt of EDTMP or as the hepta- and octasodium salt of DTPMP. As a builder, from the class of the phosphonates preferably HEDP is used here. The aminoalkane phosphonates moreover have marked heavy-metal binding power. Accordingly, in particular if the compositions also contain bleach, it can be preferred to use aminoalkane phosphonates, in particular DTPMP, or mixtures of said phosphonates.

Moreover, all compounds which are able to form complexes with alkaline earth metal ions can be employed as cobuilders.

Builder substances can optionally be present in the detergents or cleaners according to the invention in amounts up to 90% by weight. They are preferably present in amounts up to 75% by weight. Detergents according to the invention have builder contents of, in particular, 5% by weight to 50% by weight. In compositions according to the invention for cleaning hard surfaces, in particular for the mechanical cleaning of dishes, the content of builder substances is in particular 5% by weight to 88% by weight, preferably no water-insoluble builder materials being employed in compositions of this type. In a preferred embodiment of compositions according to the invention for, in particular, mechanical cleaning of dishes, 20% by weight to 40% by weight of water-soluble organic builders, in particular alkali metal citrate, 5% by weight to 15% by weight of alkali metal carbonate and 20% by weight to 40% by weight of alkali metal disilicate are present.

Solvents which can be employed in the liquid to gelatinous compositions of detergents and cleaners originate, for example, from the group consisting of mono- or polyhydric alcohols, alkanolamines or glycol ethers, provided they are miscible with water in the concentration range indicated. Preferably, the solvents are selected from ethanol, n- or i-propanol, butanols, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl, or ethyl ether, diisopropylene glycol monomethyl, or ethyl ether, methoxy-, ethoxy- or butoxytriglycol, 1-butoxyethoxy-2-propanol, 3-methyl-3-methoxybutanol, propylene glycol t-butyl ether and mixtures of these solvents.

Solvents can be employed in the liquid to gelatinous detergents and cleaners according to the invention in amounts between 0.1 and 20% by weight, but preferably below 15% by weight and in particular under 10% by weight.

For adjustment of the viscosity, one or more thickeners, or thickening systems, can be added to the composition according to the invention. These high molecular weight substances, which are also called swelling agents, usually absorb the liquids and swell here, in order finally to turn to viscous true or colloidal solutions.

Suitable thickeners are inorganic or polymeric organic compounds. The inorganic thickeners include, for example, polysilicic acids, clay minerals such as montmorillonites, zeolites, silicas and bentonites. The organic thickeners originate from the groups consisting of the natural polymers, of the modified natural polymers and of the fully synthetic polymers. Such polymers originating from nature are, for example, agar-agar, carrageenan, tragacanth, gum arabic, alginates, pectins, polyoses, guar flour, carob bean flour, starch, dextrins, gelatin and casein. Modified natural substances which are used as thickeners originate especially from the group consisting of the modified starches and celluloses. By way of example, carboxymethylcellulose and other cellulose ethers, hydroxyethyl- and -propylcellulose and pome flour ethers may be mentioned here. Fully synthetic thickeners are polymers such as polyacrylic and polymethacrylic compounds, vinyl polymers, polycarboxylic acids, polyethers, polyimines, polyamides and polyurethanes.

The thickeners can be present in an amount up to 5% by weight, preferably from 0.05 to 2% by weight, and particularly preferably from 0.1 to 1.5% by weight, based on the finished composition.

The detergent and cleaner according to the invention can optionally contain as further customary ingredients sequestering agents, electrolytes and further auxiliaries, such as optical brighteners, graying inhibitors, silver corrosion inhibitors, color transfer inhibitors, foam inhibitors, abrasives, colorants and/or scents, and microbial active compounds, UV absorbents and/or enzyme stabilizers.

Textile detergents according to the invention can contain as optical brighteners derivatives of diaminostilbenedisulfonic acid or its alkali metal salts. For example, salts of 4,4'-bis(2-anilino-4-morpholino-1,3,5-triazinyl-6-amino)stilbene-2,2'-dis-ulfonic acid or similarly synthesized compounds are suitable which, instead of the morpholino group carry a diethanolamino group, a methylamino group, an anilino group or a 2-methoxyethylamino group. Furthermore, brighteners of the type consisting of the substituted diphenylstyryls can be present, for example the alkali metal salts of 4,4'-bis (2-sulfostyryl)diphenyl, 4,4'-bis(4-chloro-3-sulfostyryl) diphenyl, or 4-(4-chlorostyryl)-4'-(2-sulfostyryl)diphenyl. Mixtures of the abovementioned optical brighteners can also be used.

Graying inhibitors have the object of keeping the dirt detached from the textile fibers suspended in the liquor. For this, water-soluble colloids, usually of organic nature, are suitable, for example starch, size, gelatin, salts of ether carboxylic acids or ether sulfonic acids of starch or of cellulose or salts of acidic sulfuric acid esters of cellulose or of starch. Water-soluble polyamides containing acidic groups are also suitable for this purpose. Furthermore, other derivatives than the abovementioned starch derivatives can be used, for example aldehyde starches. Preferably, cellulose ethers such as carboxymethylcellulose (Na salt), methylcellulose, hydroxyalkylcellulose and mixed ethers, such as methylhydroxyethylcellulose, methylhydroxypropylcellulose, methylcarboxy-methylcellulose and their mixtures, for example in amounts from 0.1 to 5% by weight, based on the compositions are employed.

In order to effect silver corrosion protection, silver corrosion inhibitors can be employed in cleaners according to the invention for dishes. Such inhibitors are known from the prior art, for example benzotriazoles, iron (III) chloride or $CoSO_4$. As is known, for example, from European patent specification EP 0 736 084 B1, particularly suitable silver corrosion inhibitors for joint use with enzymes are manganese, titanium, zirconium, hafnium, vanadium, cobalt or cerium salts and/or complexes, in which said metals are present in one of the oxidation states II, III, IV, V or VI. Examples of compounds of this type are $MnSO_4$, $V_2O_5$, $V_2O_4$, $VO_2$, $TiOSO_4$, $K_2TiF_6$, $K_2ZrF_6$, $Co(NO_3)_2$, $Co(NO_3)_3$, and their mixtures.

"Soil release" active compounds or "soil repellents" are usually polymers which on use in a detergent impart dirt-repellent properties to the wash fibers and/or assist the dirt-removing power of the other detergent constituents. A comparable effect can also be observed in their use in cleaners for hard surfaces.

Soil-release active compounds which are particularly effective and have been known for a long time are copolyesters with dicarboxylic acid, alkylene glycol and polyalkylene glycol units. Examples of these are copolymers or mixed polymers of polyethylene terephthalate and polyoxyethylene glycol (DT 16 17 141, and DT 22 00 911 respectively). In German laid-open specification DT 22 53 063, acidic compositions are mentioned, which inter alia contain a copolymer of a dibasic carboxylic acid and an alkylene or cycloalkylene polyglycol. Polymers of ethylene terephthalate and polyethylene oxide terephthalate and their use in detergents are described in German specifications DE 28 57 292 and DE 33 24 258 and European patent specification EP 0 253 567. European patent EP 066 944 relates to compositions which contain a copolyester of ethylene glycol, polyethylene glycol, aromatic dicarboxylic acid and sulfonated aromatic dicarboxylic acid in specific molar ratios. From European patent EP 0 185 427, methyl or ethyl group end-closed polyesters with ethylene and/or propylene terephthalate and polyethylene oxide terephthalate units and detergents which contain soil-release polymers of this type are known. European patent EP 0 241 984 relates to a polyester which, in addition to oxyethylene groups and terephthalic acid units also contains substituted ethylene units and glycerol units. From European patent EP 0 241 985, polyesters are known which in addition to oxyethylene groups and terephthalic acid units contain 1,2-propylene, 1,2-butylene and/or 3-methoxy-1,2-propylene groups and glycerol units and are end group-closed with $C_1$- to $C_4$-alkyl groups. From European patent application EP 0 272 033, polyesters at least partly end group-closed by $C_{1-4}$ alkyl or acyl radicals with polypropylene terephthalate and polyoxyethylene terephthalate units are known. European patent EP 0 274 907 describes sulfoethyl end group-closed terephthalate-containing soil-release polyesters. According to European patent application EP 0 357 280, by sulfonation of unsaturated end groups, soil-release polyesters having terephthalate, alkylene glycol and poly-$C_{2-4}$-glycol units are prepared. International patent application WO 95/32232 relates to acidic, aromatic dirt removal-empowering polyesters. From international patent application WO 97/31085, nonpolymeric soil-repellent active compounds for materials made of cotton having a number of functional units are known: A first unit which, for example, can be cationic, is capable of adsorption on the cotton surface by electrostatic interaction, and a second unit, which is of hydrophobic design, is responsible for the active compound remaining on the water/cotton interface.

The color transfer inhibitors suitable for use in textile detergents according to the invention in particular include polyvinylpyrrolidones, polyvinylimidazoles, polymeric N-oxides such as poly(vinylpyridine N-oxide) and copolymers of vinylpyrrolidone with vinylimidazole.

When used in mechanical cleaning methods, it can be advantageous to add foam inhibitors to the compositions concerned. Suitable foam inhibitors are, for example, soaps of natural or synthetic origin, which have a high content of $C_{18}$-$C_{24}$ fatty acids. Suitable nonsurfactant-like foam inhibitors are, for example, organopolysiloxanes and their mixtures with microfine, optionally silanized silicic acid and paraffins, waxes, microcrystalline waxes and their mixtures with silanized silicic acid or bistearylethylenediamide. Mixtures of various foam inhibitors are also used to advantage, for example those consisting of silicones, paraffins or waxes. Preferably, the foam inhibitors, in particular silicone- and/or paraffin-containing foam inhibitors, are bound to a granular, water-soluble, or -dispersible, carrier substance. In particular, mixtures of paraffins and bistearylethylenediamides are preferred.

A cleaner according to the invention for hard surfaces can moreover contain constituents having abrasive action, in particular from the group comprising quartz powder, sawdust, plastic powder, chalks and microglass beads, and their mixtures. Abrasives are present in the cleaners according to the invention preferably not over 20% by weight, in particular from 5% by weight to 15% by weight.

Colorants and scents are added to detergents and cleaners in order to improve the esthetic impression of the products and to make available to the consumer, in addition to the washing and cleaning performance, a visually and sensorily "typical and unmistakable" product. Perfume oils and scents which can be used are individual odorants, for example the synthetic products of the type consisting of the esters, ethers, aldehydes, ketones, alcohols and hydrocarbons. Odorants of the type consisting of the esters are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether, the aldehydes, for example, the linear alkanals having 8-18 C atoms, citral, citronellal, citronellyloxyacetaldehyde, cyclamenaldehyde, hydroxycitronellal, lilial and bourgeonal, the ketones, for example, the ionones, .alpha.-isomethylionone and methyl cedryl ketone, the alcohols anethol, citronellol, eugenol, geraniol, linalool, phenylethyl alcohol and terpineol, the hydrocarbons mainly include the terpenes such as limonene and pinene. Preferably, however, mixtures of various odorants are used, which together produce a pleasant scent note. Such perfume oils can also contain natural odorants, such as are accessible from plant sources, for example pine, citrus, jasmine, patchouli, rose or ylang-ylang oil. Muscatel, sage oil, camomile oil, oil of cloves, melissa oil, mint oil, oil of cinnamon leaves, linden blossom oil, oil of juniper berries, vetiver oil, olibanum oil, galbanum oil and labdanum oil and also orange blossom oil, neroliol, orange peel oil and sandalwood oil. Customarily, the content of colorants in detergents and cleaners lies below 0.01% by weight, while scents can make up up to 2% by weight of the total formulation.

The scents can be incorporated directly into the detergents or cleaners, but it can also be advantageous to apply the scents to carriers which increase the adhesion of the perfume to the material to be cleaned and by means of a slower release of scent provide for a long-lasting scent, in particular from treated textiles. Such carrier materials which have proven to be suitable are, for example, cyclodextrins, where the cyclodextrin-perfume complexes can additionally also be coated with further auxiliaries. A further preferred carrier for scents is the described zeolite X, which can also absorb scents instead of or as a mixture with surfactants. Detergents and cleaners which contain the described zeolite X and scents which are preferably absorbed at least partly on the zeolite are therefore preferred.

Preferred colorants whose choice causes no difficulty at all to the person skilled in the art have a high storage stability and insensitivity to the other ingredients of the compositions and to light, and no marked substantivity to textile fibers, in order not to color these.

For the control of microorganisms, detergents or cleaners can contain antimicrobial active compounds. Here, a distinction is made, depending on the antimicrobial spectrum and mechanism of action, between bacteriostatics and bactericides, fungistatics and fungicides etc. Important substances from these groups are, for example, benzalkonium chlorides, alkylarylsulfonates, halophenols and phenol mercuriacetate. In the context of the teaching according to the invention, the terms antimicrobial action and antimicrobial active compound have the meaning standard in practice, which is given, for example, by K. H. Wallhäußer in *Praxis der Sterilisation, Desinfektion—Konservierung: Keimidentifizierung—Betriebshygiene*[Practice of Sterilization, Disinfection—Preservation: Microorganism Identification—Plant Hygiene] (5th ed., Stuttgart, New York: Thieme, 1995), where all substances described there having antimicrobial action can be employed. Suitable antimicrobial active compounds are preferably selected from the groups consisting of the alcohols, amities, aldehydes, antimicrobial acids or their salts, carboxylic acid esters, acid amides, phenols, phenol derivatives, diphenyls, diphenylalkanes, urea derivatives, oxygen and nitrogen acetals and formals, benzamidines, isothiazolines, phthalimide derivatives, pyridine derivatives, antimicrobial surface-active compounds, guanidines, antimicrobial amphoteric compounds, quinolines, 1,2-dibromo-2,4-dicyanobutane, iodo-2-propylbutyl carbamate, iodine, iodophors, peroxo compounds, halogen compounds and any desired mixtures of the above.

The antimicrobial active compound can be selected here from ethanol, n-propanol, propanol, 1,3-butanediol, phenoxyethanol, 1,2-propylene glycol, glycerol, undecylenic acid, benzoic acid, salicylic acid, dihydracetic acid, o-phenylphenol, N-methylmorpholineacetonitrile (MMA), 2-benzyl-4-chlorophenol, 2,2'-methylenebis(6-bromo-4-chlorophenol), 4,4'-dichloro-2'-hydroxydiphenyl ether (dichlosan), 2,4,4'-trichloro-2'-hydroxydiphenyl ether (trichlosan), chlorhexidine, N-(4-chlorophenyl)-N-(3,4-dichlorophenyl)urea, N,N'-(1,10-decanediyldi-1-pyridinyl-4-ylidene)bis(1-octanamine) dihydrochloride, N,N'-bis(4-chlorophenyl)-3,12-diimino-2,4,11,13-tetraazatetradecanediimid-amide, glucoprotamines, antimicrobial surface-active quaternary compounds, guanidines including the bi- and poly-guanidines, such as, for example, 1,6-bis(2-ethylhexy/biguanidohexane) dihydrochloride, 1,6-di(N1,N1'-phenyldiguanido-N5,N5')-hexane tetrahydrochloride, 1,6-di(N1,N1'-phenyl-N,N1-methyldiguanido-N5,N5')-hexane dihydrochloride, 1,6-di(N1,N1'-o-chlorophenyldiguanido-N5,N5')-hexane dihydrochloride, 1,6-di(N1,N1'-2,6-dichlorophenyldiguanido-N5,N5')-hexane dihydrochloride, 1,6-di(N1,N1'-beta-(p-methoxyphenyl)diguanido-N5,N5'-hexane dihydrochloride, 1,6-di(N1,N1'-alpha-methyl-beta-phenyldiguanido-N5,N5')-hexane dihydrochloride, 1,6-di(N1,N1'-p-nitrophenyldiguanido-N5,N5')-hexane dihydrochloride, omega:omega-di(N1,N1'-phenyldiguanido-N5,N5')-di-n-propyl ether dihydrochloride, omega:omega'-di(N1,N1'-p-chlorophenyldiguanido-N5, N5')-di-n-propyl ether tetrahydrochloride, 1,6-di(N1,N1'-2, 4-dichlorophenyldiguanido-N5,N5')-hexane tetrahydrochloride, 1,6-di(N1,N1'-p-methylphenyldiguanido-N5,N5')-hexane dihydrochloride, 1,6-di(N1,N1-2,4,5-trichlorophenyldiguanido-N5,N5')-hexane tetrahydrochloride, 1,6-di[N1,N1'-alpha-(p-chlorophenyl) ethyldiguanido-N5,N5']-hexane dihydrochloride, omega:omega-di(N1, N1'-p-chlorophenyldiguanido-N5,N5')-m-xylene dihydrochloride, 1,12-di(N1,N1'-p-chlorophenyldiguanido-N5,N5')-dodecane dihydrochloride, 1,10-di(N1,N1'-phenyldiguanido-N5,N5')-decane tetrahydrochloride, 1,12-di(N1,N1'-phenyldiguanido-N5,N5')-dodecane tetrahydrochloride, 1,6-di(N1,N1'-o-chlorophenyldiguanido-N5,N5')-hexane dihydrochloride, 1,6-di(N1, N1'-o-chlorophenyldiguanido-N5,N5')-hexane tetrahydrochloride, ethylenebis(1-tolylbiguanide), ethylenebis(p-tolylbiguanides), ethylenebis(3,5-dimethylphenylbiguanide), ethylenebis(p-tert-amylphenylbiguanide), ethylenebis(nonylphenylbiguanide), ethylenebis (phenylbiguanide), ethylenebis(N-butylphenylbiguanide), ethylenebis(2,5-diethoxyphenylbiguanide), ethylenebis(2,4-dimethylphenylbiguanide), ethylenebis(o-diphenylbiguanide), ethylenebis(mixed amyl naphthylbiguanide), N-butylethylenebis(phenylbiguanide), trimethylene-bis(o-tolylbiguanide), N-butyltrimethylenebis(phenylbiguanides) and the corresponding salts such as acetates, gluconates, hydrochlorides, hydrobromides, citrates, bisulfites, fluorides, polymaleates, N-coconut alkylsarcosinates, phosphites, hypophosphites, perfluorooctanoates, silicates, sorbates, salicylates, maleates, tartrates, fumarates, ethylene-diaminetetraacetates, iminodiacetates, cinnamates, thiocyanates, arginates, pyromellitates, tetracarboxybutyrates, benzoates, glutarates, monofluorophosphates, perfluoropropionates and any desired mixtures thereof. Furthermore, halogenated xylene and cresol derivatives, such as p-chlorometacresol or p-chlorometaxylene, and natural antimicrobial active compounds of plant origin (for example from spices or herbs), of animal and of microbial origin are suitable. Preferably, surface-active quaternary compounds having antimicrobial activity, a natural antimicrobial active compound of plant origin and/or a natural antimicrobial active compound of animal origin, extremely preferably at least one natural antimicrobial active compound of plant origin from the group comprising caffeine, theobromine and theophylline, and essential oils such as eugenol, thymol and geraniol, and/or at least one natural antimicrobial active compound of animal origin from the group comprising enzymes such as albumin from milk, lysozyme and lactoperoxidase, and/or at least one surface-active quaternary compound having antimicrobial activity containing an ammonium, sulfonium, phosphonium, iodonium or arsonium group, peroxo compounds and chloro compounds can be employed. Substances of microbial origin, "bacteriocins", can also be employed.

The quaternary ammonium compounds (QAC) suitable as antimicrobial active compounds have the general formula $(R^1)(R^2)(R^3)(R^4)N+X—$, in which $R^1$ to $R^4$ are identical or different $C_1$-$C_{22}$-alkyl radicals, $C_7$-$C_{28}$-aralkyl radicals or heterocyclic radicals, where two or, in the case of an aromatic integration as in pyridine, even three radicals together with the nitrogen atom form the heterocycle, for example a pyridinium or imidazolinium compound, and X— are halide ions, sulfate ions, hydroxide ions or similar anions. For an optimum antimicrobial action, preferably at least one of the radicals has a chain length of 8 to 18, in particular, 12 to 16 C atoms.

QAC can be prepared by reaction of tertiary amines with alkylating agents, such as, for example, methyl chloride, benzyl chloride, dimethyl sulfate, dodecyl bromide, but also ethylene oxide. The alkylation of tertiary amines having a long alkyl radical and two methyl groups is particularly easily possible, and the quaternization of tertiary amines having two long radicals and a methyl group can be carried out under mild conditions with the aid of methyl chloride. Amines which have three long alkyl radicals or hydroxy-substituted alkyl radicals are less reactive and are preferably quaternized using dimethyl sulfate.

Suitable QAC are, for example, benzalkonium chloride (N-alkyl-N,N-dimethylbenzylammonium chloride, CAS No. 8001-54-5), Benzalkon B (m,p-dichlorobenzyldimethyl-$C_{1-2}$-alkylammonium chloride, CAS No. 58390-78-6), benzoxonium chloride (benzyldodecyl-bis(2-hydroxyethyl)ammonium chloride), cetrimonium bromide (N-hexadecyl-N,N-trimethylammonium bromide, CAS No. 57-09-0), benzetonium chloride (N,N-dimethyl-N-[2-[2-[p-(1,1,3,3-tetramethylbutyl)phenoxy]ethox-y]ethyl]-benzylammonium chloride, CAS No. 121-54-0), dialkyldimethylammonium chlorides such as di-n-decyldimethylammonium chloride (CAS No. 7173-51-5-5), didecyldimethylammonium bromide (CAS No. 2390-68-3), dioctyldimethylammonium-chloric, 1-cetylpyridinium chloride (CAS No. 123-03-5) and thiazoline iodide (CAS No. 15764-48-1) and their mixtures. Particularly preferred QAC are the benzalkonium chlorides having C8-C18-alkyl radicals, in particular C12-C14-alkyl-benzyldimethylammonium chloride.

Benzalkonium halides and/or substituted benzalkonium halides are, for example, commercially obtainable as Barquat® ex Lonza, Marquat® ex Mason, Variquat® ex Witco/Sherex and Hyamine® ex Lonza, and Bardac® ex Lonza. Further commercially obtainable antimicrobial active compounds are N-(3-chloroallyl)hexaminium chloride such as Dowicide® and Dowicil® ex Dow, benzethonium chloride such as Hyamine® 1622 ex Rohm & Haas, methylbenzethonium chloride such as Hyamine® 10× ex Rohm & Haas, cetylpyridinium chloride such as cepacol chloride ex Merrell Labs.

The antimicrobial active compounds are employed in amounts of 0.0001% by weight to 1% by weight, preferably of 0.001% by weight to 0.8% by weight, particularly preferably of 0.005% by weight to 0.3% by weight and in particular of 0.01 to 0.2% by weight.

The detergents or cleaners according to the invention can contain UV absorbents (UV absorbers), which become attached to the treated textiles and improve the light resistance of the fibers and/or the light resistance of other recipe constituents. UV absorbers are to be understood as meaning organic substances (lightscreen filters) which are able to absorb ultraviolet rays and emit the absorbed energy again in the form of longer-wave radiation, for example heat.

Compounds which have these desired properties are, for example, the compounds and derivatives of benzophenone having substituents in the 2- and/or 4-position which are active by radiationless deactivation. Furthermore, substituted benzotriazoles, acrylates phenyl-substituted in the 3-position (cinnamic acid derivatives, optionally having cyano groups in the 2-position), salicylates, organic Ni complexes and natural substances such as umbelliferone and the endogenous urocanic acid are also suitable. Biphenyl and especially stilbene derivatives such as are described, for example, in EP 0728749 A and are commercially obtainable as Tinosorb® FD or Tinosorb® FR ex Ciba have particular importance. The following may be mentioned as UV-B absorbers: 3-benzylidenecamphor or 3-benzylidenenorcamphor and its derivatives, for example 3-(4-methylbenzy-lidene)camphor, such as described in EP 0693471 B1; 4-aminobenzoic acid derivatives, preferably 2-ethylhexyl 4-(dimethylamino)benzoate, 2-octyl 4-(dimethylamino)benzoate and amyl 4-(dimethylamino)benzoate; esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene); esters of salicylic acid, preferably 2-ethylhexyl salicylate, 4-isopropylbenzyl salicylate, homomethyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di-2-ethylhexyl 4-methoxybenzmalonate; triazine derivatives, such as, for example, 2,4,6-trianilino-(p-carbo-2'-ethyl-1'-hexyloxy)-1,3,5-triazine and octyl triazone, such as described in EP 0818450 A1 or dioctyl butamido triazone (Uvasorb® HEB); propane-1,3-diones, such as, for example, 1-(4-tert-butylphenyl)-3-(4'-methoxyphenyl)propane-1,3-dione; ketotricyclo(5.2.1.0)decane derivatives, such as described in EP 0694521 B1. 2-phenylbenzimidazole-5-sulfonic acid and its alkali metal, alkaline earth metal, ammonium, alkylammonium, alkanolammonium and glucammonium salts are further suitable; sulfonic acid derivatives of benzophenones, preferably 2-hydroxy-4-methoxybenzophenone-5-sulfonic acid and its salts; sulfonic acid derivatives of 3-benzylidenecamphor, such as, for example, 4-(2-oxo-3-bornylidenemethyl)benzenesulfonic acid and 2-methyl-5-(2-oxo-3-bornylidene)sulfonic acid and their salts.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoyl-methane (Parsol 1789), 1-phenyl-3-(4'-isopropylphenyl)propane-1,3-dione and enamine compounds, such as described in DE 19712033 A1 (BASF). The UV-A and UV-B filters can of course also be employed as mixtures. In addition to the soluble substances mentioned, insoluble lightscreen pigments, namely finely disperse, preferably nanoized metal oxides or salts are also suitable for this purpose. Examples of suitable metal oxides are in particular zinc oxide and titanium dioxide and oxides of iron, zirconium, silicon, manganese, aluminum and cerium and their mixtures. As salts, silicates (talc), barium sulfate or zinc stearate can be employed. The oxides and salts are already used in the form of the pigments for skin-caring and skin-protecting emulsions and decorative cosmetics. The particles should in this case have a mean diameter of less than 100 nm, preferably between 5 and 50 nm and in particular between 15 and 30 nm. They can have a spherical shape, but also those particles can be used which have an ellipsoidal shape or a shape differing in other ways from the spherical shape. The pigments can also be present in surface-treated, that is hydrophilicized or hydrophobicized, form. Typical examples are coated titanium dioxides, such as, for example, titanium dioxide T 805 (Degussa) or Eusolex® T2000 (Merck; suitable hydrophobic coating agents for this are preferably silicones and particularly preferably trialkoxyoctylsilanes or simethicones. Preferably, micronized zinc oxide is used. Further suitable UV lightscreen filters can be taken from the survey of P. Finkel in the SÖFW-Journal 122 (1996), p. 543.

The UV absorbents are customarily employed in amounts from 0.01% by weight to 5% by weight, preferably from 0.03% by weight to 1% by weight.

For increasing the washing or cleaning performance, compositions according to the invention can contain further enzymes, where in principle all enzymes established for these purposes in the prior art can be employed. These include, in particular, further proteases, amylases, lipases, hemicellulases, cellulases or oxidoreductases, and preferably their mixtures. These enzymes are in principle of natural origin; starting from the natural molecules, for use in detergents and cleaners improved variants are available, which are correspondingly preferably employed. Compositions according to the invention contain enzymes preferably in total amounts of 1×10-8 to 5 percent by weight based on active protein.

Among the further proteases, those of the subtilisin type are preferred. Examples of these are the subtilisins BPN' and Carlsberg, the protease PB92, the subtilisins 147 and 309, the alkaline protease from *Bacillus lentus*, subtilisin DY and the enzymes to be assigned thermitase, proteinase K and the proteases TW3 and TW7 to the subtilases, but no longer to the subtilisins in the narrower sense. Subtilisin Carlsberg is available in further developed form under the trade name Alcalase® from Novozymes A/S, Bagsvaerd, Denmark. The subtilisins 147 and 309 are marketed under the trade names Esperase®, or Savinase® by Novozymes. From the protease from *Bacillus lentus* DSM 5483 (WO 91/02792 A1) are derived the variants routed under the designation BLAP®, which are described in particular in WO 92/21760 A1, WO 95/23221 A1, WO 021088340 A2 and WO 03/038082 A2. Further usable proteases from various *Bacillus* sp. and *B. gibsonii* follow from the patent applications WO 03/054185 A1, WO 03/056017 A2, WO 03/055974 A2 and WO 03/054184 A1, already mentioned introductorily.

Further usable proteases are, for example, the enzymes obtainable under the trade names Durazym®, Relase®, Everlase®, Nafizym, Natalase®, Kannase® and Ovozymes® from Novozymes, the enzymes obtainable under the trade names Purafect®, Purafect® OxP and Properase® from Genencor, the enzymes obtainable under the trade name Protosol® from Advanced Biochemicals Ltd., Thane, India, the enzymes obtainable under the trade name Wuxi® from Wuxi Snyder Bioproducts Ltd., China, the enzymes obtainable under the trade names Proleather® and Protease P® from Amano Pharmaceuticals Ltd., Nagoya, Japan, and the enzyme obtainable under the name Proteinase K-16 from Kao Corp., Tokyo, Japan.

Examples of amylases employable according to the invention are the .alpha.-amylases from *Bacillus licheniformis*, from *B. amyloliquefaciens* or from *B. stearothermophilus* and their improved further developments for use in detergents and cleaners. The enzyme from *B. licheniformis* is obtainable from Novozymes under the name Termamyl® and from Genencor under the name Purastar®ST.

Further development products of this α-amylase are obtainable from Novozymes under the trade names Duramyl® and Termamyl®ultra, from Genencor under the name Purastar®OxAm and from Daiwa Seiko Inc., Tokyo, Japan, as Keistase®. The α-amylase of *B. amyloliquefaciens* is marketed by Novozymes under the name BAN®, and derived variants of the .alpha.-amylase from *B. stearothermophilus* under the names BSG® and Novamyl®, likewise from Novozymes.

In addition, for this purpose the α-amylase from *Bacillus* sp. A 7-7 (DSM 12368) disclosed in the application WO 02/10356 A2 and the cyclodextrin glucanotransferase (CG-Tase) from *B. agaradherens* (DSM 9948) described in the application WO 02/44350 A2 are to be stressed. Furthermore, the amylolytic enzymes can be employed which are part of the sequence space of α-amylases, which is defined in the application WO 03/002711 A2, and those which are defined in the application WO 03/054177 A2. Likewise, fusion products of said molecules can be employed, for example, those from the application DE 10138753 A1.

Moreover, the further developments of the α-amylase from *Aspergillus niger* and *A. oryzae* obtainable under the trade name Fungamyl® from Novozymes are suitable. A further commercial product is, for example, Amylase-LT®.

Compositions according to the invention can contain lipases or cutinases, in particular because of their triglyceride-cleaving activities, but also in order to produce peracids in situ from suitable precursors. These include, for example, the lipases originally obtainable from *Humicola lanuginosa* (*Thermomyces lanuginosus*), or further developed, in particular those having the amino acid replacement D96L. They are marketed, for example, by Novozymes under the trade names Lipolase®, Lipolase®Ultra, LipoPrime®, Lipozyme® and Lipex®. In addition, for example, the cutinases can be employed which have originally been isolated from *Fusarium solani pisi* and *Humicola insolens*. Lipases likewise usable are obtainable from Amano under the names Lipase CE®, Lipase P®, Lipase B®, or Lipase CES®, Lipase AKG®, *Bacillis* sp. Lipase®, Lipase AP®, Lipase M-AP® and Lipase AML®. From Genencor, for example, the lipases, or cutinases can be employed whose starting enzymes have originally been isolated from *Pseudomonas mendocina* and *Fusarium solanii*. Further important commercial products which may be mentioned are the preparations M1 Lipase® and Lipomax® originally marketed by Gist-Brocades and the enzymes marketed by Meito Sangyo KK, Japan, under the names Lipase MY-30®, Lipase OF® and Lipase PL®, furthermore the product Lumafast® from Genencor.

Compositions according to the invention, in particular if they are intended for the treatment of textiles, can contain cellulases, depending on the purpose as pure enzymes, as enzyme preparations or in the form of mixtures, in which the individual components advantageously complement each other with respect to their various performance aspects. These performance aspects include, in particular, contributions to the primary washing performance, to the secondary washing performance of the composition (antiredeposition action or graying inhibition) and reviving (fabric action), to the exertion of a "stone washed" effect.

A usable fungal, endoglucanase (EG)-rich cellulase preparation, or its further developments are supplied by Novozymes under the trade name Celluzyme®. The products Endolase® and Carezyme® likewise obtainable from Novozymes are based on the 50 kD EG, or the 43 kD EG, from *H. insolens* DSM 1800. Further commercial products from this company which can be employed are Cellusoft® and Renozyme®. The latter is based on the application WO 96/29397 A1. Improved-performance cellulase variants follow, for example, from the application WO 98/12307 A1. Likewise, the cellulases disclosed in the application WO 97/14804 A1 can be employed; for example the 20 kD EG from Melanocarpus disclosed therein, which is obtainable from AB Enzymes, Finland, under the trade names Ecostone® and Biotouch®. Further commercial products from AB Enzymes are Econase® and Ecopulp®. Further suitable cellulases from *Bacillus* sp. CBS 670.93 and CBS 669.93 are disclosed in WO 96/34092 A2, where the CBS 670.93 from *Bacillus* sp. is obtainable from Genencor under the trade name Puradax®. Further commercial products from Genencor are "Genencor detergent cellulase L" and IndiAge®Neutra.

Compositions according to the invention can contain, in particular for the removal of certain problem soiling, further enzymes which are summarized under the term hemicellulases. These include, for example mannanases, xanthanlyases, pectinlyases (=pectinases), pectin esterases, pectate lyases, xyloglucanases (=xylanases), pullulanases and β-glucanases. Suitable mannanases are obtainable, for example, under the names Gamanase® and Pektinex AR® from Novozymes, under the name Rohapec® B1 L from AB Enzymes and under the name Pyrolase® from Diversa Corp., San Diego, Calif., USA. A suitable β-glucanase from a *B. alcalophilus* follows, for example, from the application WO 99/06573 A1. The β-glucanase prepared from *B. subtilis* is obtainable under the name Cereflo® from Novozymes.

For increasing the bleaching action, detergents and cleaners according to the invention can contain oxidoreductases, for example oxidases, oxygenases, catalases, peroxidases, such as halo-, chloro-, bromo-, lignin, glucose or manganese peroxidases, dioxygenases or laccases (phenol oxidases, polyphenol oxidases). Suitable commercial products which may be mentioned are Denilite® 1 and 2 from Novozymes. Advantageously, preferably organic, particularly preferably aromatic compounds interacting with the enzymes are additionally added in order to increase the activity of the oxidoreductases concerned (enhancers) or in order, in the case of greatly different redox potentials between the oxidizing enzymes and the soiling to guarantee the electron flux (mediators).

The enzymes employed in compositions according to the invention are either derived originally from microorganisms, for example of the genera *Bacillus, Streptomyces, Humicola*, or *Pseudomonas*, and/or produced by suitable microorganisms by bio-technological methods known per se, for example by transgenic expression hosts of the genera *Bacillus* or filamentous fungi.

The purification of the enzymes concerned is more favorably carried out by methods established per se, for example by means of precipitation, sedimentation, concentration, filtration of the liquid phases, microfiltration, ultrafiltration, action of chemicals, deodorization or suitable combinations of these steps.

The enzymes can be added to compositions according to the invention in any form established according to the prior art. These include, for example, the solid preparations obtained by granulation, extrusion or lyophilization or, in particular in the case of liquid or gelatinous compositions, solutions of the enzymes, advantageously as concentrated as possible, low in water and/or treated with stabilizers.

Alternatively, the enzymes can be encapsulated both for the solid and for the liquid administration form, for example by spray drying or extrusion of the enzyme solution together with a, preferably natural, polymer or in the form of capsules, for example those in which the enzymes are enclosed as in a solidified gel or in those of the core-shell type, in which an enzyme-containing core is covered with a water-, air- and/or chemical-impermeable protective layer. In superimposed layers, further active compounds, for example stabilizers, emulsifiers, pigments, bleaches or colorants, can be applied. Capsules of this type are applied by methods known per se, for example by shaker or roller granulation or in fluidized-bed processes. Advantageously, granules of this type are low in dust, for example as a result of applying polymeric film-forming agents, and storage-stable on account of the coating.

Furthermore, it is possible to package two or more enzymes together, such that individual granules have a number of enzyme activities.

A protein and/or enzyme contained in a composition according to the invention can be protected, particularly during storage, against damage such as, for example, inactivation, denaturation or disintegration, for example by means of physical influences, oxidation or proteolytic cleavage. In the case of microbial preparation of the proteins and/or enzymes, an inhibition of the proteolysis is particularly preferred, in particular if the compositions also contain proteases. Preferred compositions according to the invention for this purpose contain stabilizers.

One group of stabilizers are reversible protease inhibitors. Frequently, for this purpose, benzamidine hydrochloride, borax, boric acids, boronic acids or their salts or esters are employed, among them especially derivatives having aromatic groups, for example ortho-, meta- or para-substituted phenylboronic acids, in particular 4-formylphenylboronic acid, or the salts or esters of said compounds. Peptide aldehydes, that is, oligopeptides having a reduced C-terminus, in particular, those consisting of 2 to 50 monomers, are also employed for this purpose. The peptidic reversible protease inhibitors include, inter alia, ovomucoid and leupeptin. Specific, reversible peptide inhibitors for the protease subtilisin and fusion proteins of proteases and specific peptide inhibitors are also suitable for this.

Further enzyme stabilizers are amino alcohols such as mono-, di-, triethanol- and -propanolamine and their mixtures, aliphatic carboxylic acids up to C12, such as, for example, succinic acid, other dicarboxylic acids or salts of said acids. End group-closed fatty acid amide alkoxylates are also suitable for this purpose. Certain organic acids employed as builders are able, as disclosed in WO 97/18287, to additionally stabilize an enzyme present.

Lower aliphatic alcohols, but especially polyols, such as, for example, glycerol, ethylene glycol, propylene glycol or sorbitol are further frequently employed enzyme stabilizers. Diglycerol phosphate also protects against denaturation by physical influences. Likewise, calcium and/or magnesium salts are employed, such as for example calcium acetate or calcium formate.

Polyamide oligomers or polymeric compounds such as lignin, water-soluble vinyl copolymers or cellulose ethers, acrylic polymers and/or polyamides stabilize the enzyme preparation, inter alia, to physical influences or pH variations. Polyamine N-oxide-containing polymers simultaneously act as enzyme stabilizers and as color transfer inhibitors. Other polymeric stabilizers are linear $C_8$-$C_{18}$ polyoxyalkylenes. Alkylpolyglycosides can also stabilize the enzymatic components of the composition according to the invention and are preferably able additionally to increase these in their performance. Crosslinked N-containing compounds preferably fulfill a dual function as soil release agents and as enzyme stabilizers. Hydrophobic, nonionic polymer in particular stabilizes an optionally contained cellulase.

Reductants and antioxidants increase the stability of the enzymes to oxidative disintegration; sulfur-containing reductants, for example, are common for this. Other examples are sodium sulfite and reducing sugar.

Combinations of stabilizers, for example of polyols, boric acid and/or borax, the combination of boric acid or borate, reducing salts and succinic acid or other dicarboxylic acids or the combination of boric acid or borate with polyols or polyamino compounds and with reducing salts are particularly preferably employed. The action of peptide aldehyde stabilizers is more favorably increased by the combination with boric acid and/or boric acid derivatives and polyols and still further by the additional action of divalent cations, such as, for example, calcium ions.

Since compositions according to the invention can be supplied in all conceivable forms, enzymes according to the invention, or proteins in all formulations expedient for the addition to the respective compositions, are respective embodiments of the present invention. These include, for example, liquid formulations, solid granules or capsules.

The encapsulated form is suggested in order to protect the enzymes or other ingredients from other constituents, such as, for example, bleaches, or in order to make possible a controlled release. Depending on the size of these capsules, a distinction is made according to milli-, micro- and nanocapsules, microcapsules being particularly preferred for enzymes. Such capsules are disclosed, for example, by the patent applications WO 97/24177 and DE 19918267. A possible encapsulation method consists in encapsulating the proteins, starting from a mixture of the protein solution with a solution or suspension of starch or a starch derivative, in this substance. Such an encapsulation process is described by the application WO 01/38471.

In the case of solid compositions, the proteins can be employed, for example, in dried, granulated and/or encapsulated form. They can be added separately, that is, as an individual phase, or with other constituents together in the same phase, with or without compaction. If microencapsulated enzymes are to be processed in solid form, the water can be removed from the aqueous solutions resulting from the workup using processes known from the prior art, such as spray drying, centrifuging or by resolubilizing. The particles obtained in this way customarily have a particle size between 50 and 200 µm.

The enzymes, and also the protein according to the invention starting from a protein obtainment and preparation carried out according to the prior art, can be added to liquid, gelatinous or pasty compositions according to the invention in concentrated aqueous or nonaqueous solution, suspension or emulsion, but also in gel form or encapsulated or as a dried powder.

Detergents or cleaners according to the invention of this type are as a rule prepared by simple mixing of the ingredients, which can be added to an automatic mixer in substance or as a solution.

In addition to the primary washing performance, the proteases contained in detergents can further fulfill the function of activating other enzymatic constituents by proteolytic cleavage or inactivating after an appropriate time of action, i.e., as has been disclosed, for example, in applications WO 94/29426 or EP 747471. Comparable regulatory functions are also possible by means of the protein according to the invention. One embodiment of the present invention is furthermore those compositions containing capsules of protease-sensitive material, which, for example, are hydrolyzed by proteins according to the invention at an intended point in time and release their contents. A comparable effect can also be achieved with other multiphase compositions.

A further embodiment is compositions for the treatment of textile raw materials or for textile care which contain an alkaline protease according to the invention.

A further embodiment is compositions for the treatment of fibers or textiles containing natural constituents, in particular of those containing wool or silk.

Natural fibers in particular, such as wool or silk, are distinguished by a characteristic, microscopic surface structure. This can lead long-term to undesired effects, as has been explained in the example of wool in the article by R. Breier in *Melliand's Textilberichte* [Melliand's Textile Reports] of 4.1.2000 (p. 263), such as felting. To avoid such effects, the natural raw materials are treated with compositions according to the invention, which, for example, contribute to smoothing the scaly surface structure based on protein structures and thus counteract felting.

In a preferred embodiment, the composition is conceived using a protease according to the invention such that it can be used regularly as a care composition, for example by adding it to the washing process, using it after washing or applying it independently of washing. The desired effect consists in obtaining a smooth surface structure of the textile over a long period of time and/or preventing and/or reducing damage to the fabric.

A separate subject of the invention is methods for the mechanical cleaning of textiles or of hard surfaces, in which an alkaline protease according to the invention becomes active at least in one of the method steps.

Among these, those methods are preferred in which the alkaline protease according to the invention is employed in an amount from 40 μg to 4 g, preferably from 50 μg to 3 g, particularly preferably from 100 μg to 2 g and very particularly preferably from 200 μg to 1 g per application. Included are all integral and nonintegral values in each case lying between these numbers.

Under this fall both manual and mechanical methods, mechanical methods being preferred on account of their more precise controllability, as far, for example, as the amounts employed and times of action are concerned.

Methods for the cleaning of textiles are in general distinguished in that in a number of method steps various cleaning-active substances are applied to the article to be cleaned and, after the time of action, are washed off, or in that the article to be cleaned is treated in another way with a detergent or a solution of this composition. The same applies for methods for the cleaning of all other materials than textiles which are summarized under the term hard surfaces. All conceivable washing or cleaning methods can be enriched in at least one of the method steps by proteins according to the invention, and are then embodiments of the present invention.

Since preferred enzymes according to the invention naturally already have a protein-dissolving activity and also display this in media which otherwise have no cleaning power, such as, for example, in mere buffer, an individual substep of such a method for the mechanical cleaning of textiles can consist in applying an enzyme according to the invention as the only cleaning-active component, if desired, in addition to stabilizing compounds, salts or buffer substances. This is a particularly preferred embodiment of the present invention.

In a further preferred embodiment of such methods, the alkaline protease according to the invention concerned is prepared within the scope of one of the abovementioned recipes for compositions according to the invention, preferably detergents, or cleaners, according to the invention.

Preferred embodiments of this subject of the invention are methods for the treatment of textile raw materials or for textile care, in which in at least one of the method steps an alkaline protease according to the invention becomes active.

Among these, methods for textile raw materials, fibers or textiles containing natural constituents are preferred, and very particularly for those containing wool or silk.

In this case, for example, this can be methods in which materials for processing to textiles are prepared, for example for antifelt finishing, or, for example, methods which enrich the cleaning of worn textiles by a caring component. Because of the action described above of proteases on natural, protein-containing raw materials, in preferred embodiments these are methods for the treatment of textile raw materials, fibers or textiles containing natural constituents, in particular containing wool or silk.

An individual subject of the invention is the use of an alkaline protease according to the invention described above for the cleaning of textiles or of hard surfaces.

Accordingly, the abovementioned concentration ranges apply for these uses.

Proteases according to the invention can be used, in particular according to the properties described above and to the methods described above in order to eliminate protein-containing impurities from textiles or from hard surfaces. Embodiments are, for example, the hand wash, the manual removal of spots from textiles or from hard surfaces or the use in connection with a mechanical method.

In a preferred embodiment of this use, the alkaline proteases according to the invention concerned are prepared in the scope of one of the abovementioned recipes for compositions according to the invention, preferably detergents, or cleaners.

A further embodiment of this subject of the invention is the use of an alkaline protease according to the invention for the activation or deactivation of ingredients of detergents or cleaners.

As is known, protein constituents of detergents or cleaners can be inactivated by the action of a protease. To employ this otherwise rather undesired effect is a subject of the present invention. Likewise, it is possible as described above that by proteolysis, another component is first activated, for example if it is a hybrid protein of the actual enzyme and the inhibitor appropriate therefor, as has been disclosed, for example, in the application WO 00/01831 A2. Another example of such a regulation is that in which an active component, for the protection or for the control of its activity, is present encapsulated in a material which is attacked by proteolysis. Proteins according to the invention can thus be used for inactivation, activation or release reactions, in particular in multiphase compositions.

Corresponding to what has been said above, the following uses are also embodiments of the present invention:

The use of an alkaline protease according to the invention for the preparation or treatment of raw materials or intermediates in textile production, in particular for the removal of protective layers on fabrics;

the use of an alkaline protease according to the invention for the treatment of textile raw materials or for textile care and among these preferably the corresponding use for textile raw materials, fibers or textiles containing natural constituents and very particularly for those containing wool or silk.

The present invention is also realized in the form of those compositions comprising an alkaline protease according to the invention, which are cosmetics. Among these, all types of cleaning and caring compositions for human skin or hair are understood, in particular cleaning compositions.

Proteases also play a crucial role in the cell renewal process of the human skin (desquamation) (T. Egelrud et al., *Acta Derm. Venerol.*, Vol. 71 (1991), pp. 471-474). Accordingly, proteases are also used as bioactive components in skincare compositions in order to assist the breakdown of the desmosome structures which are increased in dry skin. The use of subtilisin proteases with amino acid replacements in positions R99GA/S, S154D/E and/or L211D/E for cosmetic purposes is described, for example, in WO 97/07770 A1. Corresponding to what has been said above, proteases according to the invention can be further developed by means of the corresponding point mutations. Thus proteases according to the invention are also suitable, in particular those which, for example, after mutagenesis or by addition of corresponding substances interacting with them, are controlled in their activity, as active components in skin- or hair-cleaning or care compositions. Those preparations of these enzymes are particularly preferred which, as described above, for example by coupling to macromolecular carriers (compare U.S. Pat. No. 5,230,891) are stabilized and/or derivatized by point mutations in highly allergenic positions such that they have a higher skin compatibility for humans.

Accordingly, corresponding cosmetic cleaning and care methods and the use of proteolytic enzymes of this type for cosmetic purposes are also included in this subject of the invention, in particular in corresponding compositions, such as, for example, shampoos, soaps or washing lotions, or in care compositions which are supplied, for example, in the form of creams. The use in a peeling pharmaceutical, or for its production, is also included in this claim.

In addition to the use in detergents and cleaners and cosmetics, numerous possibilities of application of proteases, in particular subtilases, are established in the prior art. The handbook *Industrial enyzmes and their applications* by H. Uhlig, Wiley-Verlag, New York (1998) presents an overview of this. All these techniques can be enriched by alkaline proteases according to the invention. Should it emerge that they can be further developed by the use of proteases according to the invention, these are included in the scope of protection of the present invention. This includes, in particular, the following areas of use:

the use of an alkaline protease according to the invention for the biochemical analysis or for the synthesis of low molecular weight compounds or of proteins;

among these preferably the use for the end group determination in the scope of a peptide sequence analysis;

the use of an alkaline protease according to the invention for the preparation, purification or synthesis of natural substances or biological valuable substances, preferably within the scope of corresponding compositions or methods;

the use of an alkaline protease according to the invention for the synthesis of proteins or other low molecular weight chemical compounds;

the use of an alkaline protease according to the invention for the treatment of natural raw materials, in particular for surface treatment, very particularly in a method for the treatment of leather, preferably within the scope of corresponding compositions or methods;

the use of an alkaline protease according to the invention for the treatment of photographic films, in particular for the removal of gelatin-containing or similar protective layers; and the use of an alkaline protease according to the invention for the preparation of foods or of feeds.

In principle, is comprised in the present application any technical field, which is enriched by the novel alkaline proteases presented hereby or methods or uses based hereon.

The following examples illustrate the present invention without restricting it thereto.

EXAMPLES

All molecular biological working steps follow standard methods, such as are indicated, for example, in the handbook by Fritsch, Sambrook and Maniatis, *Molecular cloning: a laboratory manual*, Cold Spring Harbour Laboratory Press, New York (1989), or comparable relevant works. Enzymes and kits were employed according to the instructions of the respective manufacturers.

Example 1

Obtainment of Cell Material from Soil Habitats

Soil samples were taken from various locations in Germany, taken up in water and suspended substances were sedimented by allowing to stand for 30 minutes. The supernatant was plated out on 5% strength agar plates using HSP10 solid medium (0.1 g of yeast extract, Difco, Heidelberg; 0.1 g of casein peptone, tryptically digested, Difco; 0.1 g of soluble starch (Merck, Order No. 1.01251); 2 g of $Na_2CO_3$; to 1000 ml of distilled water; pH10) and cultured at 30° C. for about 2 weeks. The bacterial lawn obtained was recovered mechanically from the agar surface.

Example 2

Arrangement of an Expression Gene Bank

The expression system chosen was the vector pUC18 (GenBank, National Institutes of Health, Bethesda, Md., USA; accession number L08752; FIG. 3) in *Escherichia coli* DH12S. This vector carries the β-galactosidase promoter of the lac operon inducible by addition of IPTG, so that in these cells a hereby controlled expression of the DNA integrated in the multiple cloning site is possible. The strain DH12S is suitable because of its laclq genotype for the IPTG induction and advantageous for a protease activity screening, because it has a sufficiently low endogenous proteolytic activity. Preliminary experiments had shown that *E. coli* JM109 also fulfills the same requirements.

The workup of the DNA from the sample obtained according to example 1 was carried out according to Zhou et al., *Appl. Environ. Microbiol.*, Vol. 62 (1996), pp. 316-322. This purified metagenomic DNA (see below) was subjected to a preparative partial restriction using the restriction enzyme Alu I for the preparation of fragment sizes in the range from 2 to 10 kb.

For this, first the optimum restriction incubation period was determined by recording enzyme kinetics. For this, 2.8 μg of the DNA preparation were incubated at 37° C. in the appropriate reaction buffer supplied by the manufacturer of Alu I (New England Biolabs, Schwalbach, Germany; Catalog No. R0137S). By addition of 0.2 U of Alu I per μg of DNA, the reaction was started in a total volume of 21 μl and then in two-minute intervals in each case 1.5 μl were taken from the batch, in which in each case the reaction was ended immediately by addition of 10 mM Tris/HCl, pH 7.0; 20% glycerol; 0.1% SDS and cooling to 0° C. By subsequent analysis on a 0.7% strength agarose gel, the optimum restriction period for a partial digestion was determined. For the isolation of the DNA isolated according to Example 1, it is about 6 to 7 minutes in order to obtain fragments in the size range from 2 to 10 kb.

The preparative partial digestion was accordingly carried out in 30 parallel batches. After appropriate stopping of the reaction, the batch was electrophoretically separated on a preparative 0.7% strength agarose gel, the gel region containing DNA of the sizes 2 to 10 kb was excized and this was isolated by means of electroelution in dialysis tubing at 4° C. The DNA was finally precipitated with 1/10 volume of 3 M Na acetate and the 2.5-fold volume of ethanol and taken up in an adequate volume. For the further separation of any possible present smaller DNA fragments, the gel electrophoresis, electroporation and precipitation were repeated.

440 ng of the fragmented metagenomic DNA thus obtained were ligated overnight at 16° C. in a total volume of 15 μl with 150 ng of the vector pUC18 with addition of 400 NEB units of T4-DNA ligase in 1× ligase buffer. This vector had been linearized beforehand with Sma I and dephosphorylated with alkaline phosphatase from calf thymus.

The transformation of competent *E. coli* DH12S cells (Gibco Life Technologies, Karlsruhe, catalog number 18312017) was carried out by means of electro-transformation. For this, 1 µl of ligation batch and 25 µl of cells were mixed, incubated on ice in an electroporation cuvette for 1 min and treated in the electroporator (BTX® ECM630, Genetronics Inc. San Diego, Calif., USA) according to the manufacturer's instructions. After immediate transfer to 1 ml of SOC medium (2% Bacto-tryptone; 0.5% yeast extract; 10 mM NaCl; 2.5 mM KCl; pH 7.0, adjusted with NaOH; autoclaved; supplemented with 10 mM $MgSO_4$ and $MgCl_2$ and 20 mM D(+)glucose), a recovery phase of 1 h at 37° C. and as in Example 1 plating onto agar plates with HSP10 solid medium followed.

Example 3

Screening for Proteolytic Activity

For the investigation of the quality of the gene bank prepared according to Example 2 in *E. coli* DH12S, the number of primary transformants produced altogether and the number of insert-carrying clones was determined by means of blue/white selection in a test plating. For this, 1 and 10 µl each of the transformation batch were plated out on 5% strength agar plates with LB medium (10 g of tryptone, 5 g of yeast extract, 5 g of NaCl, 1 ml of 1 N NaOH per 1), which was additionally treated with 100 µg/ml ampicillin, 0.2 mM (or 4 µg/ml) IPTG and 0.2 mM (or 1 µg/ml) X-Gal, and incubated overnight at 37° C. From 10 white colonies, that is, transformants, the plasmids were isolated by means of minipreparation (kit from Qiagen, Hilden, Germany), a restriction digestion was carried out using the restriction enzymes Sac I and Hind III for the excision of the insert (compare FIG. 3) and the fragments were separated on a 0.7% strength agarose gel. In fact, all vectors contained inserts of about 2 to 10 kb size.

The screening of the gene bank produced according to Example 2 was carried out on 5% strength agar plates 14 cm in diameter using LB medium ampicillin/IPTG/X-Gal (see above) and additionally 2% skimmed milk powder (Skim Milk, Difco, Order No. 232100). On 10 of these selection agar plates, corresponding to the titer of the bank volumes of the transformation batch of in each case about 10 000 cfu were uniformly plated out by means of glass beads (primary plating).

After incubation at 37° C. for 16 hours, the plates were incubated for up to two weeks at 28° C. During this time, protease-forming clones revealed themselves by means of clarification halos in the turbid substrate. A separate cell lysis for the detection of nonexported proteases was not necessary. The validation of the plasmid-mediated protease formation was carried out by fresh isolation of the primary clones and subsequently by isolation of the relevant insert-containing pUC18 vectors, retransformation and fresh screening (as above; secondary plating). The transformants following from this likewise showed halo formation on skimmed milk medium and thus confirmed the location of a protease gene on the DNA fragment cloned in each case.

Example 4

Sequence Analysis of a Proteolytically Active Clone
(HP70 Pa_2)

From a protease-positive clone having the designation HP70 Pa_2 obtained according to Example 3, the plasmid DNA was isolated according to standard methods, the insert was prepared by means of Sac I/Hind III digestion (see above) and sequenced according to standard methods. Here, first the primers specific for the vector and flanking the insert according to SEQ ID NO. 1 and 2 having the designations M13f and M13r were used, followed by the "primer walking", as is known from the prior art (R. J. Kaiser et al., "Specific primer-directed DNA sequencing using automated fluorescence detection"; *Nucl. Acids Res.*, 17 (15) (1989), pp. 6087-6102).

The sequencing of this clone afforded a region having an open reading frame whose DNA sequence is indicated in SEQ ID NO. 3. On account of its origin, it is noted as the organism "unknown" there and it is additionally stated that this sequence is to be attributed to a DNA isolate. Furthermore, on account of the present data (in particular by means of sequence comparisons, see below) it has to be assumed that the nucleotide positions 1 to 96 code for the signal peptide and altogether the coding region extends from 1 to 1746. SEQ ID NO. 4 discloses the amino acid sequence derived herefrom, having the same data with respect to the origin.

As the nearest similar enzyme described, an extracellular serine protease (E.C. 3.4.21.-) from *Xanthomonas campestris* pv. *campestris* (ATCC 33913) was found, which at GenBank (National Center for Biotechnology Information NCBI, National Institutes of Health, Bethesda, Md., USA) carries the accession number NP_636242. The homology at the amino acid level determined by means of the computer program Vector NTI® Suite 7.0, obtainable from InforMax, Inc., Bethesda, USA, with the specified default parameters is 75.0% identity to HP70. Further proteins found in this search, which at the amino acid level still appear the most similar, are compiled in Table 1 below.

TABLE 1

Nearest similar sequences to HP70 found at the amino acid level

| Accession Number | Description | Identity (%) |
|---|---|---|
| NP_636242 | extracellular protease from *Xanthomonas campestris* pv. *campestris*, strain ATCC 33913 | 75.0 |
| NP_641280 | extracellular protease from *Xanthomonas axonopodis* pv. *citri* strain 306 | 73.5 |
| NP_641281 | extracellular protease from *Xanthomonas axonopodis* pv. *citri* strain 306 | 60.8 |
| NP_641282 | extracellular protease from *Xanthomonas axonopodis* pv. *citri* strain 306 | 60.8 |
| NP_636245 | extracellular protease from *Xanthomonas campestris* pv. *campestris* strain ATCC 33913 | 59.2 |

At the DNA level, an identity of 74.4% results to the gene of the extracellular serine protease (E.C. 3.4.21.-) from *Xanthomonas campestris* pv. *campestris* (gene ID XCC0851).

Thus, the protease found is most highly probably likewise a serine protease. A homology of 26.2% identity to the established *B. lentus* alkaline protease (WO 92/21760 A1) results at the amino acid level and an identity of 33.6% at the nucleic acid level.

The associated vector having the designation 70-pUC (AWB403) was deposited on 10.2.2003 at the Deutsche Sammlung von Mikroorganismen and Zellkulturen GmbH, Mascheroder Weg 1b, 38124 Brunswick and there carries the deposit number DSM 15977. The protease encoded hereby is designated as HP70.

Example 5

Sequence Analysis of a Proteolytically Active Clone
(HP53Pa_2)

From a further protease-positive clone having the designation HP53Pa_2 obtained according to Example 3, the insert was prepared and sequenced as in Example 4. The sequences obtained are shown in SEQ ID NO. 6 and 7. On account of its origin, it is noted there as organism "unknown" and it is additionally indicated that these sequences are to be attributed to a DNA isolate. Furthermore, on account of the present data (in particular by means of sequence comparisons, see below) it has to be assumed that the nucleotide positions 1 to 114 code for the signal peptide and altogether the coding region extends from 1 to 1761.

It is in turn a subtilisin protease, which at the amino acid level has a homology of 75.4% identity to the extracellular serine protease (E.C. 3.4.21.-) from *Xanthomonas campestris* pv. *campestris* (ATCC 33913; see above) determined also in this case as the nearest similar. Further proteins found in this search which at the amino acid level still appear to be the most similar are compiled in table 2 below.

TABLE 2

Nearest similar sequences found to HP53 at the amino acid level

| Accession Number | Description | Identity (%) |
|---|---|---|
| NP_636242 | extracellular protease from *Xanthomonas campestris* pv. *campestris* strain ATCC 33913 | 75.4 |
| NP_641280 | extracellular protease from *Xanthomonas axonopodis* pv. *citri* strain 306 | 72.6 |
| NP_641281 | extracellular protease from *Xanthomonas axonopodis* pv. *citri* strain 306 | 59.3 |
| NP_641282 | extracellular protease from *Xanthomonas axonopodis* pv. *citri* strain 306 | 59.8 |
| NP_636245 | extracellular protease from *Xanthomonas campestris* pv. *campestris* strain ATCC 33913 | 59.0 |

At the DNA level, an identity of 75.0% results to the gene of the extracellular serine protease (E.C. 3.4.21.-) from *Xanthomonas campestris* pv. *campestris*.

At the amino acid level a homology of 25.9% identity and at the nucleic acid level an identity of 33.5% result to the established *B. lentus* alkaline protease (WO 92/21760 A1).

The associated vector having the designation 53-pUC (AWB403) was deposited on 10.2.2003 at the Deutsche Sammlung von Mikroorganismen und Zellkulturen GmbH, Mascheroder Weg 1b, 38124 Brunswick and there carries the deposit number DSM 15976. The protease encoded hereby is designated as HP53.

Example 6

Production of C-Terminal Deletion Mutants of HP70 and HP53

HP70dc

C'-terminally, 332 bp were deleted from the protease of the clone having the designation HP70Pa_2 obtained according to Example 3 and described in Example 4. This amino acid sequence HP70_deltaC is shown in SEQ ID NO. 5. On account of its construction, it is noted there that it is a synthetic sequence, concretized with the detail "DNA isolate, Delta C". According to SEQ ID NO. 3 and 4, the section of positions 1 to 32 can in turn be considered as a signal peptide.

For this, a 1413 by size DNA piece is generated from the DNA indicated in SEQ ID NO. 3 using the oligonucleotides HP70f (SEQ ID NO. 10) and HP70r (SEQ ID NO. 11) as primers under standard PCR conditions. After processing the fragment obtained with the endonucleases EcoRI and BamHI, the fragment is cloned into the corresponding cleavage sites of the *E. coli* expression vector pUC18 and transformed in a suitable strain (for example *E. coli* DH12S). From the transformants obtained, by blue/white selection the desired candidate can be identified, actively expressed and thus obtained in a sufficient amount for further investigations.

HP53dc

C'-terminally, 330 by were deleted from the protease of the clone having the designation HP53Pa 2 obtained according to Example 3 and described in Example 5. This amino acid sequence HP53_deltaC is shown in SEQ ID NO. 8.

For this, a 1303 by size DNA piece is generated from the DNA indicated in SEQ ID NO. 6 using the oligonucleotides HP53f (SEQ ID NO. 12) and HP53r (SEQ ID NO. 13) as primers under standard PCR conditions. After processing the fragment obtained using the endonucleases BlpI and BamHI, the fragment is cloned into the corresponding cleavage sites of the *E. coli* expression vector pUC18_HP70_dc obtained above in the first part of the example, which has been processed beforehand using the same endonucleases.

After transformation in a suitable strain (for example *E. coli* DH12S), the desired candidate can be identified, actively expressed and thus obtained in an adequate amount for further investigations from the transformants obtained by restriction analysis using SacII (pUC_HP53_dc contains such a cleavage site).

On account of this construction, it is noted in SEQ ID NO. 8 that it is, as in the case of SEQ ID NO. 5, a synthetic sequence, concretized with the detail "DNA isolate, Delta C". Furthermore, the section of positions 1 to 32 according to SEQ ID NO. 5 was introduced here, such that this has to be considered as a signal peptide of HP70.

Example 7

Quantitative Obtainment of the Proteases According to the Invention and Their Biochemical Characterization The expression clones obtained according to Examples 3 to 6 were taken up in 100 ml of LB medium (10 g/l tryptone, 5 g/l, yeast extract, 10 g/l NaCl) and cultured in a 500 ml Erlenmeyer flask at 37° C. and with shaking at 200 rpm.

Subsequently, they were biochemically characterized. Here, the proteolytic activity was determined by means of an "MTP assay", which is based on a fluorescence-coupled casein substrate (BODIPY® FL Conjugate, Molecular Probes, Göttingen, Germany; Order No. #6638), to which fluorophors (emitters) and dampers (quenchers) are coupled. In the intact substrate, fluorescence of the emitters is suppressed by the quenchers. On hydrolysis of the casein, the oligopeptides with the groups coupled to them move away from one another and on corresponding excitation fluorescence emission occurs, whose intensity is thus a measure of the proteolysis.

For the activity determination, in each case 5 µl of a protease sample according to example 5 are incubated in 100 mM Tris/HCl having the desired pH and 4.5 µg/ml BODIPY® FL Conjugate I in a total volume of 100 µl for 1 h at the temperature of interest. All measurements indicated below were carried out in 96-well microtiter plates (Opaque® Plates, black; Corning BV Life Sciences, Schiphol-Rijk, Netherlands; Order No. #3915) with the aid of a FLUOstar® fluorescence measuring apparatus (BMG Lab Technologies, Offenburg, Germany).

pH and Temperature Optimum

For the protease HP53 shown in SEQ ID NO. 7, the following biochemical parameters result: pH optimum at 37° C.: 8.6 and temperature optimum at pH 8.6: 37° C.

Influence of Complexing Agents

The influence of complexing agents was investigated by addition of 1 mM EDTA at pH 8.6 in the assay indicated above, namely at 37° C. and 50° C. The measured value without addition of EDTA was set at 100%. In contrast, the relative proteolytic activity at 50° C. was 27% and at 37° C. was 10%.

Stability Measurement

For measurement of the stability, the protease sample employed was first preincubated for 15 min at 50° C. in 50 mM $NaHCO_3$ buffer, pH 10.9 and then the residual activity in the abovementioned assay was measured at 37° C. and 50° C. at pH 8.6 in each case. Here, the activity of the same extract without preincubation but otherwise identical treatment was in each case set at 100%. In this way, a residual activity of 11% was determined for 37° C. and of 13% for 50° C.

These are thus molecules which are relatively stable to high pHs, and this even nearly independently of the temperature.

Example 8

Contribution of the Protease HP70 According to the Invention to the Washing Performance at Relatively Low Temperature For this example, standardized textiles provided with soilings were employed, which had been ordered from Eidgenossische Material-Prufungs-und-Versuchsanstalt, St. Gallen, Switzerland (EMPA). In this case, the following soilings and textiles were used: A (blood/milk/drawing ink on cotton), B (blood/milk/drawing ink on a polyester-cotton mixed fabric) and C (egg/soot on cotton).

Using this test material, various detergent recipes were investigated launderometrically for their washing performance. For this, in each case a liquor ratio of 1:12 was set and washing was carried out for 30 min at a temperature of 40° C. The dosage was 5.9 g of the respective composition per 1 of washing liquor. The water hardness was 16° German hardness.

The control detergent used was a detergent basis recipe of the following composition (all data in percent by weight): 4% linear alkylbenzenesulfonate (sodium salt), 4% $C_{12}$-$C_{18}$ fatty alcohol sulfate (sodium salt), 5.5% $C_{12}$-$C_{18}$ fatty alcohol with 7EO, 1% sodium soap, 11% sodium carbonate, 2.5% amorphous sodium disilicate, 20% sodium perborate tetrahydrate, 5.5% TAED, 25% zeolite A, 4.5% polycarboxylate, 0.5% phosphonate, 2.5% foam inhibitor granules, 5% sodium sulfate, remainder: water, optical brightener, salts.

It was treated in parallel batches in each case activity-identically with the protease according to the invention and a control protease. For the control, the B. lentus alkaline protease F49 (WO 95/23221 A1; manufacturer: Biozym, Kundl, Austria) was used. This had a (determinable according to the method indicated in the description) specific activity of about 200 000 PE/g, whereby with 0.2% by weight an F49 concentration of about 40,000 PE per 100 g of the composition and an activity of about 2400 PE per 1 of washing liquor resulted. Recipes were additionally prepared which, dispensing with a corresponding amount of salts, in each case contained 0.5%, that is the two and a half-fold amount of protease. The protease according to the invention was added to the same base recipe in the same activity concentrations. In this regard, the % by weight values indicated for F49 in the table below are correct and apply for HP70 by way of approximation.

After washing, the degree of whiteness of the washed textiles was measured in comparison to that of barium sulfate, which had been standardized to 100%. The measurement was carried out on a Datacolor SF500-2 spectrometer at 460 nm (UV trap filter 3), 30 mm diaphragm, without gloss, light type D65, 10°, d/8°. The results obtained are compiled as percent reflection, that is, as percentages in comparison to barium sulfate together with the respective initial values in table 3 below. The mean values from in each case three measurements are indicated. They allow an immediate conclusion on the contribution of the enzyme present to the washing performance of the composition used.

TABLE 3

Contribution of the protease HP70 according to the invention to the washing performance at a temperature of 40° C.

| Base detergent containing | A | B | C |
|---|---|---|---|
| Initial value | 14.1 | 12.8 | 28.9 |
| Control without protease | 18.9 | 16.0 | 51.3 |
| 0.2% HP70 | 26.7 | 26.5 | 68.3 |
| 0.2% B. lentus alkaline protease F49 | 25.7 | 25.6 | 68.1 |
| 0.5% HP70 | 33.4 | 29.8 | 68.4 |
| 0.5% B. lentus alkaline protease F49 | 30.0 | 32.2 | 70.2 |
| Standard dev. | 1.3 | 1.3 | 1.8 |

All three measuring series verify that the protease HP70 according to the invention compared to protease-free detergents affords an improvement in the washing performance on protein-containing soilings. That is, it also displays a proteolytic activity in the presence of denaturing agents such as, for example, surfactants. The values determined for the B. lentus alkaline protease F49, a molecule optimized for this use area by means of point mutagenesis (compare WO 95/23221 A1) verify the correctness of the test procedure. In the measuring series A and at the lower concentration in measuring series B, HP70 exceeded even the results for F49; the other values are comparable to those for F49.

Example 9

Contribution of the Protease HP53 According to the Invention to the Washing Performance at Relatively Low Temperature The previous test was repeated using the protease HP53 according to the invention. The conditions were the same. However, the performance was determined on the soiling D instead of on the soiling C (blood on cotton). The result is compiled in Table 4 below.

TABLE 4

Contribution of the protease HP53 according to the invention to the washing performance at a temperature of 40° C.

| Base detergent containing | A | B | C |
|---|---|---|---|
| Initial value | 13.5 | 13.9 | 18.8 |
| Control without protease | 20.1 | 18.7 | 67.3 |
| 0.2% HP53 | 48.1 | 60.7 | 73.7 |
| 0.2% B. lentus alkaline protease F49 | 25.5 | 27.9 | 69.7 |
| 0.5% HP53 | 42.9 | 53.5 | 69.0 |
| 0.5% B. lentus alkaline protease F49 | 32.6 | 41.1 | 73.8 |
| Standard dev. | 4.5 | 1.7 | 2.4 |

These measuring series verify that the protease HP53 according to the invention also affords an improvement of the washing performance on protein-containing soilings compared to protease-free detergents. That is, it also displays a proteolytic activity in the presence of denaturing agents such as, for example, surfactants or bleach. The values determined are comparable at least to those for the *B. lentus* alkaline protease F49, even distinctly superior in the measuring series A and B.

Example 10

Contribution of the Protease HP53dc According to the Invention to the Washing Performance at Relatively Low Temperature As in the preceding two Examples, the variant HP53dc was also investigated with respect to its performance contribution with regard to the soilings A, B and C. The conditions were again the same. The result is compiled in Table 5 below.

TABLE 5

Contribution of the protease HP53dc according to the invention to the washing performance at a temperature of 40° C.

| Base detergent containing | A | B | C |
|---|---|---|---|
| Initial value | 14.6 | 13.2 | 28.1 |
| Control without protease | 19.6 | 16.2 | 54.0 |
| 0.2% HP53dc | 42.8 | 41.2 | 71.2 |
| 0.2% *B. lentus* alkaline protease F49 | 26.8 | 31.2 | 70.0 |
| 0.5% HP53dc | 48.6 | 50.0 | 70.8 |
| 0.5% *B. lentus* alkaline protease F49 | 29.8 | 40.7 | 70.9 |
| Standard dev. | 1.6 | 1.9 | 2.5 |

These measuring series verify that the protease HP53dc according to the invention also affords an improvement of the washing performance on protein-containing soilings compared to protease-free detergents. That is, it displays a proteolytic activity even in the presence of denaturing agents such as, for example, surfactants or bleach. The values determined in the measuring series A and B are clearly superior to those for the *B. lentus* alkaline protease F49 and in series C at least comparable.

Example 11

Contribution of the Protease HP53dc According to the Invention to the Washing Performance at Relatively High Temperature The preceding test was repeated with HP53 on the two soilings A and B at a washing temperature of 60° C. under otherwise identical conditions. The result is compiled in table 6 below.

TABLE 6

Contribution of the protease HP53dc according to the invention to the washing performance at a temperature of 60° C.

| Base detergent containing | A | B |
|---|---|---|
| Initial value | 14.6 | 13.2 |
| Control without protease | 20.5 | 16.7 |
| 0.2% HP53dc | 36.3 | 36.9 |
| 0.2% *B. lentus* alkaline protease F49 | 25.6 | 32.4 |
| 0.5% HP53dc | 47.7 | 48.0 |
| 0.5% *B. lentus* alkaline protease F49 | 31.4 | 43.5 |
| Standard dev. | 1.7 | 1.3 |

Even at the temperature of 60° C., in the measuring series A and B the superiority of the protease HP53dc according to the invention to the *B. lentus* alkaline protease F49 is seen. Fortunately, the protease HP53dc according to the invention at 60° C. is not noticeably denatured, such that it is in particular suitable as a detergent protease.

We claim:

1. An isolated protein comprising an amino acid sequence which is at least 95% identical to SEQ ID NO: 7, wherein said sequence has alkaline protease activity.

2. The isolated protein of claim 1, wherein the sequence is at least 95% identical to the amino acid positions 39 to 586 of SEQ ID NO. 7.

3. The isolated protein of claim 1, said sequence being obtained by insertion mutagenesis or by substitution mutagenesis.

4. The isolated protein of claim 1 which is additionally stabilized.

5. The isolated protein of claim 1, which is additionally derivatized.

6. A composition comprising the isolated protein of claim 1.

7. The composition of claim 6, which is a detergent or cleaner.

8. The composition of claim 7 wherein the isolated protein is present in an amount from about 2 μg to 20 mg per gram of the composition.

9. The composition of claim 8, wherein the isolated protein is present in an amount from about 50 μg to 10 mg per gram of the composition.

10. The composition of claim 6, further comprising one or more enzymes, said one or more enzymes selected from the group consisting of proteases, amylases, cellulases, hemicellulases, oxidoreductases and lipases.

11. The composition of claim 7, which is a composition for the washing or cleaning of textile raw materials or fibers or textiles containing wool or silk.

12. An isolated protein, wherein the isolated protein comprises the amino acid sequence according to positions 39 to 586 of SEQ ID NO: 7.

13. An isolated fusion protein comprising the isolated protein of claim 1 which is further modified by fusion with at least one other protein.

* * * * *

```
                        SEQUENCE LISTING

<160> NUMBER OF SEQ ID NOS: 17

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      primer M13f

<400> SEQUENCE: 1
gtaaaacgac ggccag                                                        16

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer M13r

<400> SEQUENCE: 2
caggaaacag ctatgac                                                       17

<210> SEQ ID NO 3
<211> LENGTH: 1777
<212> TYPE: DNA
<213> ORGANISM: Unknown
<220> FEATURE:
<223> OTHER INFORMATION: Description of Unknown: DNA isolate,
```

```
            metagenomic DNA from soil sample
<220> FEATURE:
<221> NAME/KEY: sig_peptide
<222> LOCATION: (1)..(96)
<220> FEATURE:
<221> NAME/KEY: CDS
<222> LOCATION: (1)..(1743)

<400> SEQUENCE: 3 atg tct cat gat tcg caa ccc cgt ttg cgt cag cgt gca ttg gtt gta     48
Met Ser His Asp Ser Gln Pro Arg Leu Arg Gln Arg Ala Leu Val Val
1               5                   10                  15 ctc ggc gcg tcc gtc ctg tcc acc ctg ctg ctg gcc gcc ccg gca ttc     96
Leu Gly Ala Ser Val Leu Ser Thr Leu Leu Leu Ala Ala Pro Ala Phe
            20                  25                  30 gcc ggc gat gtg cag ctg agc ggc ttg tcg tcg gca ccg acg cac cag    144
Ala Gly Asp Val Gln Leu Ser Gly Leu Ser Ser Ala Pro Thr His Gln
        35                  40                  45 cgt ttc atc gtc aaa tac aag gat ggc gcc aac ctg gtc gcc acc ccg    192
Arg Phe Ile Val Lys Tyr Lys Asp Gly Ala Asn Leu Val Ala Thr Pro
    50                  55                  60 acc gca ctg gcc agc tcg ttg aag gcg gcg gcc tcg gcc gta ccg gct    240
Thr Ala Leu Ala Ser Ser Leu Lys Ala Ala Ala Ser Ala Val Pro Ala
65                  70                  75                  80 gcg cag ggt cgc gcg ctg ggc ctg cag aag ctg cgc cag ctg gcc att    288
Ala Gln Gly Arg Ala Leu Gly Leu Gln Lys Leu Arg Gln Leu Ala Ile
                85                  90                  95 ggg ccg acc gtg gtc aag gcc gac cgt ccg ctg gat gcg gcc gag tcg    336
Gly Pro Thr Val Val Lys Ala Asp Arg Pro Leu Asp Ala Ala Glu Ser
            100                 105                 110 gaa ctg ctg atg cgc cgc ctg gcg gcc gac ccg aac gtg gaa tac gtc    384
Glu Leu Leu Met Arg Arg Leu Ala Ala Asp Pro Asn Val Glu Tyr Val
        115                 120                 125 gaa gtc gat cag ctg atg cac gcc acc ctg gtg ccc aac gac gcg cgc    432
Glu Val Asp Gln Leu Met His Ala Thr Leu Val Pro Asn Asp Ala Arg
    130                 135                 140 ctg tcc gag cag tgg ggc ttc ggc acc agc aac gcc tcg atc aac gtg    480
Leu Ser Glu Gln Trp Gly Phe Gly Thr Ser Asn Ala Ser Ile Asn Val
145                 150                 155                 160 cgc ccg gca tgg gac aag gcc acc ggt acc ggc gtg gtg gtg gcg gtg    528
Arg Pro Ala Trp Asp Lys Ala Thr Gly Thr Gly Val Val Val Ala Val
                165                 170                 175 atc gac acc ggc atc acc aac cat ccg gac ctc aac gcc aac atc ctg    576
Ile Asp Thr Gly Ile Thr Asn His Pro Asp Leu Asn Ala Asn Ile Leu
            180                 185                 190 ccc ggc tat gac ttc atc agc gac gcg gcg atg gcg cgc gat ggt ggc    624
Pro Gly Tyr Asp Phe Ile Ser Asp Ala Ala Met Ala Arg Asp Gly Gly
        195                 200                 205 ggc cgt gac aac aac gcg aac gat gaa ggc gac tgg tac gcc gcc aac    672
Gly Arg Asp Asn Asn Ala Asn Asp Glu Gly Asp Trp Tyr Ala Ala Asn
    210                 215                 220 gag tgc ggc tcg ggc att ccg gcg tcg aac tcg agc tgg cac ggt acc    720
Glu Cys Gly Ser Gly Ile Pro Ala Ser Asn Ser Ser Trp His Gly Thr
225                 230                 235                 240 cac gta gcc ggc acc atc gcg gcg gtg acc aac aac agc act ggc gtg    768
His Val Ala Gly Thr Ile Ala Ala Val Thr Asn Asn Ser Thr Gly Val
                245                 250                 255 gcc ggt acg gca ttc aac gcg aag gtc gtg ccg gtg cgt gtg ctc ggc    816
Ala Gly Thr Ala Phe Asn Ala Lys Val Val Pro Val Arg Val Leu Gly
            260                 265                 270 aag tgc ggc ggt tac acc tcc gac atc gcc gat gcg atc gtg tgg gcc    864
Lys Cys Gly Gly Tyr Thr Ser Asp Ile Ala Asp Ala Ile Val Trp Ala
```

-continued

|   |   |   |   | 275 |   |   |   | 280 |   |   |   | 285 |   |   |   |      |
|---|---|---|---|---|---|---|---|---|---|---|---|---|---|---|---|------|
| tcc | ggc | ggc | acg | gtc | agc | ggc | gtg | ccg | gcc | aat | gcc | aac | ccg | gcc | gaa | 912 |
| Ser | Gly | Gly | Thr | Val | Ser | Gly | Val | Pro | Ala | Asn | Ala | Asn | Pro | Ala | Glu | |
| 290 | | | | | 295 | | | | 300 | | | | | | | |
| gtg | atc | aac | atg | tcg | ctg | ggc | ggt | ggc | acc | tgc | tcg | acc | acc | tac | | 960 |
| Val | Ile | Asn | Met | Ser | Leu | Gly | Gly | Gly | Thr | Cys | Ser | Thr | Thr | Tyr | | |
| 305 | | | | 310 | | | | | 315 | | | | | 320 | | |
| cag | aac | gcg | atc | aac | ggc | gcg | gtg | tcg | cgc | ggc | acg | acg | gtg | gtg | gtg | 1008 |
| Gln | Asn | Ala | Ile | Asn | Gly | Ala | Val | Ser | Arg | Gly | Thr | Thr | Val | Val | Val | |
| | | | | 325 | | | | | 330 | | | | | 335 | | |
| gcg | gcg | ggc | aac | agc | aac | acc | aac | gtg | tcc | tcg | tcg | gtg | ccg | gcc | aac | 1056 |
| Ala | Ala | Gly | Asn | Ser | Asn | Thr | Asn | Val | Ser | Ser | Ser | Val | Pro | Ala | Asn | |
| | | | 340 | | | | | 345 | | | | | 350 | | | |
| tgc | gcc | aac | gtg | atc | gcg | gtg | gcg | gcc | acg | acg | tcg | gcc | ggc | gcg | cgc | 1104 |
| Cys | Ala | Asn | Val | Ile | Ala | Val | Ala | Ala | Thr | Thr | Ser | Ala | Gly | Ala | Arg | |
| | | 355 | | | | | 360 | | | | | 365 | | | | |
| gcg | agc | ttc | tcg | aac | tac | ggt | gcg | ggc | atc | gat | att | tcg | gcg | ccg | ggc | 1152 |
| Ala | Ser | Phe | Ser | Asn | Tyr | Gly | Ala | Gly | Ile | Asp | Ile | Ser | Ala | Pro | Gly | |
| | 370 | | | | | 375 | | | | | 380 | | | | | |
| cag | gcg | atc | ctg | tcc | acg | ctc | aac | agc | ggt | acg | acg | gtg | ccg | ggc | acg | 1200 |
| Gln | Ala | Ile | Leu | Ser | Thr | Leu | Asn | Ser | Gly | Thr | Thr | Val | Pro | Gly | Thr | |
| 385 | | | | | 390 | | | | | 395 | | | | | 400 | |
| gcg | tcc | tac | gcg | tcc | tac | aac | ggg | acg | tcg | atg | gcg | gcg | ccg | cac | gtg | 1248 |
| Ala | Ser | Tyr | Ala | Ser | Tyr | Asn | Gly | Thr | Ser | Met | Ala | Ala | Pro | His | Val | |
| | | | | 405 | | | | | 410 | | | | | 415 | | |
| gcc | ggc | gtg | gtg | gcg | ctg | gtg | cag | tcg | gtg | gca | ccg | acg | gcg | ttg | acg | 1296 |
| Ala | Gly | Val | Val | Ala | Leu | Val | Gln | Ser | Val | Ala | Pro | Thr | Ala | Leu | Thr | |
| | | | 420 | | | | | 425 | | | | | 430 | | | |
| ccg | gcg | gcg | atc | gag | acg | ttg | ctg | aag | aac | acg | gca | cgg | gca | ttg | ccg | 1344 |
| Pro | Ala | Ala | Ile | Glu | Thr | Leu | Leu | Lys | Asn | Thr | Ala | Arg | Ala | Leu | Pro | |
| | | 435 | | | | | 440 | | | | | 445 | | | | |
| ggc | gca | tgc | agc | ggt | ggg | tgc | ggc | gcg | ggc | atc | gtg | gac | gcc | gat | gcg | 1392 |
| Gly | Ala | Cys | Ser | Gly | Gly | Cys | Gly | Ala | Gly | Ile | Val | Asp | Ala | Asp | Ala | |
| | 450 | | | | | 455 | | | | | 460 | | | | | |
| gcg | gtc | acg | gcg | gcg | ctg | ggc | ggg | acg | aat | ccg | aac | ccg | ggc | acg | ggg | 1440 |
| Ala | Val | Thr | Ala | Ala | Leu | Gly | Gly | Thr | Asn | Pro | Asn | Pro | Gly | Thr | Gly | |
| 465 | | | | | 470 | | | | | 475 | | | | | 480 | |
| acg | gtg | ctg | cag | aac | aat | gtg | ccg | gtg | agc | ggt | ctg | ggc | gcg | gcc | agc | 1488 |
| Thr | Val | Leu | Gln | Asn | Asn | Val | Pro | Val | Ser | Gly | Leu | Gly | Ala | Ala | Ser | |
| | | | | 485 | | | | | 490 | | | | | 495 | | |
| ggg | gca | tcg | ctg | tcc | tat | acg | gtg | gtg | gtg | ccg | tcg | ggc | cgt | tcg | cag | 1536 |
| Gly | Ala | Ser | Leu | Ser | Tyr | Thr | Val | Val | Val | Pro | Ser | Gly | Arg | Ser | Gln | |
| | | | 500 | | | | | 505 | | | | | 510 | | | |
| ctg | aag | gtg | agc | atc | gcc | ggt | ggc | agt | ggt | gat | gcg | gat | ctg | tac | gtg | 1584 |
| Leu | Lys | Val | Ser | Ile | Ala | Gly | Gly | Ser | Gly | Asp | Ala | Asp | Leu | Tyr | Val | |
| | | 515 | | | | | 520 | | | | | 525 | | | | |
| cgt | tcg | ggc | agc | gcg | ccg | acc | gac | acg | gtg | tac | aac | tgc | cgt | ccg | tac | 1632 |
| Arg | Ser | Gly | Ser | Ala | Pro | Thr | Asp | Thr | Val | Tyr | Asn | Cys | Arg | Pro | Tyr | |
| | 530 | | | | | 535 | | | | | 540 | | | | | |
| ctg | agc | ggc | aac | aac | gag | acc | tgc | acg | atc | act | tca | ccg | gcg | gcc | ggt | 1680 |
| Leu | Ser | Gly | Asn | Asn | Glu | Thr | Cys | Thr | Ile | Thr | Ser | Pro | Ala | Ala | Gly | |
| 545 | | | | | 550 | | | | | 555 | | | | | 560 | |
| acc | tgg | cac | gtg | cgg | gtg | aag | ggc | tac | tcg | acc | ttc | tcc | ggg | gtc | acc | 1728 |
| Thr | Trp | His | Val | Arg | Val | Lys | Gly | Tyr | Ser | Thr | Phe | Ser | Gly | Val | Thr | |
| | | | | 565 | | | | | 570 | | | | | 575 | | |
| ctg | acc | gcg | cag | tac | tgagcccaga tccctctcca atgggcacgc ccg | | | | | | | | | | | 1777 |
| Leu | Thr | Ala | Gln | Tyr | | | | | | | | | | | | |
| | | | | 580 | | | | | | | | | | | | |

<210> SEQ ID NO 4

```
<211> LENGTH: 581
<212> TYPE: PRT
<213> ORGANISM: Unknown
<220> FEATURE:
<223> OTHER INFORMATION: Description of Unknown: Polypeptide from
      DNA isolate, metagenomic DNA from soil sample

<400> SEQUENCE: 4
```

| | | | | | | | | | | | | | | |
|---|---|---|---|---|---|---|---|---|---|---|---|---|---|---|
|Met|Ser|His|Asp|Ser|Gln|Pro|Arg|Leu|Arg|Gln|Arg|Ala|Leu|Val|Val|
|1| | | |5| | | | |10| | | | |15|
|Leu|Gly|Ala|Ser|Val|Leu|Ser|Thr|Leu|Leu|Ala|Ala|Pro|Ala|Phe|
| | | |20| | | | |25| | | | |30| |
|Ala|Gly|Asp|Val|Gln|Leu|Ser|Gly|Leu|Ser|Ser|Ala|Pro|Thr|His|Gln|
| | |35| | | | |40| | | | |45| | |
|Arg|Phe|Ile|Val|Lys|Tyr|Lys|Asp|Gly|Ala|Asn|Leu|Val|Ala|Thr|Pro|
|50| | | | |55| | | | |60| | | | |
|Thr|Ala|Leu|Ala|Ser|Ser|Leu|Lys|Ala|Ala|Ser|Ala|Val|Pro|Ala|
|65| | | | |70| | | | |75| | | | |80|
|Ala|Gln|Gly|Arg|Ala|Leu|Gly|Leu|Gln|Lys|Leu|Arg|Gln|Leu|Ala|Ile|
| | | | |85| | | | |90| | | | |95| |
|Gly|Pro|Thr|Val|Val|Lys|Ala|Asp|Arg|Pro|Leu|Asp|Ala|Ala|Glu|Ser|
| | | |100| | | | |105| | | | |110| | |
|Glu|Leu|Leu|Met|Arg|Arg|Leu|Ala|Ala|Asp|Pro|Asn|Val|Glu|Tyr|Val|
| | |115| | | | |120| | | | |125| | | |
|Glu|Val|Asp|Gln|Leu|Met|His|Ala|Thr|Leu|Val|Pro|Asn|Asp|Ala|Arg|
| |130| | | | |135| | | | |140| | | | |
|Leu|Ser|Glu|Gln|Trp|Gly|Phe|Gly|Thr|Ser|Asn|Ala|Ser|Ile|Asn|Val|
|145| | | | |150| | | | |155| | | | |160|
|Arg|Pro|Ala|Trp|Asp|Lys|Ala|Thr|Gly|Thr|Gly|Val|Val|Ala|Val|
| | | | |165| | | | |170| | | | |175| |
|Ile|Asp|Thr|Gly|Ile|Thr|Asn|His|Pro|Asp|Leu|Asn|Ala|Asn|Ile|Leu|
| | | |180| | | | |185| | | | |190| | |
|Pro|Gly|Tyr|Asp|Phe|Ile|Ser|Asp|Ala|Ala|Met|Ala|Arg|Asp|Gly|Gly|
| | |195| | | | |200| | | | |205| | | |
|Gly|Arg|Asp|Asn|Ala|Asn|Asp|Glu|Gly|Asp|Trp|Tyr|Ala|Ala|Asn|
| |210| | | | |215| | | | |220| | | | |
|Glu|Cys|Gly|Ser|Gly|Ile|Pro|Ala|Ser|Asn|Ser|Ser|Trp|His|Gly|Thr|
|225| | | | |230| | | | |235| | | | |240|
|His|Val|Ala|Gly|Thr|Ile|Ala|Ala|Val|Thr|Asn|Asn|Ser|Thr|Gly|Val|
| | | | |245| | | | |250| | | | |255| |
|Ala|Gly|Thr|Ala|Phe|Asn|Ala|Lys|Val|Val|Pro|Val|Arg|Val|Leu|Gly|
| | | |260| | | | |265| | | | |270| | |
|Lys|Cys|Gly|Gly|Tyr|Thr|Ser|Asp|Ile|Ala|Asp|Ala|Ile|Val|Trp|Ala|
| |275| | | | |280| | | | |285| | | | |
|Ser|Gly|Gly|Thr|Val|Ser|Gly|Val|Pro|Ala|Asn|Ala|Asn|Pro|Ala|Glu|
|290| | | | |295| | | | |300| | | | | |
|Val|Ile|Asn|Met|Ser|Leu|Gly|Gly|Gly|Gly|Thr|Cys|Ser|Thr|Thr|Tyr|
|305| | | | |310| | | | |315| | | | |320|
|Gln|Asn|Ala|Ile|Asn|Gly|Ala|Val|Ser|Arg|Gly|Thr|Thr|Val|Val|Val|
| | | |325| | | | |330| | | | |335| | |
|Ala|Ala|Gly|Asn|Ser|Asn|Thr|Asn|Val|Ser|Ser|Val|Pro|Ala|Asn|
| | | |340| | | | |345| | | | |350| | |
|Cys|Ala|Asn|Val|Ile|Ala|Val|Ala|Ala|Thr|Thr|Ser|Ala|Gly|Ala|Arg|
| | |355| | | | |360| | | | |365| | | |
|Ala|Ser|Phe|Ser|Asn|Tyr|Gly|Ala|Gly|Ile|Asp|Ile|Ser|Ala|Pro|Gly|
| |370| | | | |375| | | | |380| | | | |

-continued

```
Gln Ala Ile Leu Ser Thr Leu Asn Ser Gly Thr Thr Val Pro Gly Thr
385                 390                 395                 400

Ala Ser Tyr Ala Ser Tyr Asn Gly Thr Ser Met Ala Ala Pro His Val
            405                 410                 415

Ala Gly Val Val Ala Leu Val Gln Ser Val Ala Pro Thr Ala Leu Thr
        420                 425                 430

Pro Ala Ala Ile Glu Thr Leu Leu Lys Asn Thr Ala Arg Ala Leu Pro
    435                 440                 445

Gly Ala Cys Ser Gly Gly Cys Gly Ala Gly Ile Val Asp Ala Asp Ala
450                 455                 460

Ala Val Thr Ala Ala Leu Gly Gly Thr Asn Pro Asn Pro Gly Thr Gly
465                 470                 475                 480

Thr Val Leu Gln Asn Asn Val Pro Val Ser Gly Leu Gly Ala Ala Ser
                485                 490                 495

Gly Ala Ser Leu Ser Tyr Thr Val Val Pro Ser Gly Arg Ser Gln
            500                 505                 510

Leu Lys Val Ser Ile Ala Gly Gly Ser Gly Asp Ala Asp Leu Tyr Val
                515                 520                 525

Arg Ser Gly Ser Ala Pro Thr Asp Thr Val Tyr Asn Cys Arg Pro Tyr
530                 535                 540

Leu Ser Gly Asn Glu Thr Cys Thr Ile Thr Ser Pro Ala Ala Gly
545                 550                 555                 560

Thr Trp His Val Arg Val Lys Gly Tyr Ser Thr Phe Ser Gly Val Thr
                565                 570                 575

Leu Thr Ala Gln Tyr
            580

<210> SEQ ID NO 5
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide from DNA isolate, Delta C
<220> FEATURE:
<221> NAME/KEY: SIGNAL
<222> LOCATION: (1)..(32)

<400> SEQUENCE: 5

Met Ser His Asp Ser Gln Pro Arg Leu Arg Gln Arg Ala Leu Val Val
1               5                   10                  15

Leu Gly Ala Ser Val Leu Ser Thr Leu Leu Ala Ala Pro Ala Phe
            20                  25                  30

Ala Gly Asp Val Gln Leu Ser Gly Leu Ser Ser Ala Pro Thr His Gln
        35                  40                  45

Arg Phe Ile Val Lys Tyr Lys Asp Gly Ala Asn Leu Val Ala Thr Pro
    50                  55                  60

Thr Ala Leu Ala Ser Ser Leu Lys Ala Ala Ser Ala Val Pro Ala
65                  70                  75                  80

Ala Gln Gly Arg Ala Leu Gly Leu Gln Lys Leu Arg Gln Leu Ala Ile
                85                  90                  95

Gly Pro Thr Val Val Lys Ala Asp Arg Pro Leu Asp Ala Ala Glu Ser
            100                 105                 110

Glu Leu Leu Met Arg Arg Leu Ala Ala Asp Pro Asn Val Glu Tyr Val
        115                 120                 125

Glu Val Asp Gln Leu Met His Ala Thr Leu Val Pro Asn Asp Ala Arg
    130                 135                 140
```

```
Leu Ser Glu Gln Trp Gly Phe Gly Thr Ser Asn Ala Ser Ile Asn Val
145                 150                 155                 160

Arg Pro Ala Trp Asp Lys Ala Thr Gly Thr Gly Val Val Val Ala Val
                165                 170                 175

Ile Asp Thr Gly Ile Thr Asn His Pro Asp Leu Asn Ala Asn Ile Leu
            180                 185                 190

Pro Gly Tyr Asp Phe Ile Ser Asp Ala Ala Met Ala Arg Asp Gly Gly
        195                 200                 205

Gly Arg Asp Asn Asn Ala Asn Asp Glu Gly Asp Trp Tyr Ala Ala Asn
    210                 215                 220

Glu Cys Gly Ser Gly Ile Pro Ala Ser Asn Ser Ser Trp His Gly Thr
225                 230                 235                 240

His Val Ala Gly Thr Ile Ala Ala Val Thr Asn Asn Ser Thr Gly Val
                245                 250                 255

Ala Gly Thr Ala Phe Asn Ala Lys Val Val Pro Val Arg Val Leu Gly
            260                 265                 270

Lys Cys Gly Gly Tyr Thr Ser Asp Ile Ala Asp Ala Ile Val Trp Ala
        275                 280                 285

Ser Gly Gly Thr Val Ser Gly Val Pro Ala Asn Ala Asn Pro Ala Glu
    290                 295                 300

Val Ile Asn Met Ser Leu Gly Gly Gly Thr Cys Ser Thr Thr Tyr
305                 310                 315                 320

Gln Asn Ala Ile Asn Gly Ala Val Ser Arg Gly Thr Thr Val Val Val
                325                 330                 335

Ala Ala Gly Asn Ser Asn Thr Asn Val Ser Ser Ser Val Pro Ala Asn
            340                 345                 350

Cys Ala Asn Val Ile Ala Val Ala Ala Thr Thr Ser Ala Gly Ala Arg
        355                 360                 365

Ala Ser Phe Ser Asn Tyr Gly Ala Gly Ile Asp Ile Ser Ala Pro Gly
    370                 375                 380

Gln Ala Ile Leu Ser Thr Leu Asn Ser Gly Thr Thr Val Pro Gly Thr
385                 390                 395                 400

Ala Ser Tyr Ala Ser Tyr Asn Gly Thr Ser Met Ala Ala Pro His Val
                405                 410                 415

Ala Gly Val Val Ala Leu Val Gln Ser Val Ala Pro Thr Ala Leu Thr
            420                 425                 430

Pro Ala Ala Ile Glu Thr Leu Leu Lys Asn Thr Ala Arg Ala Leu Pro
        435                 440                 445

Gly Ala Cys Ser Gly Gly Cys Gly Ala Gly Ile Val Asp Ala Asp Ala
    450                 455                 460

Ala Val Thr Ala Ala Leu
465                 470

<210> SEQ ID NO 6
<211> LENGTH: 1761
<212> TYPE: DNA
<213> ORGANISM: Unknown
<220> FEATURE:
<223> OTHER INFORMATION: Description of Unknown: DNA isolate,
      metagenomic DNA from soil sample
<220> FEATURE:
<221> NAME/KEY: sig_peptide
<222> LOCATION: (1)..(114)
<220> FEATURE:
<221> NAME/KEY: CDS
<222> LOCATION: (1)..(1758)

<400> SEQUENCE: 6
```

```
atg att acg aat tcg agc tcg gta ccc ggg gat ccg cag cgc ttg cgt        48
Met Ile Thr Asn Ser Ser Ser Val Pro Gly Asp Pro Gln Arg Leu Arg
1               5                   10                  15 cag cgt gcc ttg gtt gta ctc ggt ggt tcg gtg ctt tcg acc ctg ctc        96
Gln Arg Ala Leu Val Val Leu Gly Gly Ser Val Leu Ser Thr Leu Leu
            20                  25                  30 ctg gcg gcg ccg gca ttc gcc ggc gac gtg cag ttg agt ggc ctg gcc       144
Leu Ala Ala Pro Ala Phe Ala Gly Asp Val Gln Leu Ser Gly Leu Ala
        35                  40                  45 tcg gcc ccg acc cac cag cgt ttc atc gtc aag tac aag gac ggc gcc       192
Ser Ala Pro Thr His Gln Arg Phe Ile Val Lys Tyr Lys Asp Gly Ala
    50                  55                  60 acc gac gtg gcc acc ccg acc gca ctg gcc agt tcg ctc aag gcc gcc       240
Thr Asp Val Ala Thr Pro Thr Ala Leu Ala Ser Ser Leu Lys Ala Ala
65                  70                  75                  80 gcc caa gcc gtt ccc gcc gcg cag ggg cgc gcg ctg ggc ctg cag aag       288
Ala Gln Ala Val Pro Ala Ala Gln Gly Arg Ala Leu Gly Leu Gln Lys
                85                  90                  95 ctg cgc cag ctg gcc atc ggc ccg acc gtg gtc aag gcc gac cgc ccg       336
Leu Arg Gln Leu Ala Ile Gly Pro Thr Val Val Lys Ala Asp Arg Pro
            100                 105                 110 ctg gat gcc gcc gaa tcg gaa ctg ctg atg cgt cgc ctg gcc gcc gat       384
Leu Asp Ala Ala Glu Ser Glu Leu Leu Met Arg Arg Leu Ala Ala Asp
        115                 120                 125 ccg aac gtg gaa tac gtc gaa gtc gac cag ctg atg cac gcc acc ctg       432
Pro Asn Val Glu Tyr Val Glu Val Asp Gln Leu Met His Ala Thr Leu
    130                 135                 140 gtg ccc aac gac agc cgc ctg tcc gag cag tgg ggc ttc ggc acc agc       480
Val Pro Asn Asp Ser Arg Leu Ser Glu Gln Trp Gly Phe Gly Thr Ser
145                 150                 155                 160 aac gcc tcg atc aac gtg cgc ccg gcc tgg gac aag gcc acg ggg acc       528
Asn Ala Ser Ile Asn Val Arg Pro Ala Trp Asp Lys Ala Thr Gly Thr
                165                 170                 175 ggc gtg gtg gtg gcg gtg atc gat acc ggc atc acc aac cat ccg gat       576
Gly Val Val Val Ala Val Ile Asp Thr Gly Ile Thr Asn His Pro Asp
            180                 185                 190 ctg aac gcc aac atc ctg ccc ggc tat gac ttc atc agc gat gcc gcg       624
Leu Asn Ala Asn Ile Leu Pro Gly Tyr Asp Phe Ile Ser Asp Ala Ala
        195                 200                 205 atg gcg cgc gat ggc ggt ggc cgc gac aac aat gcc aac gac gaa ggc       672
Met Ala Arg Asp Gly Gly Gly Arg Asp Asn Asn Ala Asn Asp Glu Gly
    210                 215                 220 gac tgg tat gcc gcc aac gaa tgc ggc gcc ggc tac ccg gcc tcc aat       720
Asp Trp Tyr Ala Ala Asn Glu Cys Gly Ala Gly Tyr Pro Ala Ser Asn
225                 230                 235                 240 tcc agc tgg cac ggc acc cac gtg gcc ggc acc atc gcc gcg gtg acc       768
Ser Ser Trp His Gly Thr His Val Ala Gly Thr Ile Ala Ala Val Thr
                245                 250                 255 aac aac acc acc ggc gtg gcc ggc acc gcc tac aac gcc aag gtc gtt       816
Asn Asn Thr Thr Gly Val Ala Gly Thr Ala Tyr Asn Ala Lys Val Val
            260                 265                 270 ccg gtg cgc gtg ctg ggc aag tgc ggc ggc tat acc tcc gac atc gcc       864
Pro Val Arg Val Leu Gly Lys Cys Gly Gly Tyr Thr Ser Asp Ile Ala
        275                 280                 285 gat gcg atc gtg tgg gca tcc ggc ggc acc gtc agc ggc gtg ccg gcc       912
Asp Ala Ile Val Trp Ala Ser Gly Gly Thr Val Ser Gly Val Pro Ala
    290                 295                 300 aat gcc aac ccg gcc gaa gtg atc aac atg tcc ctc ggc ggc ggc ggc       960
Asn Ala Asn Pro Ala Glu Val Ile Asn Met Ser Leu Gly Gly Gly Gly
305                 310                 315                 320
```

| | | | | | | | | | | | | | | | | |
|---|---|---|---|---|---|---|---|---|---|---|---|---|---|---|---|---|
| agc | tgc | tcg | acc | acc | tac | cag | aac | gcc | atc | aac | ggc | gcg | gtg | tcg | cgc | 1008 |
| Ser | Cys | Ser | Thr | Thr | Tyr | Gln | Asn | Ala | Ile | Asn | Gly | Ala | Val | Ser | Arg | |
| | | | 325 | | | | | 330 | | | | | 335 | | | |
| ggc | acc | acc | gtg | gtg | gtg | gca | gcg | ggc | aac | agc | aac | acc | aac | gtg | tcc | 1056 |
| Gly | Thr | Thr | Val | Val | Val | Ala | Ala | Gly | Asn | Ser | Asn | Thr | Asn | Val | Ser | |
| | | 340 | | | | | 345 | | | | | 350 | | | | |
| tcg | tcg | gtg | ccg | gcc | aac | tgc | gcc | aac | gtg | atc | gcg | gtg | gcc | gcc | acc | 1104 |
| Ser | Ser | Val | Pro | Ala | Asn | Cys | Ala | Asn | Val | Ile | Ala | Val | Ala | Ala | Thr | |
| | 355 | | | | | 360 | | | | | 365 | | | | | |
| acc | tcg | gcc | ggc | gcc | cgc | gcc | agc | ttc | tcc | aac | tac | ggt | gcc | ggc | atc | 1152 |
| Thr | Ser | Ala | Gly | Ala | Arg | Ala | Ser | Phe | Ser | Asn | Tyr | Gly | Ala | Gly | Ile | |
| | 370 | | | | | 375 | | | | | 380 | | | | | |
| gat | gtc | tcg | gcg | ccg | ggc | cag | gcg | atc | ctg | tcc | acg | ctc | aac | agc | ggc | 1200 |
| Asp | Val | Ser | Ala | Pro | Gly | Gln | Ala | Ile | Leu | Ser | Thr | Leu | Asn | Ser | Gly | |
| 385 | | | | | 390 | | | | | 395 | | | | | 400 | |
| acc | acc | gtg | ccg | ggc | gct | gcg | tcc | tat | gcg | tcg | tac | aac | ggc | acc | tcg | 1248 |
| Thr | Thr | Val | Pro | Gly | Ala | Ala | Ser | Tyr | Ala | Ser | Tyr | Asn | Gly | Thr | Ser | |
| | | | | 405 | | | | | 410 | | | | | 415 | | |
| atg | gcg | gcc | ccg | cac | gtg | gcc | ggc | gtg | gtc | gcg | ctg | gtg | cag | tcg | gtc | 1296 |
| Met | Ala | Ala | Pro | His | Val | Ala | Gly | Val | Val | Ala | Leu | Val | Gln | Ser | Val | |
| | | | 420 | | | | | 425 | | | | | 430 | | | |
| gcg | ccc | acc | gcg | ctg | tcg | ccg | gca | gcc | atc | gag | acg | ctg | ctc | aag | aac | 1344 |
| Ala | Pro | Thr | Ala | Leu | Ser | Pro | Ala | Ala | Ile | Glu | Thr | Leu | Leu | Lys | Asn | |
| | | 435 | | | | | 440 | | | | | 445 | | | | |
| acc | gca | cgg | gcc | ctg | ccg | ggc | gcc | tgc | agc | ggc | ggc | tgc | ggc | gcg | ggc | 1392 |
| Thr | Ala | Arg | Ala | Leu | Pro | Gly | Ala | Cys | Ser | Gly | Gly | Cys | Gly | Ala | Gly | |
| | 450 | | | | | 455 | | | | | 460 | | | | | |
| atc | gtc | gat | gcg | gat | gcg | gcc | gtc | acc | gcc | gcg | ctg | ggc | ggg | acc | aac | 1440 |
| Ile | Val | Asp | Ala | Asp | Ala | Ala | Val | Thr | Ala | Ala | Leu | Gly | Gly | Thr | Asn | |
| 465 | | | | | 470 | | | | | 475 | | | | | 480 | |
| ccg | aac | ccg | ggc | acc | ggc | acg | ctg | cag | aac | aac | gtg | ccg | gtc | agc | ggc | 1488 |
| Pro | Asn | Pro | Gly | Thr | Gly | Thr | Leu | Gln | Asn | Asn | Val | Pro | Val | Ser | Gly | |
| | | | | 485 | | | | | 490 | | | | | 495 | | |
| ctg | ggt | gct | tcc | agc | ggt | gca | tcg | ctg | gcc | tac | acc | gtg | gcc | gtg | ccc | 1536 |
| Leu | Gly | Ala | Ser | Ser | Gly | Ala | Ser | Leu | Ala | Tyr | Thr | Val | Ala | Val | Pro | |
| | | | 500 | | | | | 505 | | | | | 510 | | | |
| tcg | ggt | cgc | tcg | cag | ctg | aag | gtg | acc | atc | gcc | ggc | ggc | acg | ggc | gat | 1584 |
| Ser | Gly | Arg | Ser | Gln | Leu | Lys | Val | Thr | Ile | Ala | Gly | Gly | Thr | Gly | Asp | |
| | | 515 | | | | | 520 | | | | | 525 | | | | |
| gcg | gac | ctg | tac | gtg | cgc | tcg | ggc | agc | gcg | ccc | acc | gac | acc | gtg | tac | 1632 |
| Ala | Asp | Leu | Tyr | Val | Arg | Ser | Gly | Ser | Ala | Pro | Thr | Asp | Thr | Val | Tyr | |
| | 530 | | | | | 535 | | | | | 540 | | | | | |
| acc | tgc | cgc | ccg | tac | ctg | agc | ggc | aac | aac | gaa | acc | tgc | acg | atc | acc | 1680 |
| Thr | Cys | Arg | Pro | Tyr | Leu | Ser | Gly | Asn | Asn | Glu | Thr | Cys | Thr | Ile | Thr | |
| 545 | | | | | 550 | | | | | 555 | | | | | 560 | |
| gcc | ccg | gcc | gcg | ggg | acc | tgg | cat | gtc | cgg | gtg | aag | gcc | tac | agc | acc | 1728 |
| Ala | Pro | Ala | Ala | Gly | Thr | Trp | His | Val | Arg | Val | Lys | Ala | Tyr | Ser | Thr | |
| | | | | 565 | | | | | 570 | | | | | 575 | | |
| ttc | tcc | ggc | gtg | acc | ctg | acc | gcg | cag | tat | tga | | | | | | 1761 |
| Phe | Ser | Gly | Val | Thr | Leu | Thr | Ala | Gln | Tyr | | | | | | | |
| | | | 580 | | | | | 585 | | | | | | | | |

<210> SEQ ID NO 7
<211> LENGTH: 586
<212> TYPE: PRT
<213> ORGANISM: Unknown
<220> FEATURE:
<223> OTHER INFORMATION: Description of Unknown: Polypeptide from
    DNA isolate, metagenomic DNA from soil sample

<400> SEQUENCE: 7

-continued

```
Met Ile Thr Asn Ser Ser Val Pro Gly Asp Pro Gln Arg Leu Arg
1               5                   10                  15

Gln Arg Ala Leu Val Val Leu Gly Gly Ser Val Leu Ser Thr Leu Leu
            20                  25                  30

Leu Ala Ala Pro Ala Phe Ala Gly Asp Val Gln Leu Ser Gly Leu Ala
            35                  40                  45

Ser Ala Pro Thr His Gln Arg Phe Ile Val Lys Tyr Lys Asp Gly Ala
50                  55                  60

Thr Asp Val Ala Thr Pro Thr Ala Leu Ala Ser Ser Leu Lys Ala Ala
65                  70                  75                  80

Ala Gln Ala Val Pro Ala Ala Gly Arg Ala Leu Gly Leu Gln Lys
                85                  90                  95

Leu Arg Gln Leu Ala Ile Gly Pro Thr Val Val Lys Ala Asp Arg Pro
            100                 105                 110

Leu Asp Ala Ala Glu Ser Glu Leu Leu Met Arg Arg Leu Ala Ala Asp
            115                 120                 125

Pro Asn Val Glu Tyr Val Glu Val Asp Gln Leu Met His Ala Thr Leu
            130                 135                 140

Val Pro Asn Asp Ser Arg Leu Ser Glu Gln Trp Gly Phe Gly Thr Ser
145                 150                 155                 160

Asn Ala Ser Ile Asn Val Arg Pro Ala Trp Asp Lys Ala Thr Gly Thr
                165                 170                 175

Gly Val Val Val Ala Val Ile Asp Thr Gly Ile Thr Asn His Pro Asp
            180                 185                 190

Leu Asn Ala Asn Ile Leu Pro Gly Tyr Asp Phe Ile Ser Asp Ala Ala
            195                 200                 205

Met Ala Arg Asp Gly Gly Gly Arg Asp Asn Asn Ala Asn Asp Glu Gly
210                 215                 220

Asp Trp Tyr Ala Ala Asn Glu Cys Gly Ala Gly Tyr Pro Ala Ser Asn
225                 230                 235                 240

Ser Ser Trp His Gly Thr His Val Ala Gly Thr Ile Ala Ala Val Thr
                245                 250                 255

Asn Asn Thr Thr Gly Val Ala Gly Thr Ala Tyr Asn Ala Lys Val Val
            260                 265                 270

Pro Val Arg Val Leu Gly Lys Cys Gly Gly Tyr Thr Ser Asp Ile Ala
            275                 280                 285

Asp Ala Ile Val Trp Ala Ser Gly Gly Thr Val Ser Gly Val Pro Ala
            290                 295                 300

Asn Ala Asn Pro Ala Glu Val Ile Asn Met Ser Leu Gly Gly Gly Gly
305                 310                 315                 320

Ser Cys Ser Thr Thr Tyr Gln Asn Ala Ile Asn Gly Ala Val Ser Arg
                325                 330                 335

Gly Thr Thr Val Val Ala Ala Gly Asn Ser Asn Thr Asn Val Ser
            340                 345                 350

Ser Ser Val Pro Ala Asn Cys Ala Asn Val Ile Ala Val Ala Ala Thr
            355                 360                 365

Thr Ser Ala Gly Ala Arg Ala Ser Phe Ser Asn Tyr Gly Ala Gly Ile
370                 375                 380

Asp Val Ser Ala Pro Gly Gln Ala Ile Leu Ser Thr Leu Asn Ser Gly
385                 390                 395                 400

Thr Thr Val Pro Gly Ala Ala Ser Tyr Ala Ser Tyr Asn Gly Thr Ser
                405                 410                 415

Met Ala Ala Pro His Val Ala Gly Val Val Ala Leu Val Gln Ser Val
            420                 425                 430
```

```
Ala Pro Thr Ala Leu Ser Pro Ala Ile Glu Thr Leu Leu Lys Asn
        435                 440                 445

Thr Ala Arg Ala Leu Pro Gly Ala Cys Ser Gly Gly Cys Gly Ala Gly
    450                 455                 460

Ile Val Asp Ala Asp Ala Val Thr Ala Leu Gly Gly Thr Asn
465                 470                 475                 480

Pro Asn Pro Gly Thr Gly Thr Leu Gln Asn Asn Val Pro Val Ser Gly
                485                 490                 495

Leu Gly Ala Ser Ser Gly Ala Ser Leu Ala Tyr Thr Val Ala Val Pro
            500                 505                 510

Ser Gly Arg Ser Gln Leu Lys Val Thr Ile Ala Gly Thr Gly Asp
    515                 520                 525

Ala Asp Leu Tyr Val Arg Ser Gly Ser Ala Pro Thr Asp Thr Val Tyr
        530                 535                 540

Thr Cys Arg Pro Tyr Leu Ser Gly Asn Asn Glu Thr Cys Thr Ile Thr
545                 550                 555                 560

Ala Pro Ala Ala Gly Thr Trp His Val Arg Val Lys Ala Tyr Ser Thr
                565                 570                 575

Phe Ser Gly Val Thr Leu Thr Ala Gln Tyr
            580                 585

<210> SEQ ID NO 8
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide from DNA isolate, Delta C
<220> FEATURE:
<221> NAME/KEY: SIGNAL
<222> LOCATION: (1)..(32)
<223> OTHER INFORMATION: Signal peptide from HP70

<400> SEQUENCE: 8

Met Ser His Asp Ser Gln Pro Arg Leu Arg Gln Arg Ala Leu Val Val
1               5                   10                  15

Leu Gly Ala Ser Val Leu Ser Thr Leu Leu Ala Ala Pro Ala Phe
            20                  25                  30

Ala Gly Asp Val Gln Leu Ser Gly Leu Ala Ser Ala Pro Thr His Gln
        35                  40                  45

Arg Phe Ile Val Lys Tyr Lys Asp Gly Ala Thr Asp Val Ala Thr Pro
    50                  55                  60

Thr Ala Leu Ala Ser Ser Leu Lys Ala Ala Ala Gln Ala Val Pro Ala
65              70                  75                  80

Ala Gln Gly Arg Ala Leu Gly Leu Gln Lys Leu Arg Gln Leu Ala Ile
            85                  90                  95

Gly Pro Thr Val Val Lys Ala Asp Arg Pro Leu Asp Ala Ala Glu Ser
        100                 105                 110

Glu Leu Leu Met Arg Arg Leu Ala Ala Asp Pro Asn Val Glu Tyr Val
    115                 120                 125

Glu Val Asp Gln Leu Met His Ala Thr Leu Val Pro Asn Asp Ser Arg
    130                 135                 140

Leu Ser Glu Gln Trp Gly Phe Gly Thr Ser Asn Ala Ser Ile Asn Val
145                 150                 155                 160

Arg Pro Ala Trp Asp Lys Ala Thr Gly Thr Gly Val Val Val Ala Val
                165                 170                 175

Ile Asp Thr Gly Ile Thr Asn His Pro Asp Leu Asn Ala Asn Ile Leu
```

```
                       180                 185                 190
Pro Gly Tyr Asp Phe Ile Ser Asp Ala Ala Met Ala Arg Asp Gly Gly
            195                 200                 205
Gly Arg Asp Asn Asn Ala Asn Asp Glu Gly Asp Trp Tyr Ala Ala Asn
210                 215                 220
Glu Cys Gly Ala Gly Tyr Pro Ala Ser Asn Ser Ser Trp His Gly Thr
225                 230                 235                 240
His Val Ala Gly Thr Ile Ala Ala Val Thr Asn Asn Thr Thr Gly Val
            245                 250                 255
Ala Gly Thr Ala Tyr Asn Ala Lys Val Val Pro Val Arg Val Leu Gly
            260                 265                 270
Lys Cys Gly Gly Tyr Thr Ser Asp Ile Ala Asp Ala Ile Val Trp Ala
            275                 280                 285
Ser Gly Gly Thr Val Ser Gly Val Pro Ala Asn Ala Asn Pro Ala Glu
            290                 295                 300
Val Ile Asn Met Ser Leu Gly Gly Gly Ser Cys Ser Thr Thr Tyr
305                 310                 315                 320
Gln Asn Ala Ile Asn Gly Ala Val Ser Arg Gly Thr Thr Val Val Val
            325                 330                 335
Ala Ala Gly Asn Ser Asn Thr Asn Val Ser Ser Val Pro Ala Asn
            340                 345                 350
Cys Ala Asn Val Ile Ala Val Ala Ala Thr Thr Ser Ala Gly Ala Arg
355                 360                 365
Ala Ser Phe Ser Asn Tyr Gly Ala Gly Ile Asp Val Ser Ala Pro Gly
            370                 375                 380
Gln Ala Ile Leu Ser Thr Leu Asn Ser Gly Thr Thr Val Pro Gly Ala
385                 390                 395                 400
Ala Ser Tyr Ala Ser Tyr Asn Gly Thr Ser Met Ala Ala Pro His Val
            405                 410                 415
Ala Gly Val Val Ala Leu Val Gln Ser Val Ala Pro Thr Ala Leu Ser
            420                 425                 430
Pro Ala Ala Ile Glu Thr Leu Leu Lys Asn Thr Ala Arg Ala Leu Pro
            435                 440                 445
Gly Ala Cys Ser Gly Gly Cys Gly Ala Gly Ile Val Asp Ala Asp Ala
            450                 455                 460
Ala Val Thr Ala Ala Leu
465                 470

<210> SEQ ID NO 9
<211> LENGTH: 587
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Ile or absent
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: His or Asn
<220> FEATURE:
<221> NAME/KEY: MOD_RES
<222> LOCATION: (5)..(5)
<223> OTHER INFORMATION: Asp or Ser
```

```
<220> FEATURE:
<221> NAME/KEY: MOD_RES
<222> LOCATION: (7)..(7)
<223> OTHER INFORMATION: Ser or absent
<220> FEATURE:
<221> NAME/KEY: MOD_RES
<222> LOCATION: (8)..(8)
<223> OTHER INFORMATION: Val or absent
<220> FEATURE:
<221> NAME/KEY: MOD_RES
<222> LOCATION: (9)..(9)
<223> OTHER INFORMATION: Pro or absent
<220> FEATURE:
<221> NAME/KEY: MOD_RES
<222> LOCATION: (10)..(10)
<223> OTHER INFORMATION: Gly or absent
<220> FEATURE:
<221> NAME/KEY: MOD_RES
<222> LOCATION: (11)..(11)
<223> OTHER INFORMATION: Asp or absent
<220> FEATURE:
<221> NAME/KEY: MOD_RES
<222> LOCATION: (12)..(12)
<223> OTHER INFORMATION: Gln or Pro
<220> FEATURE:
<221> NAME/KEY: MOD_RES
<222> LOCATION: (13)..(13)
<223> OTHER INFORMATION: Pro or Gln
<220> FEATURE:
<221> NAME/KEY: MOD_RES
<222> LOCATION: (25)..(25)
<223> OTHER INFORMATION: Gly or Ala
<220> FEATURE:
<221> NAME/KEY: MOD_RES
<222> LOCATION: (48)..(48)
<223> OTHER INFORMATION: Ser or Ala
<220> FEATURE:
<221> NAME/KEY: MOD_RES
<222> LOCATION: (65)..(65)
<223> OTHER INFORMATION: Asn or Thr
<220> FEATURE:
<221> NAME/KEY: MOD_RES
<222> LOCATION: (66)..(66)
<223> OTHER INFORMATION: Leu or Asp
<220> FEATURE:
<221> NAME/KEY: MOD_RES
<222> LOCATION: (82)..(82)
<223> OTHER INFORMATION: Ser or Gln
<220> FEATURE:
<221> NAME/KEY: MOD_RES
<222> LOCATION: (149)..(149)
<223> OTHER INFORMATION: Ala or Ser
<220> FEATURE:
<221> NAME/KEY: MOD_RES
<222> LOCATION: (234)..(234)
<223> OTHER INFORMATION: Ser or Ala
<220> FEATURE:
<221> NAME/KEY: MOD_RES
<222> LOCATION: (236)..(236)
<223> OTHER INFORMATION: Ile or Tyr
<220> FEATURE:
<221> NAME/KEY: MOD_RES
<222> LOCATION: (259)..(259)
<223> OTHER INFORMATION: Ser or Thr
<220> FEATURE:
<221> NAME/KEY: MOD_RES
<222> LOCATION: (267)..(267)
<223> OTHER INFORMATION: Phe or Tyr
<220> FEATURE:
<221> NAME/KEY: MOD_RES
<222> LOCATION: (321)..(321)
<223> OTHER INFORMATION: Thr or Ser
<220> FEATURE:
<221> NAME/KEY: MOD_RES
<222> LOCATION: (386)..(386)
<223> OTHER INFORMATION: Ile or Val
<220> FEATURE:
<221> NAME/KEY: MOD_RES
<222> LOCATION: (406)..(406)
<223> OTHER INFORMATION: Thr or Ala
```

```
<220> FEATURE:
<221> NAME/KEY: MOD_RES
<222> LOCATION: (438)..(438)
<223> OTHER INFORMATION: Thr or Ser
<220> FEATURE:
<221> NAME/KEY: MOD_RES
<222> LOCATION: (487)..(487)
<223> OTHER INFORMATION: Thr or absent
<220> FEATURE:
<221> NAME/KEY: MOD_RES
<222> LOCATION: (488)..(488)
<223> OTHER INFORMATION: Val or Thr
<220> FEATURE:
<221> NAME/KEY: MOD_RES
<222> LOCATION: (501)..(501)
<223> OTHER INFORMATION: Ala or Ser
<220> FEATURE:
<221> NAME/KEY: MOD_RES
<222> LOCATION: (507)..(507)
<223> OTHER INFORMATION: Ser or Ala
<220> FEATURE:
<221> NAME/KEY: MOD_RES
<222> LOCATION: (511)..(511)
<223> OTHER INFORMATION: Val or Ala
<220> FEATURE:
<221> NAME/KEY: MOD_RES
<222> LOCATION: (522)..(522)
<223> OTHER INFORMATION: Ser or Thr
<220> FEATURE:
<221> NAME/KEY: MOD_RES
<222> LOCATION: (527)..(527)
<223> OTHER INFORMATION: Ser or Thr
<220> FEATURE:
<221> NAME/KEY: MOD_RES
<222> LOCATION: (546)..(546)
<223> OTHER INFORMATION: Asn or Thr
<220> FEATURE:
<221> NAME/KEY: MOD_RES
<222> LOCATION: (562)..(562)
<223> OTHER INFORMATION: Ser or Ala
<220> FEATURE:
<221> NAME/KEY: MOD_RES
<222> LOCATION: (574)..(574)
<223> OTHER INFORMATION: Gly or Ala

<400> SEQUENCE: 9

Met Xaa Xaa Xaa Ser Xaa Xaa Xaa Xaa Xaa Xaa Arg Leu Arg
1               5                   10                  15

Gln Arg Ala Leu Val Val Leu Gly Xaa Ser Val Leu Ser Thr Leu Leu
            20                  25                  30

Leu Ala Ala Pro Ala Phe Ala Gly Asp Val Gln Leu Ser Gly Leu Xaa
        35                  40                  45

Ser Ala Pro Thr His Gln Arg Phe Ile Val Lys Tyr Lys Asp Gly Ala
    50                  55                  60

Xaa Xaa Val Ala Thr Pro Thr Ala Leu Ala Ser Ser Leu Lys Ala Ala
65                  70                  75                  80

Ala Xaa Ala Val Pro Ala Ala Gln Gly Arg Ala Leu Gly Leu Gln Lys
                85                  90                  95

Leu Arg Gln Leu Ala Ile Gly Pro Thr Val Val Lys Ala Asp Arg Pro
            100                 105                 110

Leu Asp Ala Ala Glu Ser Glu Leu Leu Met Arg Arg Leu Ala Ala Asp
        115                 120                 125

Pro Asn Val Glu Tyr Val Glu Val Asp Gln Leu Met His Ala Thr Leu
    130                 135                 140

Val Pro Asn Asp Xaa Arg Leu Ser Glu Gln Trp Gly Phe Gly Thr Ser
145                 150                 155                 160

Asn Ala Ser Ile Asn Val Arg Pro Ala Trp Asp Lys Ala Thr Gly Thr
                165                 170                 175
```

```
Gly Val Val Ala Val Ile Asp Thr Gly Ile Thr Asn His Pro Asp
            180                 185                 190

Leu Asn Ala Asn Ile Leu Pro Gly Tyr Asp Phe Ile Ser Asp Ala Ala
            195                 200                 205

Met Ala Arg Asp Gly Gly Arg Asp Asn Asn Ala Asn Asp Glu Gly
210             215                 220

Asp Trp Tyr Ala Ala Asn Glu Cys Gly Xaa Gly Xaa Pro Ala Ser Asn
225             230                 235                 240

Ser Ser Trp His Gly Thr His Val Ala Gly Thr Ile Ala Ala Val Thr
                245                 250                 255

Asn Asn Xaa Thr Gly Val Ala Gly Thr Ala Xaa Asn Ala Lys Val Val
            260                 265                 270

Pro Val Arg Val Leu Gly Lys Cys Gly Gly Tyr Thr Ser Asp Ile Ala
            275                 280                 285

Asp Ala Ile Val Trp Ala Ser Gly Thr Val Ser Gly Val Pro Ala
290                 295                 300

Asn Ala Asn Pro Ala Glu Val Ile Asn Met Ser Leu Gly Gly Gly Gly
305                 310                 315                 320

Xaa Cys Ser Thr Thr Tyr Gln Asn Ala Ile Asn Gly Ala Val Ser Arg
                325                 330                 335

Gly Thr Thr Val Val Ala Ala Gly Asn Ser Asn Thr Asn Val Ser
            340                 345                 350

Ser Ser Val Pro Ala Asn Cys Ala Asn Val Ile Ala Val Ala Ala Thr
            355                 360                 365

Thr Ser Ala Gly Ala Arg Ala Ser Phe Ser Asn Tyr Gly Ala Gly Ile
370                 375                 380

Asp Xaa Ser Ala Pro Gly Gln Ala Ile Leu Ser Thr Leu Asn Ser Gly
385                 390                 395                 400

Thr Thr Val Pro Gly Xaa Ala Ser Tyr Ala Ser Tyr Asn Gly Thr Ser
                405                 410                 415

Met Ala Ala Pro His Val Ala Gly Val Val Ala Leu Val Gln Ser Val
                420                 425                 430

Ala Pro Thr Ala Leu Xaa Pro Ala Ala Ile Glu Thr Leu Leu Lys Asn
            435                 440                 445

Thr Ala Arg Ala Leu Pro Gly Ala Cys Ser Gly Gly Cys Gly Ala Gly
450                 455                 460

Ile Val Asp Ala Asp Ala Ala Val Thr Ala Ala Leu Gly Gly Thr Asn
465                 470                 475                 480

Pro Asn Pro Gly Thr Gly Xaa Xaa Leu Gln Asn Asn Val Pro Val Ser
                485                 490                 495

Gly Leu Gly Ala Xaa Ser Gly Ala Ser Leu Xaa Tyr Thr Val Xaa Val
            500                 505                 510

Pro Ser Gly Arg Ser Gln Leu Lys Val Xaa Ile Ala Gly Gly Xaa Gly
            515                 520                 525

Asp Ala Asp Leu Tyr Val Arg Ser Gly Ser Ala Pro Thr Asp Thr Val
            530                 535                 540

Tyr Xaa Cys Arg Pro Tyr Leu Ser Gly Asn Asn Glu Thr Cys Thr Ile
545                 550                 555                 560

Thr Xaa Pro Ala Ala Gly Thr Trp His Val Arg Val Lys Xaa Tyr Ser
            565                 570                 575

Thr Phe Ser Gly Val Thr Leu Thr Ala Gln Tyr
                580                 585

<210> SEQ ID NO 10
```

<211> LENGTH: 27
<212> TYPE: DNA
<213> ORGANISM: Artificial Sequence
<220> FEATURE:
<223> OTHER INFORMATION: Description of Artificial Sequence: Synthetic
primer HP70f

<400> SEQUENCE: 10
gaattcgatg tctcatgatt cgcaacc 27

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
primer HP70r

<400> SEQUENCE: 11
ggatcctcac agcgccgccg tgaccgccg 29

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
primer HP53f

<400> SEQUENCE: 12
gctgagcggc ctggcctcgg ccccg 25

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
primer HP53r

<400> SEQUENCE: 13
ggatcctcac agcgccgccg tgacggccg 29

<210> SEQ ID NO 14
<211> LENGTH: 580
<212> TYPE: PRT
<213> ORGANISM: Xanthomonas campestris
<220> FEATURE:
<223> OTHER INFORMATION: Xanthomonas campestris pv. campestris (ATCC
33913)

<400> SEQUENCE: 14

```
Met Ser Thr Ala Ser Leu Arg Lys Arg Thr Gly Ser Leu Thr Ile Leu
1               5                   10                  15

Gly Ala Ser Ala Leu Thr Ser Leu Leu Leu Ala Met Pro Ala Phe Ala
            20                  25                  30

Gly Glu Val Tyr Leu Asp Gly Leu Ala Thr Ala Gln Thr His Gln Lys
        35                  40                  45

Phe Ile Val Thr Tyr Lys Asp Gly Ser Thr Ala Leu Ala Ser Pro Ser
    50                  55                  60

Ala Leu Thr Thr Ser Leu Arg Thr Ala Ala Arg Ala Val Pro Ala Lys
65                  70                  75                  80

Ala Gly Lys Ala Leu Gly Leu Asn Ser Val Arg Arg Leu Ala Leu Gly
                85                  90                  95

Pro Glu Leu Val Arg Ala Asp Arg Ala Leu Asp Arg Ala Glu Ala Glu
```

-continued

```
                100                 105                 110
Thr Leu Met Arg Gln Leu Ala Ala Asp Pro Asn Val Gln Ser Val Glu
            115                 120                 125
Val Asp Gln Ile Leu His Ala Thr Leu Thr Pro Asn Asp Thr Arg Leu
130                 135                 140
Ser Glu Gln Trp Ala Phe Gly Thr Thr Asn Ala Gly Leu Asn Ile Arg
145                 150                 155                 160
Pro Ala Trp Asp Lys Ala Thr Gly Ser Gly Thr Val Val Ala Val Ile
                165                 170                 175
Asp Thr Gly Ile Thr Ser His Ala Asp Leu Asn Ala Asn Ile Leu Ala
                180                 185                 190
Gly Tyr Asp Phe Ile Ser Asp Ala Thr Ala Arg Asp Gly Asn Gly
                195                 200                 205
Arg Asp Ser Asn Ala Ala Asp Glu Gly Asp Trp Tyr Ala Ala Asn Glu
210                 215                 220
Cys Gly Ala Gly Ile Pro Ala Ala Ser Ser Trp His Gly Thr His
225                 230                 235                 240
Val Ala Gly Thr Val Ala Ala Val Thr Asn Asn Thr Thr Gly Val Ala
                245                 250                 255
Gly Thr Ala Tyr Gly Ala Lys Val Val Pro Val Arg Val Leu Gly Lys
                260                 265                 270
Cys Gly Gly Ser Leu Ser Asp Ile Ala Asp Ala Ile Val Trp Ala Ser
            275                 280                 285
Gly Gly Thr Val Ser Gly Ile Pro Ala Asn Ala Asn Pro Ala Glu Val
            290                 295                 300
Ile Asn Met Ser Leu Gly Gly Gly Ser Cys Ser Thr Thr Met Gln
305                 310                 315                 320
Asn Ala Ile Asn Gly Ala Val Ser Arg Gly Thr Thr Val Val Val Ala
                325                 330                 335
Ala Gly Asn Asp Ala Ser Asn Val Ser Gly Ser Leu Pro Ala Asn Cys
                340                 345                 350
Ala Asn Val Ile Ala Val Ala Thr Thr Ser Ala Gly Ala Lys Ala
            355                 360                 365
Ser Tyr Ser Asn Phe Gly Thr Gly Ile Asp Val Ser Ala Pro Gly Ser
370                 375                 380
Ser Ile Leu Ser Thr Leu Asn Ser Gly Thr Thr Pro Gly Ser Ala
385                 390                 395                 400
Ser Tyr Ala Ser Tyr Asn Gly Thr Ser Met Ala Ser Pro His Val Ala
                405                 410                 415
Gly Val Val Ala Leu Val Gln Ser Val Ala Pro Thr Ala Leu Thr Pro
                420                 425                 430
Ala Ala Val Glu Thr Leu Leu Lys Asn Thr Ala Arg Ala Leu Pro Gly
            435                 440                 445
Ala Cys Ser Gly Gly Cys Gly Ala Gly Ile Val Asn Ala Asp Ala Ala
            450                 455                 460
Val Thr Ala Ala Ile Asn Gly Ser Gly Gly Gly Gly Gly Gly
465                 470                 475                 480
Asn Thr Leu Thr Asn Gly Thr Pro Val Thr Gly Leu Gly Ala Ala Thr
                485                 490                 495
Gly Ala Glu Leu Asn Tyr Thr Ile Thr Val Pro Ala Gly Ser Gly Thr
            500                 505                 510
Leu Thr Val Thr Thr Ser Gly Gly Ser Gly Asp Ala Asp Leu Tyr Val
            515                 520                 525
```

```
Arg Ala Gly Ser Ala Pro Thr Asp Ser Ala Tyr Thr Cys Arg Pro Tyr
            530                 535                 540

Arg Ser Gly Asn Ala Glu Thr Cys Thr Ile Thr Ala Pro Ser Gly Thr
545                 550                 555                 560

Tyr Tyr Val Arg Leu Lys Ala Tyr Ser Thr Phe Ser Gly Val Thr Leu
                565                 570                 575

Arg Ala Ser Tyr
            580

<210> SEQ ID NO 15
<211> LENGTH: 384
<212> TYPE: PRT
<213> ORGANISM: Bacillus lentus
<220> FEATURE:
<223> OTHER INFORMATION: Bacillus lentus DSM 5483

<400> SEQUENCE: 15

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Arg Ala
                20                  25                  30

Glu Glu Ala Lys Glu Lys Tyr Leu Ile Gly Phe Asn Glu Gln Glu Ala
            35                  40                  45

Val Ser Glu Phe Val Glu Gln Val Glu Ala Asn Asp Glu Val Ala Ile
        50                  55                  60

Leu Ser Glu Glu Glu Glu Val Glu Ile Glu Leu Leu His Glu Phe Glu
65                  70                  75                  80

Thr Ile Pro Val Leu Ser Val Glu Leu Ser Pro Glu Asp Val Asp Ala
                85                  90                  95

Leu Glu Leu Asp Pro Ala Ile Ser Tyr Ile Glu Glu Asp Ala Glu Val
            100                 105                 110

Thr Thr Met Ala Gln Ser Val Pro Trp Gly Ile Ser Arg Val Gln Ala
        115                 120                 125

Pro Ala Ala His Asn Arg Gly Leu Thr Gly Ser Gly Val Lys Val Ala
130                 135                 140

Val Leu Asp Thr Gly Ile Ser Thr His Pro Asp Leu Asn Ile Arg Gly
145                 150                 155                 160

Gly Ala Ser Phe Val Pro Gly Glu Pro Ser Thr Gln Asp Gly Asn Gly
                165                 170                 175

His Gly Thr His Val Ala Gly Thr Ile Ala Ala Leu Asn Asn Ser Ile
            180                 185                 190

Gly Val Leu Gly Val Ala Pro Ser Ala Glu Leu Tyr Ala Val Lys Val
        195                 200                 205

Leu Gly Ala Asp Gly Arg Gly Ala Ile Ser Ser Ile Ala Gln Gly Leu
210                 215                 220

Gly Trp Ala Gly Asn Asn Gly Met His Val Ala Asn Leu Ser Leu Gly
225                 230                 235                 240

Ser Pro Ser Pro Ser Ala Thr Leu Glu Gln Ala Val Asn Ser Ala Thr
                245                 250                 255

Ser Arg Gly Val Leu Val Val Ala Ala Ser Gly Asn Ser Gly Ala Ser
            260                 265                 270

Ser Ile Ser Tyr Pro Ala Arg Tyr Ala Asn Ala Met Ala Val Gly Ala
        275                 280                 285

Thr Asp Gln Asn Asn Asn Arg Ala Ser Phe Ser Gln Tyr Gly Ala Gly
290                 295                 300

Leu Asp Ile Val Ala Pro Gly Val Asn Val Gln Ser Thr Tyr Pro Gly
```

|     |     |     |     | 305 |     |     |     |     | 310 |     |     |     |     | 315 |     |     |     |     | 320 |
|---|---|---|---|---|---|---|---|---|---|---|---|---|---|---|---|---|---|---|---|

Ser Thr Tyr Ala Ser Leu Asn Gly Thr Ser Met Ala Thr Pro His Val
              325                 330                 335

Ala Gly Ala Ala Ala Leu Val Lys Gln Lys Asn Pro Ser Trp Ser Asn
              340                 345                 350

Val Gln Ile Arg Asn His Leu Lys Asn Thr Ala Thr Ser Leu Gly Ser
              355                 360                 365

Thr Asn Leu Tyr Gly Ser Gly Leu Val Asn Ala Glu Ala Ala Thr Arg
          370                 375                 380

<210> SEQ ID NO 16
<211> LENGTH: 1741
<212> TYPE: DNA
<213> ORGANISM: Xanthomonas campestris
<220> FEATURE:
<223> OTHER INFORMATION: Xanthomonas campestris pv. campestris (ATCC 33913)

<400> SEQUENCE: 16

```
atgtcgactg cgtctctccg caagcgtact ggctcgctca ccatcctggg cgcgtccgcc      60
ctgacctcgc tgctgctcgc gatgccggcc tttgccggcg aggtctacct ggatggcctg     120
gccaccgcac agacccatca gaaattcatc gtgacctaca aggacggcag caccgcgctg     180
gccagcccgt ccgcgttgac cacctcgctg cgcactgctg cgcgcgcggt gccggccaaa     240
gccggcaagg cgctgggcct gaactcggtg cgccgcctgg cgttggggcc ggaactggta     300
agggcagacc gcgccctgga ccgcgccgag gccgaaacct gatgcggcaa ttggccgctg     360
atcccaacgt gcagagcgtt gaagtcgacc agatcctgca tgccacgctc accccaacg     420
acacccggtt gtccgagcag tgggcgttcg gcaccaccaa cgccggcctg aacatccgcc     480
cggcctggga caaggccacc ggcagcggca cggtcgtggc ggtgattgat accggcatca     540
ccagtcatgc cgacctcaac gccaacatcc tcgcgggcta cgacttcatc agcgatgcga     600
ccaccgcacg cgatggcaac ggccgtgaca gcaacgccgc cgacgaaggc gactggtacg     660
ccgcaacga atgcggcgcc ggcattcccg ccgcagctcc agctggcacg cacccatgt      720
ggccggcacg gtcgcggcag tgaccaacaa caccaccggc gtagccggca ccgcctacgg     780
cgccaaggtc gtaccggtgc gcgtgctcgg caagtgcggt gggtcgctgt cggatatcgc     840
cgacgccatc gtctgggcct ccggcggcac cgtcagcggc atcccggcca atgctaaccc     900
ggccgaggtg atcaacatgt cgctcggcgg cggcggtagc tgctcgacca ccatgcagaa     960
cgccatcaac ggtgcggtgt cgcgcggcac cacggtggtg gtcgcggccg gcaacgatgc    1020
gtccaatgtg tccggttcgc tgccggccaa ctgcgcgaac gtgattgcgg tggccgccac    1080
cacctcggcg ggcgcgaagg ccagctattc caacttcggc accggtatcg atgtgtcggc    1140
gcccggctcg tcgatcctgt ccacgctcaa cagcggcacc accacgccgg tagcgccag     1200
ctatgcctcc tacaacggca cctcgatggc gtcgccgcat gtggccggcg tggtcgcgct    1260
ggtgcagtcg gtcgcccccga ccgcgctgac gccagcagcg gtggaaacct tgttgaagaa    1320
caccgcgcgt gctttaccgg cgcctgctc gggcggctgc ggtgccggca tcgtcaacgc    1380
cgatgccgcg gtcactgcgg ccatcaatgg cgggagcggc ggcggtggcg gtggtggaaa    1440
cacctgacc aacggcactc cggtgaccgg cctgggcgcg cgactggcg cggaattgaa     1500
ctacaccatc accgtgccgg ccgcagcgcg caccttgacg gtgaccacca gcggcggcag    1560
cggcgatgcc gacctgtatg tgcgcgccgg cagtgcaccg accgactcgg cttacacctg    1620
ccgcccatac cgcagcggca atgccgagac ctgcaccatc accgcaccgt ccggaacgta    1680
```

-continued

```
ttacgtgcgt ctgaaggcct acagcacgtt ctccggcgtc accctgcgcg ccagctacta    1740
a                                                                    1741

<210> SEQ ID NO 17
<211> LENGTH: 1170
<212> TYPE: DNA
<213> ORGANISM: Bacillus lentus
<220> FEATURE:
<223> OTHER INFORMATION: Bacillus lentus DSM 5483

<400> SEQUENCE: 17
atgatgagga aaaagagttt ttggcttggg atgctgacgg ccttcatgct cgtgttcacg      60
atggcattca gcgattccgc ttctgcagcc cgggctgagg aagcaaaaga aaaatattta     120
attggcttta atgagcagga agctgtcagt gagtttgtag aacaagtaga ggcaaatgac     180
gaggtcgcca ttctctctga ggaagaggaa gtcgaaattg aactgcttca tgagtttgaa     240
acgattcctg ttttatccgt tgagttaagc ccagaagatg tggacgcgct tgaacttgat     300
ccagcgattt cttatattga agaggatgca gaagtaacga caatggcgca atcagtgcca     360
tggggaatta gccgtgtgca agccccggct gcccataacc gtggattgac aggttctggt     420
gtaaaagttg ctgtcctcga tacaggtatt tccactcatc cagacttaaa tattcgtggt     480
ggcgctagct ttgtaccagg ggaaccatcc actcaagatg ggaatgggca tggcacgcat     540
gtggccggga cgattgctgc tttaaacaat tcgattggcg ttcttggcgt agcgcctagt     600
gcggaactat acgctgttaa agttttagga gccgacggta gaggtgcaat cagctcgatt     660
gcccaagggt tggaatgggc agggaacaat ggcatgcacg ttgctaattt gagtttagga     720
agcccttcgc caagtgccac acttgagcaa gctgttaata gcgcgacttc tagaggcgtt     780
cttgttgtag cggcatctgg gaattcaggt gcaagctcaa tcagctatcc ggcccgttat     840
gcgaacgcaa tggcagtcgg agctactgac caaaacaaca accgcgccag cttttcacag     900
tatggcgcag ggcttgacat tgtcgcacca ggggtaaacg tgcagagcac atacccaggt     960
tcaacgtatg ccagcttaaa cggtacatcg atggctactc ctcatgttgc aggtgcagca    1020
gcccttgtta acaaaagaa cccatcttgg tccaatgtac aaatccgcaa ccatctaaag     1080
aatacggcaa cgagcttagg aagcacgaac ttgtatggaa gcggacttgt caatgcagaa    1140
gcggcaacac gctaagcggc aacacgctaa                                     1170
```